(12) United States Patent
Daniell

(10) Patent No.: US 11,332,754 B2
(45) Date of Patent: May 17, 2022

(54) CODON OPTIMIZATION FOR INCREASING TRANSGENE EXPRESSION IN CHLOROPLASTS OF HIGHER SEED PLANTS

(71) Applicant: THE TRUSTEES OF THE UNIVERSITY OF PENNSYLVANIA, Philadelphia, PA (US)

(72) Inventor: Henry Daniell, Media, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 187 days.

(21) Appl. No.: 16/086,416

(22) PCT Filed: Mar. 20, 2017

(86) PCT No.: PCT/US2017/023263
§ 371 (c)(1),
(2) Date: Sep. 19, 2018

(87) PCT Pub. No.: WO2017/165320
PCT Pub. Date: Sep. 28, 2017

(65) Prior Publication Data
US 2019/0194679 A1 Jun. 27, 2019

Related U.S. Application Data

(60) Provisional application No. 62/310,788, filed on Mar. 20, 2016.

(51) Int. Cl.
| | | |
|---|---|---|
| *C12N 15/82* | (2006.01) | |
| *C07K 14/65* | (2006.01) | |
| *C07K 14/755* | (2006.01) | |
| *A61K 39/12* | (2006.01) | |
| *A61P 31/14* | (2006.01) | |
| *A61P 1/02* | (2006.01) | |
| *A61K 9/68* | (2006.01) | |
| *C07K 14/47* | (2006.01) | |
| *C12N 7/00* | (2006.01) | |
| *C12N 9/26* | (2006.01) | |
| *A61K 39/00* | (2006.01) | |

(52) U.S. Cl.
CPC ........ *C12N 15/8258* (2013.01); *A61K 9/0058* (2013.01); *A61K 39/12* (2013.01); *A61P 1/02* (2018.01); *A61P 31/14* (2018.01); *C07K 14/4723* (2013.01); *C07K 14/65* (2013.01); *C07K 14/755* (2013.01); *C12N 7/00* (2013.01); *C12N 9/2408* (2013.01); *C12N 15/8214* (2013.01); *C12N 15/8216* (2013.01); *C12N 15/8257* (2013.01); *C12Y 302/01084* (2013.01); *A61K 2039/542* (2013.01); *A61K 2039/545* (2013.01); *A61K 2039/575* (2013.01); *A61K 2039/6037* (2013.01); *C07K 2319/00* (2013.01); *C12N 2770/32634* (2013.01)

(58) Field of Classification Search
None
See application file for complete search history.

(56) References Cited

U.S. PATENT DOCUMENTS

| | | | |
|---|---|---|---|
| 2006/0253935 A1 | 11/2006 | Daniell | |
| 2008/0038193 A1 | 2/2008 | Wouters et al. | |
| 2011/0179530 A1* | 7/2011 | Daniell ................ | C07K 14/415 800/317.3 |
| 2013/0281671 A1 | 10/2013 | Peters et al. | |
| 2015/0030575 A1* | 1/2015 | Daniell .................... | A61P 3/04 424/93.21 |
| 2015/0273082 A1 | 10/2015 | Nathwani et al. | |
| 2015/0361158 A1 | 12/2015 | Tan et al. | |
| 2016/0289277 A1 | 10/2016 | Herzog et al. | |

FOREIGN PATENT DOCUMENTS

| | | |
|---|---|---|
| JP | 2005/185182 | 7/2005 |
| WO | 2007/053731 A2 | 5/2007 |

OTHER PUBLICATIONS

Wu, Shuangxiu, et al. (Bioresource technology 102.3 (2011): 2610-2616) . (Year: 2011).*
Rybicki, Edward P., "Plant-based vaccines against viruses", Virology Journal, 11: 205 (2014).
Shenoy, Vinayak et al., "Oral Delivery of Angiotensin-Converting Enzyme 2 and Angiotensin-(1-7) Bioencapsulated in Plant Cells Attenuates Pulmonary Hypertension", Hypertension, 64(6): 1248-1259 (2014).
Sherman, Alexandra et al., "Suppression of inhibitor formation against FVIII in a murine model of hemophilia A by oral delivery of antigens bioencapsulated in plant cells", Blood, 124(10): 1659-1668 (2014).
Shil, Pollob K. et al., "Oral Delivery of ACE2/Ang-(1-7) Bioencapsulated in Plant Cells Protects against Experimental Uveitis and Autoimmune Uveoretinitis", Molecular Therapy, 22(12): 2069-2082 (2014).
Thanavala, Yasmin et al., "Immunogenicity in humans of an edible vaccine for hepatitis B", PNAS, 102(2): 3378-3382 (2005).
Verma, Dheeraj et al., "A protocol for expression of foreign genes in chloroplasts", Nature Protocols, 3(4): 739-758 (2008).
Verma, Dheeraj et al., "Oral delivery of bioencapsulated coagulation factor IX prevents inhibitor formation and fatal anaphylaxis in hemophilia B mice", PNAS, 107(15): 7101-7106 (2010).

(Continued)

*Primary Examiner* — Charles Logsdon
(74) *Attorney, Agent, or Firm* — Kathleen D. Rigaut; Howson & Howson LLP

(57) ABSTRACT

Methods for improving transgene in chloroplasts are disclosed along with improved transgenes so produced and methods of use thereof for the treatment of disease. Specifically, the methods comprising analyzing the native sequence of a nucleic acid encoding a protein of interest and replacing codons in said sequence with those preferentially used in psbA genes in chloroplasts in higher plants.

8 Claims, 40 Drawing Sheets

Specification includes a Sequence Listing.

(56) References Cited

OTHER PUBLICATIONS

Waheed, Mohammad et al., "Plastid expression of a double-pentameric vaccine candidate containing human papillomarvus-16 L1 antigen fused with LTB as adjuvant: transplastomic plants show pleiotropic phenotypes", Plant Biotechnology Journal, 9: 651-660 (2011).
Wang, Xiaomei et al., "Plant-based oral tolerance to hemophilia therapy employs a complex immune regulatory response including LAP+ CD4+ T cells", Blood, 125(15): 2418-2427 (2015).
Xiao, Yuhong et al., "Low cost-delivery of proteins bioencapsulated in plant cells to human non-immune or immune modulatory cells", Biomaterials, 80: 68-79 (2016).
Ye, Guang-Ning et al., "Plastid-expressed 5-enolpyruvylshikimate-3-phosphate synthase genes provide high level glyphosate tolerance in tobacco", The Plant Journal, 25(3): 261-270 (2001).
Yu, Chien-Hung et al., "Codon usage influences the local rate of translation elongation to regulate co-translational protein folding", Mol. Cell., 59(5): 744-754 (2015).
Zoschke, Reimo et al., "A Rapid Ribosome Profiling Method Elucidates Chloroplast Ribosome Behavior In Vivo", The Plant Cell, 25: 2265-2275 (2013).
Zoschke, Reimo et al., "Genome-wide analysis of thylakoid-bound ribosomes in maize reveals principles of cotranslational targeting to the thylakoid membrane", PNAS, E1678-E1687 (2015).
Morton et al., "The atypical codon usage of the plant psbA gene may be the remnant of an ancestral bias", PNAS, 94(21): 11434-8 (1997).
Angov et al., "Codon usage: Nature's roadmap to expression and folding of proteins", Biotechnol. J., 6(6): 650-9 (2011).
Kwon et al., "Codon Optimization to Enhance Expression Yields Insights into Chloroplast Translation", Plant Physiol., 172(1): 62-77 (2016).
Vukusic et al., "Recombinant therapeutic proteins produced in plants: toward engineering of human-type O- and N-glycosylation", Peri. Biol., 118(2): 75-90 (2016).
International Search Report and Written Opinion, issued in corresponding International Application No. PCT/US17/23263.
Nakamura, Masayuki et al., "Cooperation between the chloroplast psbA 5'-untranslated region and coding region ios important for translational initiation: the chloroplast translation machinery cannot read a human viral gene coding region", The Plant Journal, 85: 772-780 (2016).
Extended European Search Report, dated Jul. 19, 2016, issued in corresponding European Patent Application No. 17770930.0.
Arlen, Philip A. et al., "Field production and functional evaluation of chloroplast-derived interferon-a2b", Plant Biotechnol., 5(4): 511-525 (2007).
Bally, Julia et al., "Plant Physiological Adaptations to the Massive Foreign Protein Synthesis Occurring in Recombinant Chloroplasts", Plant Physiology, 150: 1474-1481 (2009).
Barkan, Alice, "Proteins encoded by a complex chloroplast transcription unit are each translated from both monocistronic and polycistronic mRNAs", The EMBO Journal, 7(9): 2637-2644 (1988).
Birch, Ian Birch-Machin et al., "Accumulation of rotavirus VP6 protein in chloroplasts of transplatomic tobacco is limited by protein stability", Plant Biotechnology Journal, 2: 261-270 (2004).
Borchers, A.-M. Inka et al., "Increased accumulation and stability of rotavirus VP6 protein in tobacco chloroplasts following changes to the 5' untranslated region and the 5' end of the coding region", Plant Biotechnology Journal, 10: 422-434 (2012).
Boyhan, Diane et al., "Low-cost production of proinsulin and tobacco and lettuce chloroplasts for injectable or oral delivery of functional insulin and C-peptide", Plant Biotechnol., J., 9(5): 585-598 (2011).
Brown, Betty et al., "Complete Genomic Sequencing Shows that Polioviruss and Members of Human Enterovirus Species C are Closely Related in the Noncapsid Coding Region",Journal of Virology, 77(16): 8973-8984 (2003).

Buchman, George W., "A protein-based smallpox vaccine protects non-human primates from a lethal monkeypox virus challenge", Vaccine, 28(40): 6627-6636 (2010).
Burioni, Roberto et al., "Recombinant human Fab to glycoprotein D neutralizes infectivity and prevents cell-to-cell transmission of herpes simplex viruses 1 and 2 in vitro", Proc. Natl. Acad. Sci. USA, 91: 355-359 (1994).
Burns, Cara C., "Multiple Independent Emergences of Type 2 Vaccine-Derived Polioviruses during a Large Outbreak in Northern Nigeria", Journal of Virology, 87(9): 4907-4922 (2013).
Burns, Cara C., "Vaccine-Derived Polioviruses", Journal of Infectious Diseases, 210(S12): S283-93 (2014).
Chan, Hui-ting et al., "Plant-made oral vaccines against human infectious diseases—Are we there yet?", Plant Biotechnol. J., 13(8):p. 1056-1070 (2015).
Daniell, H. et al., "Transient foreign gene expression in chloroplasts of cultured tobacco cells after biolistic delivery of chloroplast vectors", Proc. Natl. Acad. Sci. USA, 87: 88-92 (1990).
Daniell, Henry et al., "Containment of herbicide resistance through genetic engineering of the chloroplast genome", Nat. Biotechnol., 16(4): 345-348 (1998).
Daniell, H. et al., "Optimization of codon composition and regulatory elements for expression of human insulin like growth factor-1 in transgenic chloroplasts and evaluation of structural identity and function", BMC Biotechnology, 9: 33 (2009).
Davoodi-Semiromi, Abdoreza et al., "Chloroplast-derived vaccine antigens confer dual immunity against chlolera and malaria by oral or injectable delivery", Plant Biotechnol. J., 8(2): 223-242 (2010).
Decosa, Brandy et al., "Overexpression of the Bt cry2Aa2 operon in chloroplasts leads to formation of insecticidal crystals", Nat. Biotechnol., 19(1): 71-74 (2001).
Decosta, Fernanda et al., Alternative Inactivated Poliovirus Vaccines Adjuvanted with Quillaja brasiliensis or Quil-A Saponins Are Equally Effective in Inducing Specific Immune Responses.
Degray, Gerald et al., "Expression of an Antimicrobial Peptide via the Chloroplast Genome to Control Phytopathogenic Bacteria and Fungi", Plant Physiology, 127: 852-862 (2001).
Dietrich, Jes et al.,. "Inducing Dose Sparing with Inactivated Polio Virus Formulaterd in Adjuvant CAF02", PLoS One, 9(6): e100879 (2014).
Eibl, Christian et al., "In vivo analysis of plastid psbA, rbcL and rpl32 UTR elements by chloroplast transformation tobacco plastic gene expression is controlled by modulation of transcript levels and translation efficiency", The Plant Journal, 19(3): 333-345 (1999).
Famulare, Michael et al., "Extracting transmission networks from phylogeographic data for epidemic and endemic diseases: Ebola virus in Sierra Leone, 2009 H1N1 pandemic influenza and polio in Nigeria", Int. Health, 7: 130-138 (2015).
Fogg, Christiana et al., "Protective Immunity to Vaccinia Virus Induced by Vaccination with Multiple Recombinant Outer Membrane Proteins of Intracellular and Extracellular Virions", Journal of Virology, 78(19): 10230-10237 (2004).
Fogg, Christiana et al., "Adjuvant-Enhanced Antibody Responses to Recombinant Proteins Correlates with Protection of Mice and Monkeys to Orthopoxvirus Challenges", Vaccine, 25(15): 2787-2799 (2007).
Gallien, Sebastien et al., "Targeted Proteomic Quantification on Quadruple-Orbitrap Mass Spectrometer", Molecular & Cellular Proteomics 11.12, pp. 1709-1723 (2012).
Hasson, Syed Waqas et al., "Expression of HPV-16L1 capsomeres with glutathione-S-transferase as a fusion protein in tobacco plastids: An approach for a capsomere-based HPV vaccine", Human Vaccines & Immunotherapeutics, 10:10: 2975-2982 (2014).
Ingolia, Nicholas T. et al., "Genome-wide analysis of translational efficiency reveals distinct but overlapping functions of yeast DEAD-box RNA helicases Ded1 and eIF4A", Genome Research, 25: 1996-1205 (2015).
Jiang, Ping et al., "Evidence for emergence of diverse polioviruses from C-cluster coxsackie A viruses and implications for global poliovirus eradication", PNAS, 104(22): 9457-9462 (2007).
Jin, Shuangxia et al., "Engineered Chloroplast Genome just got Smarter", Trends Plant Sci., 20(10): 622-640 (2015).

(56) References Cited

OTHER PUBLICATIONS

Kanagaraj, Anderson Paul et al., "Expression of dengue-3 premembrane and envelope polyprotein in lettuce chloroplasts", Plant Mol. Biol., 76(3-5): 323-333 (2011).
Kohli, Neha et al., "Oral Delivery of Bioencapsulated Proteins Across Blood-Brain and Blood-Retinal Barriers", Molecular Therapy, 22(3): 535-546 (2014).
Kong, Qingxian et al., "Oral immunization with hepatitis B surface antigen expressed in transgenic plants", PNAS, 98(20): 11539-11544 (2001).
Kouiavskaia, Diana et al., "Intradermal Inactivated Poliovirus Vaccine: A Preclinical Dose-Finding Study", JID, 211: 1447-1450 (2015).
Kwon, Kwang-Chui et al., "Oral delivery of human biopharmaceuticals, autoantigens and vaccine antigens bioencapsulated in plant cells", Adv. Drug Deliv. Rev., 65(6): 782-799 (2013).
Lakshmi, Priya et al., "Low Cost Tuberculosis Vaccine Antigens in Capsules: Expression in Chloroplasts, Bio-Encapsulation, Stability and Functional Evaluation In Vitro", PLoS One, 8(1): e54708 (2013).
Laxmivandana, Rongala et al., "Characterization of the Non-Polio Enterovirus Infections Associated with Acute Flaccid Paralysis in South-Western India", PLoS One, 8(4): e61650 (2013).
Lee, Seung-Bum et al., "Expression and characterization of antimicrobial peptides Retrocyclin-101 and Protegrin-1 in chloroplasts to control viral and bacterial infections", Plant Biotechnol. J., 9(1): 100-115 (2011).
Lee, Goeun et al., "Oral immunization of haemaggulutinin H5 expressed in plant endoplasmic reticulum with adjuvant saponin protects mice against highly pathogenic avian influenza A virus infection", Plant Biotechnology Journal, 13: 62-72 (2015).
Leon, Ileana et al., "Quantitative Assessment of In-solution Digestion Efficiency Identifies Optimal Protocols for Unbiased Protein Analysis", Molecular & Cellular Proteomics 12.10, 2992-3005 (2013).
Limaye, Arati et al., Receptor-mediated oral delivery of a bioencapsulated green fluorescent protein expressed in transgenic chloroplasts into the mouse circulatory system, FASEB J., 20(7): 959-961 (2006).
Lung, Birgit et al., "Identification of small non-coding RNAs from mitochondria and chloroplasts", Nucleic Acids Research, 34(14): 3842-3852 (2006).
McCabe, Matthew S. et al., "Plastid transformation of high-biomass tobacco variety Maryland Mammoth for production of human immunodeficiency virus type 1 (HIV-1) p24 antigen", Plant Biotechnology Journal, 6: 914-929 (2008).
Nakamura, Masayuki et al., "Translation efficiencies of synonymous codons are not always correlated with codon usage in tobacco chloroplasts", The Plant Journal, 49; 128-134 (2006).
Parker, Edward P.K. et al., "Impact of inactivated poliovirus vaccine on mucosal immunity: implications for the polio eradication endgame", Expert Rev. Vaccines, 14(8): 1113-1123 (2015).
Plotkin, Stanley A., Correlates of Protection Induced by Vaccination, Clinical and Vaccine Immunology, 17(7): 1055-1065 (2010).
Quesada-Vargas, Tania et al., "Characterization of Heterologous Multigene Operons in Transgenic Chloroplasts. Transcription, Processing, and Translation", Plant Physiology, 138: 1746-1762 (2005).
Rakoto-Andrianarivelo, Mala et al., "High Frequency of Human Enterovirus Species C Circulation in Madagascar", Journal of Clinical Microbiology, 43(1): 242-249 (2005).
Rosenberg, Alan et al., "Effects of Consecutive AGG Codons on Translation in *Escherichia coli*, Demonstrated with a Versatile Codon Test System", Journal of Bacteriology, 175(3): 716-722 (1993).
Ruhlman, Tracey et al., "Expression of cholera toxin B-proinsulin fusion protein in lettuce and tobacco chloroplasts—oral administration protects against development of insulitis in non-obese diabetic mice", Plant Biotechnology Journal, 5: 495-510 (2007).
Ruhlman, Tracey et al., "The Role of Heterologous Chloroplast Sequence Elements in Transgene Integration and Expression", Plant Physiology, 152: 2088-2104 (2010).

\* cited by examiner

FIG. 1

Collection of all sequence data from psbA genes from 133 plant species

Analysis of codon usage

Development of algorithm and software to arrive at

Codon Preference Table

| TTT (72%) | F | TCT (43%) | S | TAT (53%) | Y | TGT (80%) | C |
| --- | --- | --- | --- | --- | --- | --- | --- |
| TTC (28%) | F | TCC (13%) | S | TAC (47%) | Y | TGC (19%) | C |
| TTA (26%) | L | TCA (6%) | S | TAA (100%) | STOP | TGA (0%) | |
| TTG (22%) | L | TCG (2%) | S | TAG (0%) | | TGG (100%) | W |
| CTT (20%) | L | CCT (66%) | P | CAT (48%) | H | CGT (64%) | R |
| CTC (0%) | L | CCC (2%) | P | CAC (52%) | H | CGC (18%) | R |
| CTA (27%) | L | CCA (26%) | P | CAA (80%) | Q | CGA (6%) | R |
| CTG (4%) | L | CCG (6%) | P | CAG (20%) | Q | CGG (1%) | R |
| ATT (57%) | I | ACT (58%) | T | AAT (47%) | N | AGT (22%) | S |
| ATC (34%) | I | ACC (31%) | T | AAC (53%) | N | AGC (15%) | S |
| ATA (9%) | I | ACA (10%) | T | AAA (84%) | K | AGA (12%) | R |
| ATG (100%) | M | ACG (1%) | T | AAG (16%) | K | AGG (7%) | R |
| GTT (45%) | V | GCT (69%) | A | GAT (81%) | D | GGT (67%) | G |
| GTC (2%) | V | GCC (7%) | A | GAC (19%) | D | GGC (13%) | G |
| GTA (51%) | V | GCA (19%) | A | GAA (75%) | E | GGA (18%) | G |
| GTG (2%) | V | GCG (5%) | A | GAG (25%) | E | GGG (2%) | G |

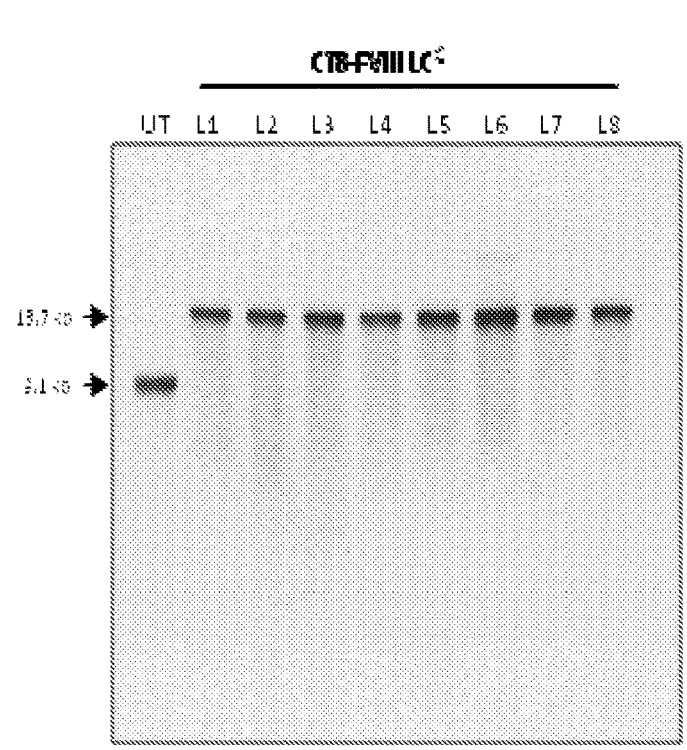
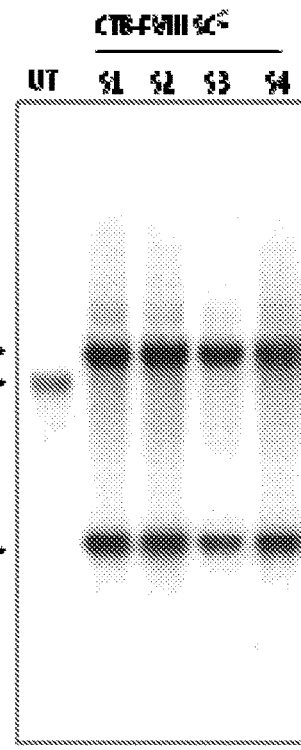
FIG. 3A  FIG. 3B
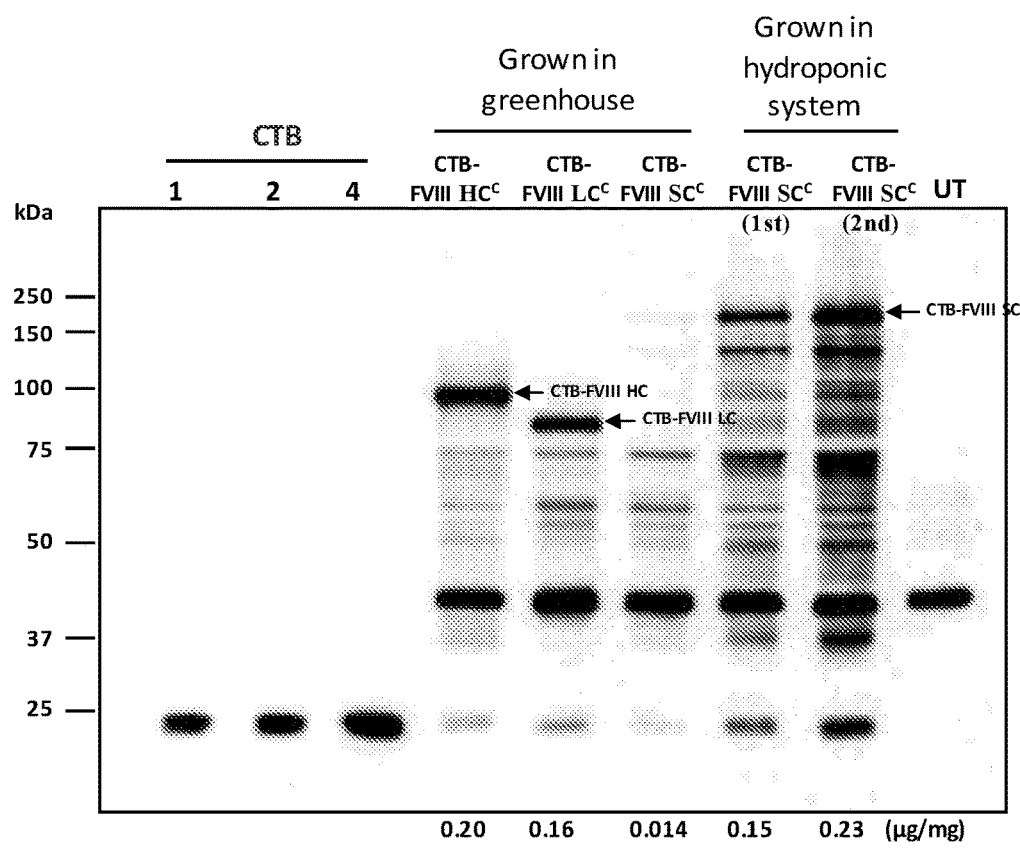
FIG. 3C

FIG. 6C CTB-VP1 Protein
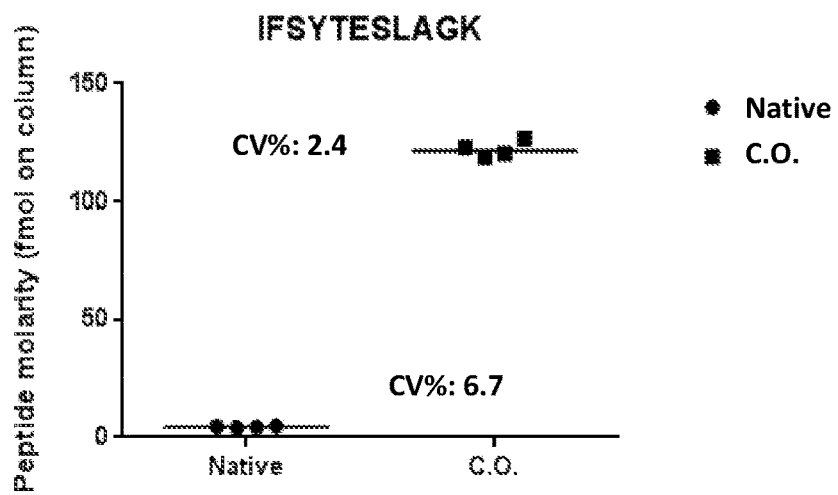
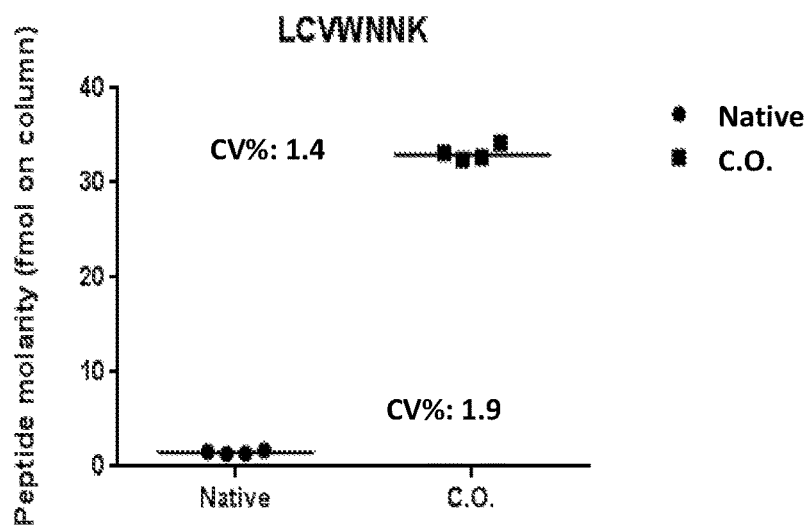
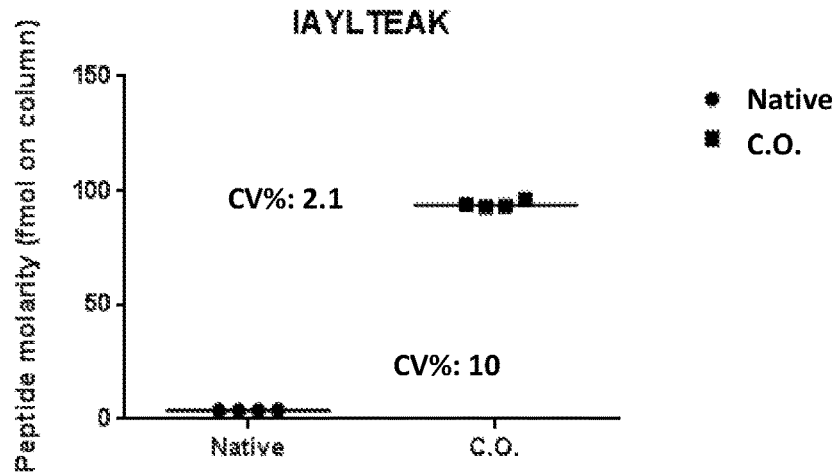

| Sample | Total Ribosome Footprint Reads Aligned to CP genome | Ratio: Transgene/Total ribosome footprint reads | Ratio: Transgene/psbA | Ratio: Transgene/rbcL |
|---|---|---|---|---|
| Tobacco CTB-VP1 (N) | 45,846 | 0.05 | 0.15 | 0.34 |
| Tobacco CTB-VP1 (CO) | 87,498 | 0.25 | 2.41 | 0.81 |
| Lettuce CTB-F8 HC (N) | 30,399 | 0.37 | 1.80 | 2.28 |
| Lettuce CTB-F8 HC (CO) | 55,347 | 0.20 | 0.82 | 0.72 |

FIG. 8C

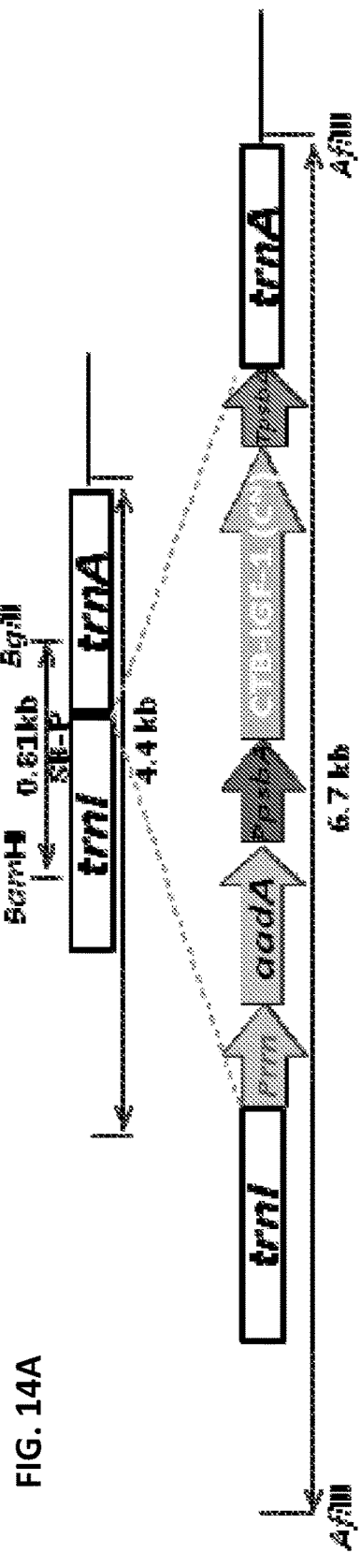
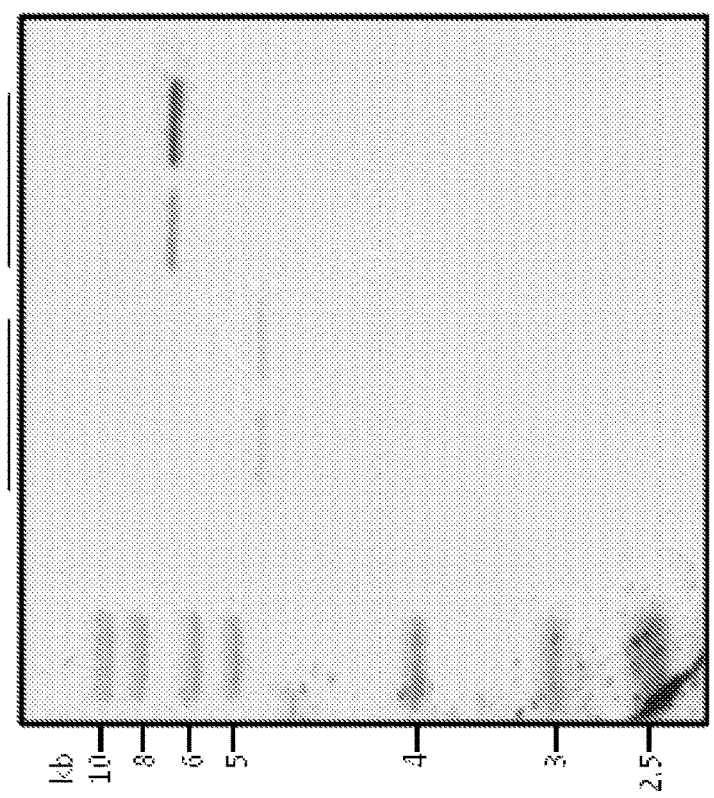
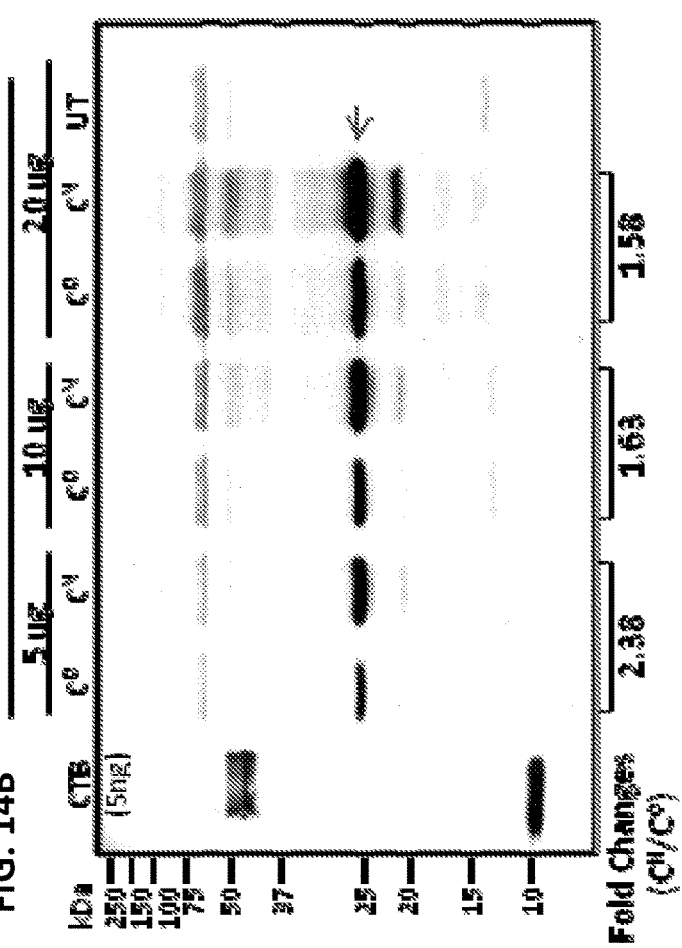
FIG. 14A
FIG. 14B
FIG. 14C

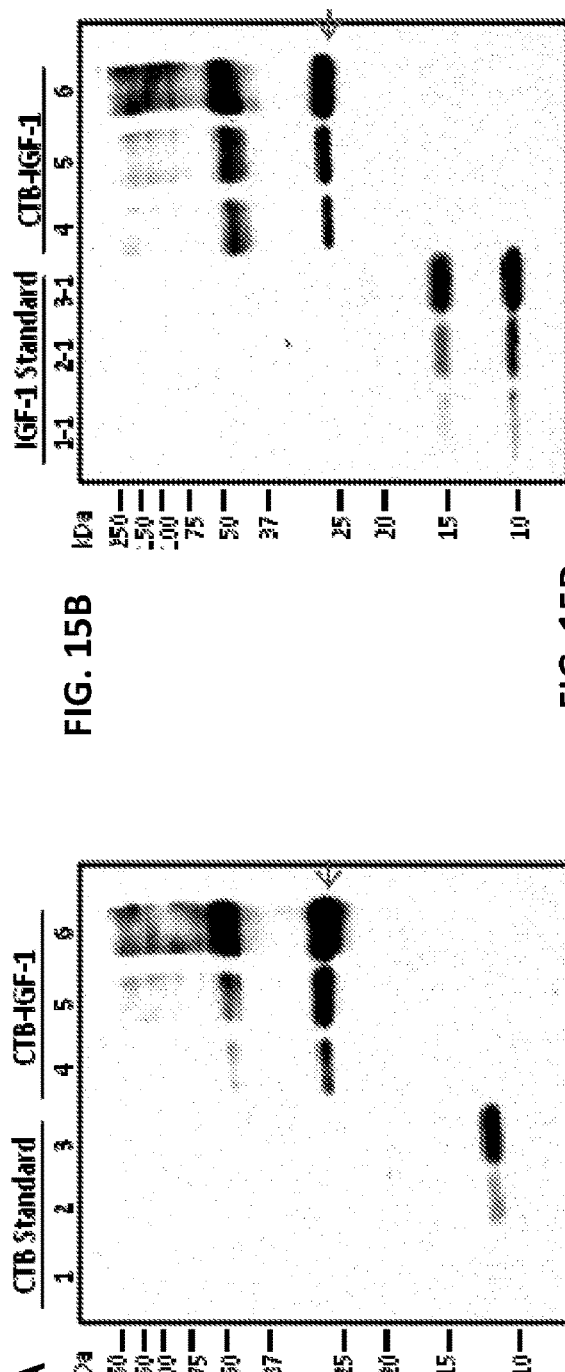
FIG. 15B
FIG. 15A
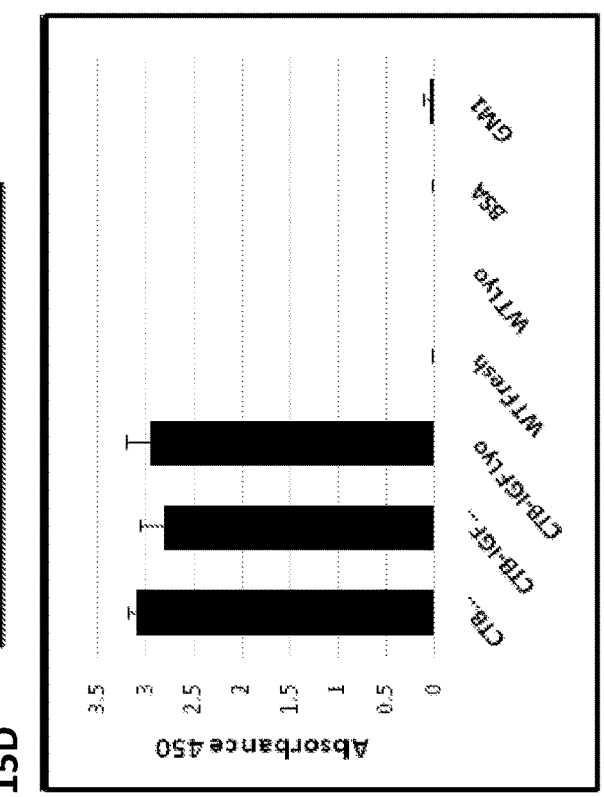
FIG. 15D
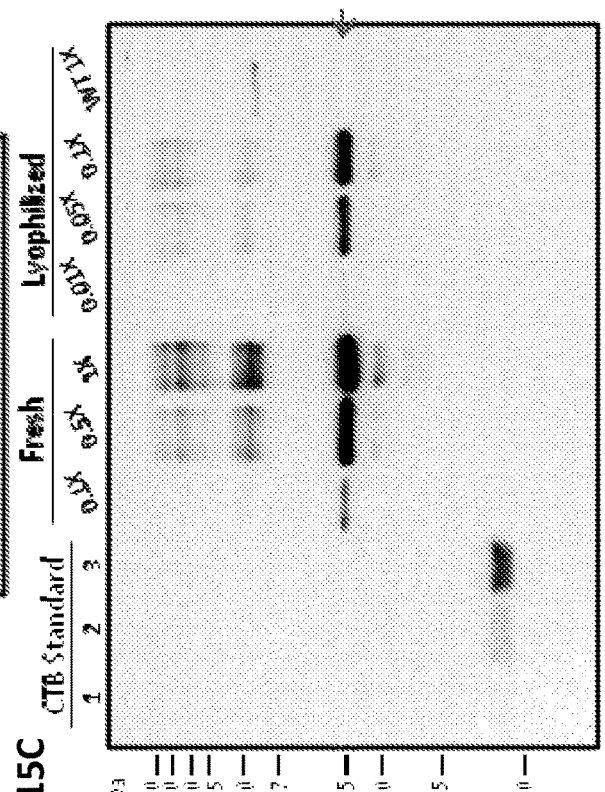
FIG. 15C

| | | | | | | | | | | | |
|---|---|---|---|---|---|---|---|---|---|---|---|
| IGF-1 (Nat) | GGA | CCG | GAG | ACG | CTC | TGC | GGG | GCT | GAG | CTG | GTG | GAT | GCT | CTT | CAG | TTC | GTG | TGT | GGA | GAC | AGG | GGC | TTT | TAT | TTC | AAC | AAG | 81 |
| IGF-1 (Co) | GGT | CCT | GAA | ACT | CTA | TGT | GGT | GCT | GAA | TTG | GTA | GAC | GCT | CTT | CAA | TTC | GTT | TGT | GGC | GAT | CGT | GGT | TTC | TAC | TTC | AAC | AAA | 81 |

| | | | | | | | | | | | |
|---|---|---|---|---|---|---|---|---|---|---|---|
| IGF-1 (Nat) | CCC | ACA | GGG | TAT | GGC | TCC | AGC | AGT | CGG | AGG | GCG | CCT | CAG | ACA | GGC | ATC | GTG | GAT | GAG | TGC | TGC | TTC | CGG | AGC | TGT | GAT | CTA | 162 |
| IGF-1 (Co) | CCT | ACC | GGT | TAT | GGT | TCT | AGC | TCT | CGT | CGC | GCA | CCA | CAA | ACT | GGA | ATT | GTA | GAT | GAG | TGT | TGC | TTT | AGA | AGT | TGT | GAT | CTT | 162 |

| | | | | | | | | | | | |
|---|---|---|---|---|---|---|---|---|---|---|---|
| IGF-1 (Nat) | AGG | AGG | CTG | GAG | ATG | TAT | TGC | GCA | CCC | CTC | AAG | CCT | GCC | AAG | TCA | GCT | CGC | TCT | GTC | CGC | CAG | GCC | ACC | CAC | GAC | ATG | 243 |
| IGF-1 (Co) | CGT | CGC | CTT | GAA | ATG | TAC | TGT | GCT | CCT | CTT | AAA | CCA | GCC | AAA | TCT | GCT | CGT | AGT | GTT | CGT | CAA | GCT | ACC | CAT | GAT | ATG | 243 |

| | | | | | | | | | | | |
|---|---|---|---|---|---|---|---|---|---|---|---|
| IGF-1 (Nat) | CCC | AAG | ACC | CAG | AAG | GAA | GTA | CAT | TTG | AAG | AAC | GCA | AGT | AGA | GGG | AGT | GCA | GGA | AAC | AAG | AAC | TAC | AGG | ATG | 315 |
| IGF-1 (Co) | CCT | AAA | ACT | CAG | AAG | GAA | GTA | CAC | TTA | AAA | AAT | GCT | TCC | CGA | GGT | TCT | GCT | GGA | AAC | AAA | AAT | TAT | CGT | ATG | 315 |

Mutanase Assay

| Mutanase | Reducing Sugar (μg) |
|---|---|
| J&J Mutanase (Undiluted) | 14.73 |
| 1:10 | 9.95 |
| 1:20 | 7.45 |
| 1:50 | 2.01 |

| Mutanase (pLS-MF) | Reducing Sugar (μg) |
|---|---|
| Mutanase (Undiluted) | 9.84 |
| 1:10 | 2.34 |
| 1:20 | 1.53 |
| 1:50 | 0.81 |

| Mutanase (pLD) | Reducing Sugar (μg) |
|---|---|
| Mutanase (Undiluted) | 8.91 |
| 1:10 | 3.49 |
| 1:20 | 1.81 |
| 1:50 | 0.22 |

Mutan hydrolysis of bacterial purified recombinant Mutanase. Mutanase assay was performed by following the Somogyi-Nelson method with Somogyi copper reagent and Nelson reagent.

SEQUENCE LISTING

```
<160> NUMBER OF SEQ ID NOS: 25

<210> SEQ ID NO 1
<211> LENGTH: 2262
<212> TYPE: DNA
<213> ORGANISM: Artificial Sequence
<220> FEATURE:
<223> OTHER INFORMATION: codon-optimized FVIII, heavy chain composed of
      A1 and A2 domains

<400> SEQUENCE: 1
gcaactcgtc gttactattt aggagccgtt gaactaagtt gggattatat gcaatctgat      60
ctaggtgaat taccagtaga cgctcgtttc cctcctcgtg ttcctaaatc ttttccttt     120
```

-continued

```
aacacatccg ttgtttacaa aaagactcta tttgttgagt tcactgatca cctattcaac      180
attgctaaac cacgtcctcc atggatgggc ctacttggcc ctactattca agctgaagta      240
tatgatactg ttgtaattac cctaaagaac atggcttccc accctgtttc tttacatgca      300
gttggtgttt cttactggaa agctagtgag ggtgctgaat acgatgatca gacttcccaa      360
cgagaaaaag aagatgataa agttttccct ggtggctctc acacctacgt tggcaagtt       420
ttaaaagaaa acggacctat ggcctccgat ccattatgtc taacttacag ttatctatct      480
catgttgatt tggttaaaga tttgaatagt ggtctaattg gtgctctatt agtatgtcgt      540
gaaggttctc ttgcaaaaga aaaaacacaa actcttcaca aattcatcct tttatttgct      600
gtatttgatg aaggaaaaag ctggcacagt gaaactaaaa attctttgat gcaagatcgt      660
gatgctgcaa gcgctcgcgc ttggccaaaa atgcacactg taaatggtta cgtaaataga      720
tctttgcctg gtcttattgg ctgtcaccgt aaaagcgtat attggcatgt aattggtatg      780
ggtaccactc ctgaggtaca ctccatcttc ttagaaggac atactttctt agtacgcaat      840
cacagacagg cttctcttga aatttctcca atcactttc ttacagctca gaccttgtta      900
atggacttag acagttctt actattttgt cacatcagct ctcatcaaca tgacggtatg       960
gaagcatacg taaggttga tagctgccca gaggaacctc aattgcgtat gaaaaacaac      1020
gaagaagctg aagattatga cgatgatcta actgattctg agatggatgt tgttcgtttc      1080
gatgatgaca attctccaag cttcatacaa attagaagcg tagcaaagaa acatccaaaa      1140
acttgggtac actacattgc tgcagaagaa gaggattggg attatgcccc tttggttctt      1200
gctccagacg atcgtagtta taaatctcaa tatttgaaca acggtcctca acgcatcggt      1260
cgaaaataca aaaagttag atttatggct tacaccgatg aaactttcaa gacccgtgaa       1320
gctattcagc atgaatctgg aattcttggt cctctattat atggtgaagt tggtgatact      1380
cttctaatta ttttcaagaa ccaagctagc cgtccttaca catttatcc tcatggcatc       1440
actgatgtac gcccttttgta ttctcgacgt ttacctaaag gagtaaaaca cttaaaggat     1500
ttccctatcc ttccaggtga aattttcaaa tataaatgga ccgtaaccgt agaggatggt      1560
ccaaccaaat ctgaccctcg ctgtctaact cgttactact ctagcttcgt aaatatggaa      1620
cgtgatcttg ctagtggttt gatcggtcca ttactaatct gttacaaaga gtccgttgac     1680
caaagaggca accaaattat gagtgataaa cgtaatgtta tactattcag tgttttcgat     1740
gaaaatcgtt cttggtatct aactgaaaat attcaacgat ttttacctaa ccctgctggt     1800
gttcaactag aggatcctga attccaagcc agtaatatca tgcatagcat taatggatat     1860
gtattcgata gtttacaatt atccgttgt ttgcatgaag ttgcttactg gtatattcta      1920
tctatcggtg ctcaaactga cttcctatct gtattcttct ctggttatac cttcaaacac     1980
aaaatggtat acgaggatac cttgacccctt ttcccttttca gtggtgaaac agttttcatg    2040
agtatggaaa acccaggcct ttggatccta ggttgtcaca attctgatttt ccgtaatcgc    2100
ggtatgactg ctttgctaaa agtatcttct tgcgataaaa acactggtga ttactatgag     2160
gatagttatg aagatatatc tgcttatttg ctatccaaaa acaatgctat tgagcctcgt     2220
tctttctctc aaaatccacc tgttttaaaa cgtcaccaac gc                        2262
```

<210> SEQ ID NO 2
<211> LENGTH: 2055
<212> TYPE: DNA
<213> ORGANISM: Artificial Sequence
<220> FEATURE:
<223> OTHER INFORMATION: codon-optimized FVIII, light chain composed of A3, C1, and C2 domains

<400> SEQUENCE: 2

```
gaaattactc gcaccactct acaatctgat caagaagaga tcgattatga tgatactatt      60
agtgtagaaa tgaaaaaaga agattttgac atttacgatg aagatgaaaa ccaaagtcct     120
cgctccttcc aaaaaaaaac tagacattat ttcattgctg ctgtagagcg tttatgggat     180
tacggtatgt ctagttctcc tcacgtttta cgtaaccgtg cacaaagcgg ctctgtacct     240
caattcaaaa aagtagtatt ccaagagttc actgatggaa gtttcacaca accattgtac     300
cgcggagaac ttaatgaaca cctaggtcta ttaggtcctt acatacgagc agaagtagaa     360
gataacatta tggttacctt ccgtaaccaa gcctctcgtc cttattcctt ttacagctct     420
ctaatcagtt acgaagaaga ccagagacaa ggtgcagagc cacgtaaaaa tttcgttaaa     480
ccaaacgaaa ctaaaaccta tttctggaaa gttcagcatc acatggctcc tacaaaagat     540
gaatttgact gcaaggcttg gcttattttt tctgatgttg atcttgaaaa agatgttcat     600
tctggtctaa taggtccttt gcttgtatgt cataccaata ctctaaatcc tgctcacggt     660
cgtcaggtta ctgtacaaga gttcgctcta ttcttcacca ttttcgatga aactaaaagc     720
tggtatttca cagagaatat ggaacgtaac tgtagagctc catgtaatat tcaaatggaa     780
gatcctactt tcaaagaaaa ctatcgtttt catgccatca acggctacat catggatact     840
cttccaggtt tggtaatggc acaagatcaa agaattcgtt ggtacttgct atctatgggt     900
tctaacgaga atattcactc cattcacttt tctggacatg ttttcactgt tcgtaagaaa     960
gaagaataca aaatggcttt atataacttg tatcctggtg tatttgagac tgtagaaatg    1020
ttaccgtcta aagctggaat ctggcgtgta gaatgtttga ttggtgaaca cttacatgca    1080
ggtatgagta ccttgtttct tgtatatagc aataagtgtc aaacccccact aggtatggcc    1140
tccggacaca ttcgcgattt tcaaattact gcttctggcc aatatggtca gtgggcacct    1200
aaacttgctc gattacacta ttctggttct atcaacgctt ggtctacaaa agaaccattc    1260
agctggatca agttgatct attagctcct atgattatac acggcattaa gactcaaggt    1320
gctcgtcaaa aattctcttc cctttacatc agtcagttca ttattatgta cagtcttgat    1380
ggtaaaaagt ggcaaactta ccgcggtaac tctaccggaa ctttaatggt attcttcggc    1440
aatgttgaca gctctggtat caaacataat atcttcaatc ctcctatcat tgcacgttat    1500
attagactac atccgaccca ttacagtatt cgtagtactc tacgtatgga acttatgggt    1560
tgtgatttaa attcttgttc tatgccttg ggaatggaaa gcaaagctat ctctgatgct    1620
cagatcactg cttcctctta cttccaccaac atgtttgcta cttggtctcc tagtaaagca    1680
cgcctacact tgcagggacg atctaacgct tggcgtcctc aagttaacaa tcctaaagaa    1740
tggttgcaag ttgacttcca gaaaactatg aaagtaactg gtgtaactac tcaaggtgta    1800
aaatctctac taactagcat gtatgttaaa gaattcctta tttcctctag tcaagatggt    1860
catcaatgga ccttattctt tcagaacggt aaagtaaagg tattccaagg taatcaagat    1920
tctttcactc cagtagttaa tagtttagat cctcctttat taactcgtta tttacgtatt    1980
catcctcaat cctgggttca tcaaattgct ttgcgtatgg aggtacttgg ttgtgaagct    2040
caagacttgt attaa                                                     2055
```

```
<210> SEQ ID NO 3
<211> LENGTH: 312
<212> TYPE: DNA
<213> ORGANISM: Artificial Sequence
<220> FEATURE:
<223> OTHER INFORMATION: cholera non-toxic B subunit

<400> SEQUENCE: 3
atgacacctc aaaatattac tgatttgtgt gcagaatacc acaacacaca aatacatacg      60
ctaaatgata agatattttc gtatacagaa tctctagctg aaaaagaga gatggctatc     120 attactttta agaatggtgc aacttttcaa gtagaagtac caggtagtca acatatagat     180
tcacaaaaaa aagcaattga aaggatgaag gataccctga ggattgcata tcttactgaa     240
gctaaagtcg aaaagttatg tgtatggaat aataaaacgc tcatgcgat tgccgcaatt     300 agtatggcaa at                                                        312

<210> SEQ ID NO 4
<211> LENGTH: 1251
<212> TYPE: DNA
<213> ORGANISM: Artificial Sequence
<220> FEATURE:
<223> OTHER INFORMATION: codon-optimized CTB-VP1 sequence

<400> SEQUENCE: 4
atgacacctc aaaatattac tgatttgtgt gcagaatacc acaacacaca aatacatacg      60
ctaaatgata agatattttc gtatacagaa tctctagctg aaaaagaga gatggctatc     120 attactttta agaatggtgc aacttttcaa gtagaagtac caggtagtca acatatagat     180
tcacaaaaaa aagcaattga aaggatgaag gataccctga ggattgcata tcttactgaa     240
gctaaagtcg aaaagttatg tgtatggaat aataaaacgc tcatgcgat tgccgcaatt     300 agtatggcaa atggtcctgg accacgtcgt aaacgctctg ttggtttagg acaaatgttg     360
gaatctatga ttgataacac agtacgtgaa actgttggtg ctgcaacttc tcgtgatgct     420
ctacctaata ctgaagctag tggtcctgct catagcaaag aaattccagc tcttaccgct     480
gttgagaccg gtgctactaa ccctctagtt ccttctgata ctgtacaaac acgtcatgta     540
gttcaacata gaagtcgtag cgaatctagt atcgagtcct tctttgctcg cggtgcttgt     600
gttgcaatca ttaccgtaga taactctgct tccactaaaa ataaagataa gctattcact     660
gtatggaaga ttacctacaa agatactgtt caattacgtc gaaaattaga gttctttact     720
tactcccgct ttgatatgga attcaccttc gtagttactg ctaatttcac cgaaactaac     780
aatggtcacg ctttgaatca ggtatatcaa atcatgtacg taccacctgg agctcctgta     840
ccagaaaaat gggatgacta tacttggcag acttcctcta accctctat tttttataca     900 tacggtaccg cacctgctcg tattagcgtt ccatacgtag gtattagtaa cgcttactct     960
cacttctatg atggtttctc taaagtacca ttaaagatc aaagtgctgc actaggtgac    1020
tctctatatg gtgctgcatc tctaaatgat ttcggtattt tagctgtacg tgttgtaaac    1080
gatcacaatc caaccaaagt aacctctaaa atccgcgttt atcttaaacc taagcatatt    1140
agagtatggt gtcctcgccc acctcgagct gttgcttatt acggtcctgg agtagattac    1200
aaagatggca cactaactcc attaagcaca aaggacttga ccacttatta a             1251

<210> SEQ ID NO 5
<211> LENGTH: 11
<212> TYPE: PRT
<213> ORGANISM: Artificial Sequence
```

```
<220> FEATURE:
<223> OTHER INFORMATION: cholera non-toxic B subunit (CNTB) peptide 1

<400> SEQUENCE: 5

Ile Phe Ser Tyr Thr Glu Ser Leu Ala Gly Lys
1               5                   10

<210> SEQ ID NO 6
<211> LENGTH: 8
<212> TYPE: PRT
<213> ORGANISM: Artificial Sequence
<220> FEATURE:
<223> OTHER INFORMATION: CNTB peptide 2

<400> SEQUENCE: 6

Ile Ala Tyr Leu Thr Glu Ala Lys
1               5

<210> SEQ ID NO 7
<211> LENGTH: 7
<212> TYPE: PRT
<213> ORGANISM: Artificial Sequence
<220> FEATURE:
<223> OTHER INFORMATION: CNTB peptide 3

<400> SEQUENCE: 7

Leu Cys Val Trp Asn Asn Lys
1               5

<210> SEQ ID NO 8
<211> LENGTH: 13
<212> TYPE: PRT
<213> ORGANISM: Artificial Sequence
<220> FEATURE:
<223> OTHER INFORMATION: FVIII peptide 4

<400> SEQUENCE: 8

Phe Asp Asp Asp Asn Ser Pro Ser Phe Ile Gln Ile Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: FVIII peptide 5

<400> SEQUENCE: 9

Trp Thr Val Thr Val Glu Asp Gly Pro Thr Lys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: FVIII peptide 6

<400> SEQUENCE: 10

Tyr Tyr Ser Ser Phe Val Asn Met Glu Arg
1               5                   10

<210> SEQ ID NO 11
<211> LENGTH: 45
<212> TYPE: DNA
<213> ORGANISM: Artificial Sequence
```

<220> FEATURE:
<223> OTHER INFORMATION: forward primer

<400> SEQUENCE: 11
gggcccgggc cccggcgtaa acgctctgtt gggttaggtc agatg 45

<210> SEQ ID NO 12
<211> LENGTH: 27
<212> TYPE: DNA
<213> ORGANISM: Artificial Sequence
<220> FEATURE:
<223> OTHER INFORMATION: reverse primer

<400> SEQUENCE: 12
cgatctagat caatatgtgg tcagatc 27

<210> SEQ ID NO 13
<211> LENGTH: 4
<212> TYPE: PRT
<213> ORGANISM: Artificial Sequence
<220> FEATURE:
<223> OTHER INFORMATION: GPGP hinge region

<400> SEQUENCE: 13

Gly Pro Gly Pro
1

<210> SEQ ID NO 14
<211> LENGTH: 6
<212> TYPE: PRT
<213> ORGANISM: Artificial Sequence
<220> FEATURE:
<223> OTHER INFORMATION: furin cleavage site

<400> SEQUENCE: 14

Arg Arg Lys Arg Ser Val
1 5

<210> SEQ ID NO 15
<211> LENGTH: 4
<212> TYPE: PRT
<213> ORGANISM: Artificial Sequence
<220> FEATURE:
<223> OTHER INFORMATION: furin cleavage site

<400> SEQUENCE: 15

Arg Arg Lys Arg
1

<210> SEQ ID NO 16
<211> LENGTH: 42
<212> TYPE: DNA
<213> ORGANISM: Artificial Sequence
<220> FEATURE:
<223> OTHER INFORMATION: B domain sequence

<400> SEQUENCE: 16
tctttctctc aaaatccacc tgttttaaaa cgtcaccaac gc 42

<210> SEQ ID NO 17
<211> LENGTH: 30
<212> TYPE: DNA
<213> ORGANISM: Artificial Sequence
<220> FEATURE:
<223> OTHER INFORMATION: codon optimized GPGP-furin cleavage site

<400> SEQUENCE: 17
ggtcctggac cacgtcgtaa acgctctgtt                                30

<210> SEQ ID NO 18
<211> LENGTH: 10
<212> TYPE: PRT
<213> ORGANISM: Artificial Sequence
<220> FEATURE:
<223> OTHER INFORMATION: codon optimized GPGP-furin cleavage site

<400> SEQUENCE: 18

Gly Pro Gly Pro Arg Arg Lys Arg Ser Val
1               5                   10

<210> SEQ ID NO 19
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 19
gttcaacata gaagtcgtag cgaatctagt atcgagtcc                      39

<210> SEQ ID NO 20
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 20

Val Gln His Arg Ser Arg Ser Glu Ser Ser Ile Glu Ser
1               5                   10

<210> SEQ ID NO 21
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 21
ggccctctcc tcatctgc                                             18

<210> SEQ ID NO 22
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 22

Gly Pro Leu Leu Ile Cys
1               5

<210> SEQ ID NO 23
<211> LENGTH: 315
<212> TYPE: DNA
<213> ORGANISM: Artificial Sequence
<220> FEATURE:
<223> OTHER INFORMATION: IGF-1

<400> SEQUENCE: 23

```
ggaccggaga cgctctgcgg ggctgagctg gtggatgctc ttcagttcgt gtgtggagac    60
aggggctttt atttcaacaa gcccacaggg tatggctcca gcagtcggag ggcgcctcag   120
acaggcatcg tggatgagtg ctgcttccgg agctgtgatc taaggaggct ggagatgtat   180
tgcgcacccc tcaagcctgc caagtcagct cgctctgtcc gtgcccagcg ccacaccgac   240
atgcccaaga cccagaagga agtacatttg aagaacgcaa gtagagggag tgcaggaaac   300
aagaactaca ggatg                                                    315
```

<210> SEQ ID NO 24
<211> LENGTH: 315
<212> TYPE: DNA
<213> ORGANISM: Artificial Sequence
<220> FEATURE:
<223> OTHER INFORMATION: IGF-1, codon-optimized

<400> SEQUENCE: 24

```
ggtcctgaaa ctctatgtgg tgctgaattg gtagacgctt acaattcgt ttgtggcgat    60
cgtggtttct acttcaacaa acctaccggt tatggttcta gctctcgtcg cgcaccacaa   120
actggaattg tagatgagtg ttgctttaga agttgtgatc ttcgtcgcct tgaaatgtac   180
tgtgctcctt tgaaaccagc cggttctgct cgtagtgttg cagctcaagc tcataccgat   240
atgcctaaaa ctcagaagga agtacactta aaaaatgctt cccgaggttc tgctggaaac   300
aaaaattatc gtatg                                                    315
```

<210> SEQ ID NO 25
<211> LENGTH: 3801
<212> TYPE: DNA
<213> ORGANISM: Artificial Sequence
<220> FEATURE:
<223> OTHER INFORMATION: codon-optimized mutanase sequence

<400> SEQUENCE: 25

```
gcaggtggcc cgaatcttac tccaggtaaa ccaattactg ctagtggtca atctcaaacc    60
tatagccctc aaaatgtaaa agatggcaat caaaatactt actgggaaag tactaacaat   120
gccttccctc aatggattca agttgatttg ggtgcaagta ctggcattga tcaaattgtt   180
cttaagttac cagctagctg ggaagctcgt actcaaactc ttgctgttca aggtagtttg   240
aatggttcta ctttcactga tattgtaggt tctgcaaatt atgtattcag tccttctgta   300
ggtaataaca ctgttactat taattttacc gccacaagca cccgttatgt tcgcttgtac   360
gtaactgcga acactggttg gccagctgct caactgtctg aatttgaaat ttatggttct   420
ggtgaccaga ctcctgcacc tgatacttat caagctgaaa gtgctgcttt atctggtggc   480
gctaaagtaa atactgatca tgccggctac ataggtactg gttttgttga tggttattgg   540
actcaaggcg ctactactac cttttctgta acgcgcctta ctgctggtaa ttacgatgta   600
actctgaggt atggtaacgc aaccggcagt aataaaactg tatccttgta cgtaaatggc   660
gctaaaattc gtcaaacaac tttaccaagt ctacctaact gggattcatg gagtagcaag   720
actgaaactc ttaattttaaa tgctggtagc aacaccattg cttataaata cgaccctggc   780
gattctggta atgtaaatct tgatcaaatc actgtagaag catctacttc aactcctact   840
cctactccat ctcctactcc tacacctact ccaactccta ctcctactcc tactcctaca   900
ccaacaccta ctcctacccc aacccctact cctacaccta cacctacacc tactcctact   960
cctcctcctg gtggtaatat tgccataggc aaatctattt ccgcatctag tcacactcaa  1020
```

```
acttatgttg ctgagaacgc aaatgataac gatgtaaata cttactggga aggtggcggt    1080
aatcctagta ctttaacttt ggatcttggc gctaattata atattacttc tattgttcta    1140
aaactaaacc catcctctat atgggcagcc cgtactcaaa ctattcaagt tttgggccat    1200
gatcaaaata ctactacatt cagtaattta gtatctgcta aatcttactc tttcgatcct    1260
gcttctggta atactgttac cattccagtt accgctactg ttaaacgttt gcagttgaac    1320
attacttcta attccggtgc ccctgctggt caagtagctg agttccaagt tttcggtact    1380
cctgctccaa atcctgattt gactattacc ggtatgtctt ggtctccttc ttctccagtt    1440
gagacagatg caattactct gaatgctact gttaaaaaca atggtaatgc cagtgcagcc    1500
gctaccaccg taaatttcta cctaaataac gagctagctg ttctgctcc tgtagcagct    1560 ctagcggcag gcgcttctgc aactgttccg ctaaatgtag gtgctaaaac cgccgccaca    1620
tacgctgtag gtgctaaagt agatgaaagt aatgcagtaa ttgagttaaa cgagtctaac    1680
aatagctaca ctaatcctgc ttcattggtt gttgctccag ttagtagttc tgatttagtt    1740
ggcactgttt cttggactcc aagcactcct attgcaaaca atgctgtttc ttttaacgta    1800
aatcttaaaa atcaaggcac tattgcttct gccggtggtt ctcacggtgt tactgtagtt    1860
cttaaaaatg cttccggttc taccgttcaa actttcagtg gttcttacac cggtagtctt    1920
gctccgggag cttccgtaaa tattacccctt cctggtacct ggactgctgc tgctggtagc    1980
tatactgtaa ctgcaaccgt tgcggcagac gctaacgaac ttcctatcaa gcaagccaac    2040
aatgcaaaca cagcaagtct aaccgtatat tctgctcgtg gtgcaagcat gccatacagt    2100
cgttacgata ccgaggatgc cacccttggt ggtggcgcta ctctaaaatc cgctccgaca    2160
ttcgatcaag cgcttactgc atctgaagcc accggtcaat tgtacgctgc gttaccatct    2220
aacggctctt atcttcaatg gaccgtacgt caaggtcagg gtggtgcagg cgttactatg    2280
agatttacta tgccagattc tgctgacggc atgggcttaa acggtagttt agatgtttac    2340
gtaaacggta caaaagtaaa aaccgtatct ctaaccagtt actatagctg gcagtatttc    2400
tctggtgata tgccaggaga cgctccaagc gctggtcgtc ctttattccg ttttgatgaa    2460
gttcattgga aattagatac tcctttgaaa ccaggagata ctattcgcat acaaaagaac    2520
aacggtgata gcctagaata cggtgtagac tttattgaaa ttgaaccagt tcctgctgct    2580
atctctcgtc cggctaactc tgtttccgta actgattacg gtgctgttcc taacgatgga    2640
caggacgatc ttaccgcttt taaagcagcc gtaaacgcag ctgtagcatc cgataaaatc    2700
ttgtatattc cagaaggcac tttccacttg ggtaacatgt gggagattgg ttccgtaagt    2760
aacatgatcg atcacattac tattactgga gctggtattt ggtacactaa catccagttt    2820
accaacgcca atcctgcttc cggtggcatc tctctacgta ttactggtaa acttgatttc    2880
agcaacgttt acttgaactc taatttgcgt tctcgttatg gtcaaaatgc cgtttataaa    2940
ggttttatgg ataacttcgg taccaattcc gtaattcgtg acgtatgggt agaacacttc    3000
gaatgtggtt tctgggtagg tgattacggt catactcctg ctattcgcgc aagcggtctg    3060
ttaattgaaa acagccgaat ccgtaacaac ctagctgatg gtgtaaactt cgcccaaggt    3120
accagcaatt ctaccgtacg caacagcagc ttacgtaaca acggtgatga cgcccttgct    3180
gtatggacta gtaatactaa cggtgctcca gaaggcgtaa acaataccctt ctcttacaac    3240 accatcgaaa acaactggcg cgctggaggt attgccttct tcggaggaag cggacataag    3300
gccgatcaca actacatagt agattgtgta ggtggttctg gtatccgtat gaataccgtt    3360
ttcccaggat atcacttcca gaacaatacc ggtattgttt tctctgacac taccatagta    3420
```

```
aactgcggta ctagcaaaga tctatacaac ggtgaacgcg gtgctatcga tttggaagca    3480
tctaacgacg ccatcagaaa cgttactttt accaacatcg atattatcaa ctctcagcgc    3540
gatgctatcc agttcggtta tggtggtggt ttcaccaata tcgttttcaa caacatcaac    3600
attaacggaa ccggtcttga tggtgtaacc acctctcgtt tctctggacc tcatttaggc    3660
gcggcgatct tcacctatac cggtaacggt agtgctactt tcaacaattt acgcaccagc    3720
aatatcgctt atccaaattt atattatatc cagagcggtt tcaatttaat catcaataat    3780
catcatcacc atcaccacta a                                              3801
```

CODON OPTIMIZATION FOR INCREASING TRANSGENE EXPRESSION IN CHLOROPLASTS OF HIGHER SEED PLANTS

Cross-Reference to Related Applications

This Application is a §371 of International Patent Application No. PCT/US2017/023263, filed March 20, 2017, which claims the benefit of U.S. Provisional Application No. 62/310,788, filed Mar. 20, 2016. The entire disclosure of each of the aforesaid applications is incorporated by reference in the present application.

Government Support Clause

This invention was made with government support under grant numbers HL107904, HL109442, EY024564 awarded by the National Institutes of Health and grant number 1339130 awarded by the National Science Foundation. The government has certain rights in the invention.

FIELD OF THE INVENTION

This invention relates to improved transgene expression in chloroplasts through codon optimization using genomic, proteomic and ribosome profiling methods. Transgenes so improved and methods of use thereof are also provided.

BACKGROUND OF THE INVENTION

Several publications and patent documents are cited throughout the specification in order to describe the state of the art to which this invention pertains. Each of these citations is incorporated herein by reference as though set forth in full.

A major limitation in clinical translation of human therapeutic proteins in chloroplasts is their low level expression. Prokaryotic or shorter human genes are highly expressed (up to 70% of total leaf protein) in chloroplasts. For example, native prokaryotic genes from *Bacillus anthracis* and *Bacillus thuringiensis* were expressed up to 29.4% and 45.3%, respectively, of the total soluble protein (TSP) in chloroplasts (De Cosa et al., 2001; Ruhlman et al., 2010). Small human genes including insulin like growth factor-1 (~7.8 kDa, Daniell et al., 2009), proinsulin (~12 kDa, Ruhlman et al., 2010), and interferon-α2b (~21.5 kDa, Arlen et al., 2007) were expressed in chloroplasts at very high levels. However, expression of larger human proteins presents a major challenge.

Likewise, expression of viral vaccine antigens is quite unpredictable with high, moderate or extremely low expression levels. For example, due to their susceptibility to proteolytic degradation at the N-terminal region, VP6 antigen of rotavirus accumulated at very low levels in tobacco chloroplasts (Birch-Machin et al., 2004; Inka Borchers et al., 2012). The expression level of human papillomavirus-16 L1 antigen varied from 0.1% to 1.5% and accumulated up to 2% when fused with LTB but extremely low when fused with glutathione-S-transferase (GST) in tobacco chloroplasts (Lenzi et al., 2008; Waheed et al., 2011a; Waheed et al., 2011b; Hassan et al., 2014). Further, the instability of chloroplast-derived antigens against human immunodeficiency virus type 1 (HIV-1) has been reported in tobacco. Chloroplast-derived p24 protein only accumulated ~2.5% in youngest leaves and was not detectable in mature leaves when native p24 cDNA was expressed (McCabe et al., 2008). It is well known that high doses of vaccine antigens stimulate high level immunity and confer greater protection against pathogens and therefore higher level expression in chloroplasts is a major requirement (Chan and Daniell, 2015).

Such challenges have been addressed by the use of optimal regulatory sequences (promoters, 5' and 3'UTRs), especially species specific endogenous elements (Ruhlman et al., 2010). Cursory attempts have been made to simply increase AT content by modifying third position of each codon of human genes (Daniell et al., 2009). In vitro assay of inserted gene for translation efficiencies of several synonymous codons are not always correlated with codon usage in plastid mRNAs (Nakamura and Sugiura, 2007) but have been used in the past codon optimization studies (Ye et al., 2001; Lenzi et al., 2008; Jabeen at al., 2010) because there are no such in vivo studies. Therefore, no systematic study has been done to utilize extensive knowledge gathered by sequencing several hundred chloroplast genomes to understand codon usage and frequency of highly expressed chloroplast genes. Another major challenge is the lack of reliable methods to quantify insoluble proteins because the only reliable method (ELISA), can't be used due to aggregation or formation of multimeric structures. Targeted Proteomic Quantification by Mass Spectrometry by parallel reaction monitoring (PRM) has become a powerful tool for relative and absolute protein quantitation based on its specificity and sensitivity (Domon and Aebersold, 2010; Gallien et al., 2012). In addition, PRM offers high specificity and multiplexing characteristics which allow specific monitoring of multiple fragment ions of peptides, based on nanoLC retention times and precursor ion m/z (Gallien et al., 2012) but this concept has never been tested for plant protein drugs.

Drawbacks associated with expression of live attenuated and killed viruses include the potential to revert to virulence, low levels of immunogenicity, antigenic variability between species, and possible transfer of genetic materials to wild-type strains (Burns et al., 2014). An outbreak of type 2 vaccine-derived polio (VDVP2) in Nigeria, first detected in 2006, became endemic in Africa and persists today (Famulare et al., 2015). This large poliomyelitis outbreak associated with type 2 circulating vaccine-derived poliovirus (cVDPV2) has occurred since 2005 in northern Nigeria; phylogenetic analysis of P1/capsid region sequences of isolates from each of the 403 cases reported in 2005 through 2011 resolved the outbreak into 23 independent VDPV2 emergences, at least 7 of which established circulating lineage groups (Burns et al., 2013). Non-polio enteroviruses (NPEVs) associated with acute flaccid paralysis (AFP) cases have been reported frequently through Polio Surveillance Programs (PSPs) worldwide (Laxmivandana et al., 2013). Although wild polio cases have been eradicated in many countries due to intensive oral polio vaccination programs, more non-polio AFP cases are being reported worldwide. Currently recognized EV species have been divided into poliovirus (PV) containing the three PV serotypes and human enterovirus (HEV) A, B, C and D (Dhole et al., 2009). Based on phylogenetic analysis of their genomes, PV and serotypes of the HEV-C species are closely related (Brown et al., 2003). Further, the high frequency of circulation of HEV species C has led to reports of vaccine-derived poliovirus (VDPV) outbreaks (Rakoto-Andrianarivelo et al., 2005). Between 2005 and 2011, 23 lineages of circulating vaccine-derived polioviruses (cVDPVs) with origins in the nonstructural region (NSR) of non-polio enterovirus C (NPEV-C) origin were detected in Nigeria. Thus, recombination between Sabin oral poliovirus vaccine (OPV)

and indigenous NPEV-Cs led to some of the recombinant cVDPV lineages isolated during the outbreak in Nigeria (Adeniji et al., 2015). The cVDPVs are largely generated by homologous recombination between OPV and HEV-C and caused numerous outbreaks of poliomyelitis globally, becoming a serious health threat (Jiang et al., 2007). Due to recombination of OPV with HEV-C, highly virulent cVDPVs have the risk to replace wild-type PVs in regions with low vaccine coverage. In an effort for global PV eradication, worldwide cessation of OPV vaccination has been proposed to minimize the number of vaccine-derived poliovirus strains that could lead to new outbreaks (Kouiayskaia et al., 2015; Parker et al., 2015).

Plant-derived subunit vaccines are heat-stable and are free from contamination with animal pathogens. They can also be engineered to contain multiple antigens and transmucosal carrires, to protect against multiple infectious diseases (Chan et al., 2015). Recent report of intact plant cells expressing green fluorescent protein (GFP) between villi of the ileum after oral delivery provided direct evidence for protection of protein drugs in the digestive system from acids and enzymes in the stomach; GFP fused with the transmucosal carrier CTB released into the gut lumen from plant cells was absorbed by epithelial cells via GM1 receptor mediated delivery (Xiao et al., 2015). Such mechanistic and conceptual advances could revolutionize vaccine delivery by eliminating the cost of complex production systems, such as fermentation, purification, cold storage and transportation (Jin et al., 2015 and Kwon et al., 2013. Although potato-derived HBsAg expressed via the nuclear genome was tested in pre-clinical and in human clinical trials a decade ago, (Kong et al., 2001; Thanavala et al., 2005) progress in advancing to later stages is slow. Two major challenges are the low levels of expression of antigens via the nuclear genome and the potential to induce tolerance without injectable priming of antigens with adjuvants (Chan et al., 2015; Rybicki et al, 2014).

SUMMARY OF THE INVENTION

In accordance with the present invention, a method for increasing translation of a transgene encoding a protein of interest in a chloroplast is provided. An exemplary method comprises analyzing the native sequence of a nucleic acid encoding said protein of interest and replacing codons in said sequence with those preferentially used in psbA genes in chloroplasts across over 100 plant species and optionally performing ribosome profiling and removing any codons that cause stalling of ribosomes during translation. A synthetic, codon optimized sequence is then produced and cloned into a chloroplast transformation vector, said synthetic sequence being operably linked to 5' and 3' regulatory elements for suitable for expression in said chloroplast. Target plants are then transformed with this vector under conditions whereby said therapeutic protein is expressed, wherein replacing said codons causes at least a two fold, three fold, four fold, five fold, 20 fold or 40 fold increase in protein expression relative to expression levels observed using the native sequence. The method can optionally entail isolating said protein of interest. In a preferred embodiment, the method further comprises harvesting and lyophilizing leaves from said plant, wherein the lyophilized leaves comprising the protein of interest.

In particularly preferred embodiments, synthetic VP1 protein is produced that can be used to advantage in vaccines for the treatment of polio. Accordingly, a method of producing systemic and mucosal immunity in a subject who has been previously immunized against polio virus comprising orally administering the lyophilized plant cells described above to said subject in the presence of an adjuvant, said administration causing production of anti-VP1-IgG1 and anti-VP-1-IgA titers in said subject, thereby boosting immunity to said polio virus is provided.

In another embodiment, Factor VIII heavy and light chains have been codon optimized. Factor VIII so produced can be used to advantage in methods for the treatment of coagulation disorders. Thus, the invention also provides for methods for the treatment of coagulation disorders using coagulation factors optimized for efficient expression as disclosed herein. While FVIII is exemplified herein, other coagulation factors, such as FIX, FX, and FVII can readily be optimized using the guidance provided herein.

The methods of the invention can also be used to advantage to produce synthetic insulin growth factor (IGF-1). Methods of treatment of IGF-1 deficiencies using the synthetic IGF-1 described herein are also within the scope of the invention.

In yet another embodiment, a synthetic mutanase enzyme is provided. Methods for treating dental caries using synthetic mutanase enzymes are also disclosed.

In another aspect of the invention, a method of producing systemic and mucosal immunity in a subject who has been previously immunized against polio virus comprising orally administering the lyophilized plant cells described above to said subject in the presence of an adjuvant, said administration causing production of anti-VP1-IgG1 and anti-VP-1-IgA titers in said subject, thereby boosting immunity to said polio virus.

Also within the scope of the invention are plastid transformation vectors encoding the synthetic proteins described herein. Plants comprising such vectors also form an aspect of the invention. In a preferred embodiment, the plant is edible.

BRIEF DESCRIPTION OF THE DRAWINGS

FIG. 1: Development of algorithm of codons optimized for expression of heterologous genes in plant chloroplasts. Process of development of codon optimization algorithm. Sequence data of psbA genes from 133 plant species collected from NCBI and analyzed for codon preference. A codon optimizer was developed using Java programming language and the codon preference table shown generated. Codon preference is indicated by percentage of use for each amino acid.

(FIG. 2A) Schematic diagram of vector construct containing CTB-FVIII single, heavy and light chain expression cassette. Prrn, rRNA operon promoter; aadA, aminoglycoside 3'-adenylytransferase gene; PpsbA, promoter and 5'-UTR of psbA gene; CTB, coding sequence of cholera non-toxic B subunit; FVIII $SC^C$, a fusion form of codon-optimized FVIII heavy chain (HC including 14 amino acids from B domain) and light chain (LC); TpsbA, 3'-UTR of the psbA gene; trnI, isoleucyl-tRNA; trnA, alanyl-tRNA. Southern blot probe (SB-P) was generated by digestion of pUC-LSLF with BamHI and genomic DNA from transplastomic plants was digested by HindIII. (FIG. 2B) Western blot assay for expression of native or codon-optimized sequences for HC, LC and SC in E. coli. Total proteins were extracted from E. coli transformed with chloroplast expression vectors containing native or codon-optimized sequences for FVIII HC, LC and SC. Proteins were loaded as indicated and probed with anti-CTB antibody (1 in 10,000). The transformed and untransformed (UT) E. coli were incubated in Terrific Broth (TB) media supplemented with ampicillin (50 µg/ml) at 37° C. overnight. Arrows indicate proteins expected in corresponding sizes (CTB-FVIII HC, 100 kDa; CTB-FVIII LC, 92 kDa and CTB-FVIII SC, 179 kDa) (FIG. 2C) PCR analysis for the integration of CTB-FVIII LC and SC expression cassette. Specific sets of primers as indicated in A were used for amplification of DNA fragments and resolved on 1% agarose gel. UT, untransformed wild type gDNA; S1~S3, three independent FVIII SC transplastomic lines; L1-L8, eight independent FVIII LC transplastomic linges. (FIG. 2D) Southern blot analysis for CTB-FVIII SC$^C$. Total lettuce genomic DNA (3 µg) was digested with HindIII and separated on a 0.8% agarose gel and blotted onto a Nytran membrane. UT, untransformed wild type plant; 1~4, four independent $2^{nd}$ round transplastomic lines. (FIG. 2E) Sequences codon-optimized FVIII single chain. HC, FVIII heavy chain composed of A1 and A2 domains (SEQ ID NO: 1); LC, FVIII light chain composed of A3, C1 and C2 domains. SEQ ID NO: 2) CTB: native sequence of cholera non-toxic B subunit (SEQ ID NO: 3).

FIGS. 3A-3C. Confirmation of homoplasmic lines using Southern blot and quantification of proteins expressed in the homoplasmic transplastomic plant lines. (FIG. 3A and FIG. 3B) Southern blot analysis for CTB-FVIII LC$^C$ and CTB-FVIII SC$^C$. Total lettuce genomic DNA (3 µg) was digested with HindIII and separated on a 0.8% agarose gel and blotted onto a Nytran membrane. UT, untransformed wild type plant; L1-L8 and S1-S4, eight and four independent $2^{nd}$ round transplastomic lines for CTB-FVIII LC$^C$ and CTB-FVIII SC$^C$, respectively. (FIG. 3C) Four micrograms of total leaf proteins (10 mg in 500 µl extraction buffer) extracted lyophilized transplastomic lettuce leaves expressing CTB-FVIII HC$^C$, CTB-FVIII LC$^C$ and CTB-FVIII SC$^C$ were loaded as indicated and resolved on 8% SDS-PAGE. Anti-CTB antibody (1 in 10000) was used to probe the CTB fused FVIII proteins. UT, untransformed wild type (UT); Co, codon-optimized sequence. CTB standards were loaded as indicted for quantification and the calculated quantification results (m/mg) were indicated below each batch. The transplastomic lettuce plants expressing CTB-FVIII HC$^C$ and LC$^C$ were grown and harvested in a greenhouse at University of Pennsylvania and CTB-FVIII SC$^C$ lettuce plants were germinated and grown in hydroponic cultivation system at Fraunhofer cGMP facilities and the leaves were harvested in a monthly basis.

(FIG. 4A) Tobacco and lettuce chloroplast transformation vectors containing CTB-VP1 expression cassettes. Prrn, rRNA operon promoter; aadA, aminoglycoside 3'-adenylytransferase gene; PpsbA, promoter and 5'-UTR of psbA gene; CTB, coding sequence of non-toxic cholera B subunit; VP1, coding sequence for polio virus VP1 gene (SEQ ID NO: 4); TpsbA, 3'-UTR of psbA gene; trnI, isoleucyl-tRNA; trnA, alanyl-tRNA Total leaf proteins were extracted from lettuce (FIG. 4B) or tobacco (FIG. 4C) were loaded at indicated concentrations and resolved on gradient (4%-20%) SDS-PAGE. FIG. 4D. Total protein extracted from wild type (WT), native CTB-VP1 (N) and codon-optimized CTB-VP1 (CO) tobacco plants were probed with anti-CNTB antibody. CNTB was loaded as standard for quantification.

FIG. 6A-6C: PRM mass spectrometry analysis of CNTB-FVIII and CNTB-VP1 proteins at N- to C-terminal protein sequences. Exe-y represents measured peptide molarity (fmol on column) of peptides from CTB-F8 HC in codon optimized or native genes. FIG. 6A. CNTB: peptide 1, IFSYTESLAGK (SEQ ID NO: 5); peptide 2, IAYLTEAK (SEQ ID NO: 6); peptide 3, LCVWNNK (SEQ ID NO: 7). FIG. 6B. FVIII peptide: peptide 4, FDDDNSPSFIQIR (SEQ ID NO: 8); peptide 5, WTVTVEDGPTK (SEQ ID NO: 9); peptide 6, YYSSFVNMER (SEQ ID NO: 10). FIG. 6C. CNTB: peptide 1, IFSYTESLAGK (SEQ ID NO: 1); peptide 3, LCVWNNK (SEQ ID NO: 3); peptide 2, IAYLTEAK (SEQ ID NO: 5). Median of 4 technical replicates is represented in each sample.

FIG. 8A-C: Ribosome profiling data from transplastomic plants expressing native and codon-optimized VP1 or F8 HC. Read coverage for the native (N) transgenes, the codon-optimized (CO) transgenes and the endogenous psbA and rbcL genes are displayed with the Integrated Genome Viewer (IGV). FIG. 8A. Data from tobacco leaves expressing the native and codon-optimized VP1 transgenes. Asterisks mark each pair of consecutive alanine codons in the data from the native line. The + symbol marks three consecutive alanine codons. Many strong ribosome pause sites in the plants expressing native VP1 map to paired alanine codons, whereas this is not observed in the codon-optimized line. Triangles mark each pair of consecutive serine codons in the codon-optimized line. A major ribosome stall maps to a region harboring five closely spaced serine codons in the codon-optimized VP1 gene. FIG. 8B. Data from lettuce plants expressing the native and codon-optimized F8 HC transgenes. A major ribosome stall in the native FB HC gene maps to a pair of adjacent CTC leucine codons, a codon that is not used in the native psbA gene. Ribosome footprint coverage is much more uniform on the codon-optimized transgene. FIG. 8C. Absolute and relative ribosome footprints counts.

FIG. 9A. Southern blot analysis of native and codon-optimized CTB-VP1 transplastomic tobacco lines. AflIII-digested wild type (WT) and transformed (line 1, 2, 3 and 4) genomic DNA was probed with DIG-labeled flanking sequence digested with BamHI/BglII. FIG. 9B. Tobacco and lettuce chloroplast transformation vectors containing CTB-VP1 expression cassettes. Prrn, rRNA operon promoter; aadA, aminoglycoside 3'-adenylytransferase gene; PpsbA, promoter and 5'-UTR of psbA gene; CTB, coding sequence of non-toxic cholera B subunit; VP1, coding sequence for polio virus VP1 gene; TpsbA, 3'-UTR of psbA gene; trnI, isoleucyl-tRNA; trnA, alanyl-tRNA; FIG. 9C. Southern blot analysis confirming site specific integration of the transgene into the chloroplast. FIG. 9D. Western blot analysis of CTB-VP1 in two independent lettuce transplastomic lines and wild type (WT) controls.

FIG. 10. Stability of CTB-VP1 produced in transplastomic lines. The intact monomer band of CTB-VP1 fusion proteins was observed without any detectable degradation of CTB-VP1 in all tested lyophilized samples after storage for 4 and 8 months at ambient temperature. Formation of pentameric structures of the CTB-VP1 expressed in chloroplasts was evaluated using GM1 binding ELISA assays, both native and codon-optimized fresh and lyophilized CTB-VP1 from tobacco showed comparable absorbance to CTB (positive control), whereas no signals were detected from wild type plants or BSA (negative controls).

FIGS. 11A-11J: Evaluation of serum VP1-IgG1 and VP1-IgA antibody titers after oral or subcutaneous vaccination. Antibody responses of mice primed with IPV and boosted with either IPV or plant-made native or codon-optimized VP1 adjuvanted with saponin and/or squalene. Plates were coated with purified VP1 protein (10 m/m1) and probed with sera samples (2 or 4 weeks after boosting) followed by HRP-conjugated rat-anti-mouse IgG1 (1:1000) (BD) or HRP-conjugated goat-anti-mouse IgA (1:5000) (American Qualex). (FIG. 12A-F) VP1-IgG1 antibody titers at different time points: (FIG. 12A-D) weekly boosts and sera samples collected on days 0, 29, 43 and 57; (FIG. 12E, F) monthly boosts and samples collected on days 87 and 117; (FIG. 12G-J) VP1-IgA antibody titers at different time points: (FIG. 12G-I) weekly boosts and sera samples collected on days 0, 29 and 43; (FIG. 12J) monthly boosts with sera samples collected on day 117. Group 1: untreated; Group 2: prime and boost with IPV; Group 5: IPV prime, boost with native VP1 protein with adjuvant (saponin/squalene); Group 8: IPV prime, boost with codon-optimized VP1 protein with adjuvant (saponin/squalene); Group 9: boosted with codon-optimized VP1 adjuvanted with both saponin and squalene but without IPV priming. Statistical analysis by Student's t-test (GraphPad Prism version 6). $P<0.05$, *$P<0.01$, ****$P<0.001$ are shown.

FIGS. 12A-12C: Determination of poliovirus neutralizing titers against poliovirus Sabin 1, 2 and 3 strains. Virus-neutralizing antibody titers from mice (n=10/group) orally boosted with native or codon-optimized CTB-VP1 antigens adjuvanted with saponin only (groups 3 and 6), squalene only (groups 4 and 7) or both (groups 5, 8 and 9); mice primed and boosted with IPV (group 2); and untreated mice. Individual titers for each mouse were plotted, and the bar represents the mean neutralizing titer±SEM. The serum dilution of a reciprocal titer at which no virus neutralization was detected was recorded as the $\log_2$ (titer) of 2.5. Poliovirus-neutralizing antibodies against all three Sabin strains, (FIG. 12A) Sabin 1, (FIG. 12B) Sabin 2, and (FIG. 12C) Sabin 3$P<0.05$, *$P<0.01$, ****$P<0.001$ are indicated in the graph using Student's t-test (GraphPad Prism version 6).

FIGS. 13A-13E: Seropositivity rate of Sabin 1, 2 and 3 neutralizing titers after subcutaneous IPV or oral VP1 boosting. The seropositivity rate of poliovirus-neutralizing antibodies as determined by the number of mice with seroprevalence (neutralizing antibody $\log_2$(titer)≥3) with the total number of mice in each group boosted with the native or codon-optimized CTB-VP1 (Groups 3-9), or, IPV prime/boost (Group 2), at day 1 and day 30. The seropositivity rate of neutralizing titers against Sabin strains 1, 2 and 3 (FIG. 13A-C) and all three Sabin types (FIG. 13D) are shown. FIG. 13E. Conclusion of seropositivity rate (%). , $P<0.05$, *, $P<0.01$, ****, $P<0.001$ as indicated in the graph using Student's t-test (GraphPad Prism version 6).

FIGS. 14A-14C. Construction of codon-optimized synthetic IGF-1 fused to native CTB into tobacco chloroplast transformation vector (pLD-utr) and confirmation of its expression in *E. coli*. (FIG. 14A) Schematic diagram of chloroplast transformation vector map containing CTB-IGF-1 expression cassette. Prrn, rRNA operon promoter; aadA, aminoglycoside 3'-adenylytransferase gene; PpsbA, promoter and 5'-UTR of psbA gene; CTB, coding sequence of native cholera non-toxic B subunit; IGF-1($C^N$), codon-optimized human insulin-like growth factor 1 (105 amino acids included with 35 amino acids for Ea peptide); TpsbA, 3'-UTR of the psbA gene; trnI, isoleucyl-tRNA; trnA, alanyl-tRNA. (FIG. 14B) Immunoblot assay for the expression of codon-optimized sequences for IGF-1 in *E. coli*. Total proteins were extracted from transformed *E. coli* with chloroplast expression vectors containing two codon-optimized sequences (C°, codon-optimized old; $C^N$, codon-optimized new) for IGF-1. Proteins were loaded on 12% SDS-PAGE as indicated and probed with anti-CTB antibody (1 in 10,000). Fold difference of expression between two synthetic sequences ($C^O$ and $C^N$) were calculated using Image J. The transformed and untransformed (UT) *E. coli* were incubated in Luria-Bertani (LB) media supplemented with ampicillin (50 μg/ml) at 37° C. overnight. Arrow indicates expected proteins in size (CTB-IGF-1, 24.3 kDa) (FIG. 14C) Southern blot analysis of CTB-IGF-1 transplastomic lines. Genomic DNA from the transplastomic plants was digested with AflII and 0.81 kb of Southern blot probe (SB-P) region was used as probe after generated by digestion of pUC-ctv with BamHI and BglII.

FIGS. 15A-15D. Quantification and functional analysis of CTB-IGF-1 in transplastomic lines. Western blot analysis of lyophilized CTB-IGF-1 transplastomic line against anti-CTB (FIG. 15A) and anti-IGF-1 (FIG. 15B). Lane 1, 2 ng; 2, 4 ng; 3, 8 ng of cholera toxin B subunit (CTB); 1-1, 2 ng; 2-1, 4 ng; 3-1, 8 ng of human insulin-like growth factor-1 (IGF-1); 4, 0.1 ug; 5, 0.2 ug; 6, 0.4 ug of CTB-IGF-1 lyophilized leaf homogenate. Approximately 24.3 kDa of CTB-IGF-1 protein were indicated as arrows. (FIG. 15C) Immunoblot evaluation of total leaf protein from fresh and lyophilized CTB-IGF-1. Equal amount of fresh and lyophilized leaves were extracted in the same volume of extraction buffer, then they were loaded in a serial dilution. The arrow indicates expected size of CTB-IGF-1. (FIG. 15D) ELISA assay of CTB-IGF-1 pentamer forms against GM1 receptors. BSA and GM1 are used as negative controls.

FIGS. 16A-16D. Activity assay of plant derived IGF-1. (FIG. 16A) Cell-based assays on phosphorylation of IGF-1 receptor by CTB-IGF-1. P-IGFR indicates phosphorylated IGF-1 receptor and GAPDH/Akt were used as controls. The top is dose dependent phosphorylation and the bottom shows time dependent phosphorylation. (FIG. 16B) The amount of circulating Pro-IGF-1 in mice (n=3) serum dependent on time post gavage. (FIG. 16C) The amount of glucose in blood depending on time post gavage. Plant-GFP was utilized as a control in the same amount of plant derived CTB-IGF-1. (FIG. 16D) Detected IGF-1 in serum and muscle tissue after plant derived CTB-IGF-1 gavage. Plant- GFP was used as a gavage control and GAPDH was a positive control in muscle tissue.

FIGS. 17A-17F. Proliferation assay of human and/or mouse cells by purified CTB-IGF-1 (FIG. 17A) Purification of CTB-IGF-1 from tobacco transplastomic lines. C, comassie blue staining of CTB-IGF-1 after purification; W, western blot assay against CTB antibody. The arrow indicates approximately 24.3 kDa of CTB-IGF-1. (FIG. 17B) Forty-eight hours after incubation of HOK (Human Oral Keratinocytes) with a series concentration of IGF-1 peptide and purified CTB-IGF-1 from plants. Eighteen hours after 2,500 HOK cells were seeded, they were incubated with IGF-1 and purified CTB-IGF-1 for 48 hours. Density of viable cells was measured by MTT assay at absorbance 570. IGF-1 peptide was utilized as a positive control. (FIG. 17C) Relative absorbance of GMSC (Human Gingiva derived Mesenchymal Stromal Cells) in a CTB-IGF-1 dose dependent manner. Four-thousand of GMSC cells were seeded and the viable cells were measured after 24 hours incubation with CTB-IGF-1 and IGF-1 as a control. (FIG. 17D) Absorbance of viable SCC (Human head and neck Squamous Carcinoma Cells) was measured after 48 hours incubation with IGF-1 and CTB-IGF-1. Three-thousand of SCC were seeded for the incubation. (FIG. 17E) CTB-IGF-1 dose dependent relative absorbance of MC3TC (Mouse Osteoblast Cells) after 24 hours incubation. Four-thousand of MC3TC were seeded. (FIGS. 17B-17E) This is each representative of the data obtained from two biological repeats run in triplets. (FIG. 17F) Sequence alignments of native (Nat, SEQ ID NO: 23) and codon-optimized (Co, SEQ ID NO: 24) IGF-1 genes. Optimized codons are marked in yellow. Nat: native sequence; Co: codon-optimized sequence. To avoid glycosylation $Lsy^{68}$ (AAG), $Arg^{74}$ (CGT) and $Arg^{77}$ (CGC) were changed to $Gly^{68}$ (GGT), $Ala^{74}$ (GCA) and $Ala^{77}$ (GCT), which are marked in red.

FIGS. 18A-18 F. Construction of codon Construction of codon-optimized mutanase sequence from *Paenibacillus* sp. Strain RM1 into chloroplast transformation vector. Protegrin was added to the 5' end and His tag was added to the 3'end. FIG. 18A: Vector construction providing optimized mutanase coding sequence (SEQ ID NO: 25). FIG. 18B: Mutanase gene was codon optimized based on the codon frequency of psbA gene. This table showing the codon frequency of native and codon optimized Mutanase sequence. FIG. 18E. Results of a mutanse assay are shown.

DETAILED DESCRIPTION OF THE INVENTION

Figure 2A:
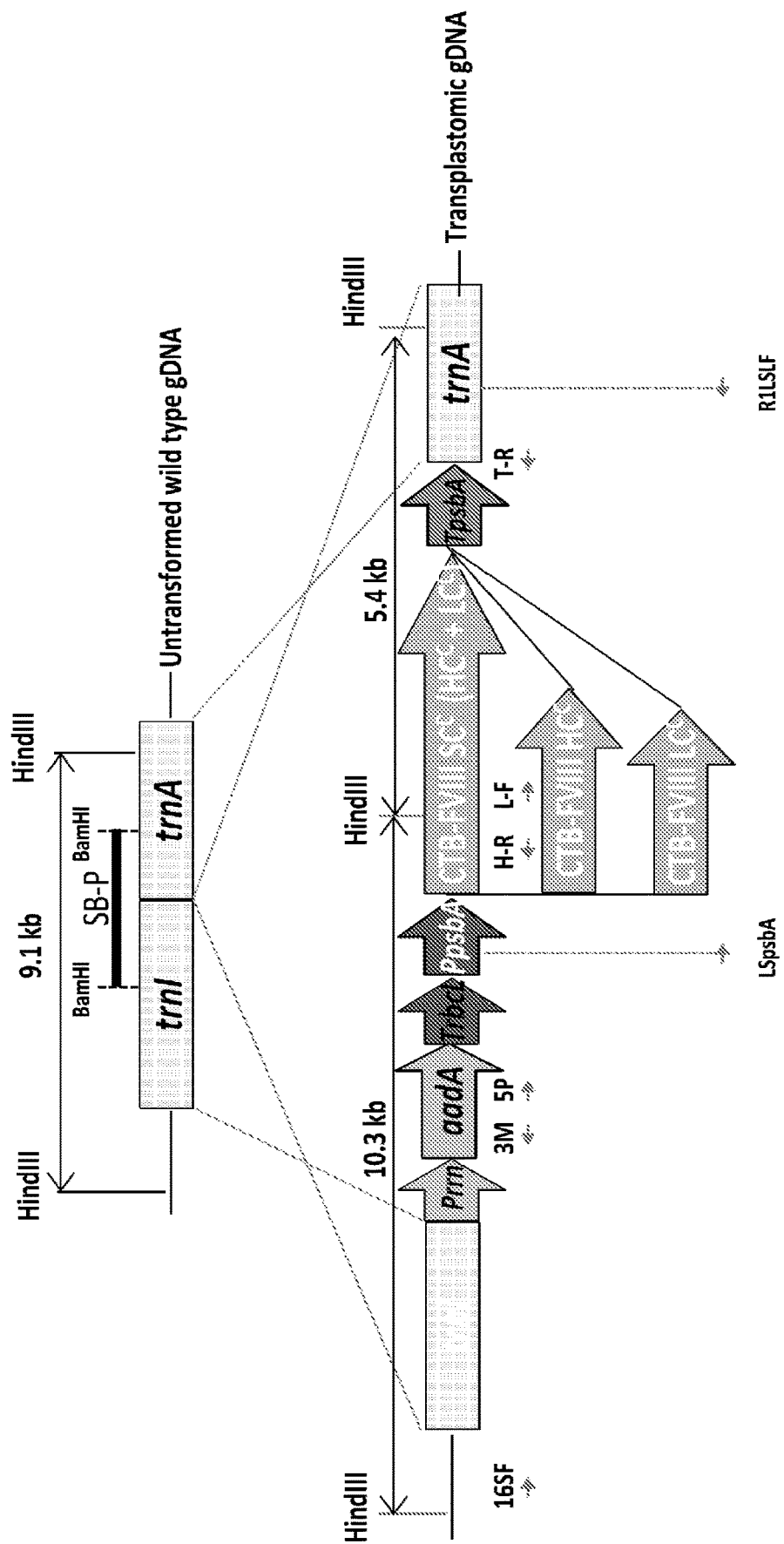
FIGS. 2A-2E. Construction of codon-optimized synthetic FVIII single, heavy and light chain gene into lettuce chloroplast transformation vector, and confirmation of its expression in E. coli and homoplasmic lines by PCR.

In the present invention, heterologous gene expression utilizing chloroplast genome sequences, ribosome profiling and targeted proteomic quantification by mass spectrometry or parallel reaction monitoring (PRM) was employed to develop methods for increasing translation of heterologous proteins of interest in chloroplasts. Codon optimization based on psbA genes from 133 plant species increased translational efficiencies of heavy chain of the human clotting factor VIII (FVIII) and polio viral capsid protein 1 (VP1), when compared with corresponding native genes, driven by identical psbA regulatory sequences. PRM analysis using peptides from N or C terminus showed 5-7 or 22-28 fold increase in FVIII or VP1 codon optimized genes. Western blot analysis of the same batch of materials showed either lower or higher quantitation, underscoring some limitations. PRM is validated here for the first time for quantitation of biopharmaceuticals in plant cells, especially useful for insoluble or multimeric proteins. Despite prokaryotic origin, codon usage is different between *E. coli* and chloroplasts. Northern blots confirmed that the increase of codon-optimized protein synthesis is at the translational level rather than any impact on transcript abundance or stability. Ribosome foot prints did not increase proportionately with VP1 translation or even decreased after FVIII codon optimization but is useful in diagnosing rate limiting steps. A major ribosome pause at CTC leucine codons in the native gene was eliminated upon codon optimization. Ribosome stalls were observed at clusters of serine codons in the codon-optimized VP1 gene. Synthetic sequences which eliminate CTC leucine clusters further optimizes such sequences.

The WHO's Strategic Advisory Group of Experts recommended complete withdrawal of OPV2 in 2016 globally, replacing with at least one dose of IPV. However, high cost, limited supply of IPV, persistent cVDPV transmission and need for subsequent boosting remain unresolved. The strategy of using a low cost cold-chain free plant-made viral protein 1 (VP1) subunit vaccine as an oral booster after single IPV priming is a novel solution to address this critical need. Oral boosting of VP1 bioencapsulated in plant cells resulted in high VP1-IgG1, IgA and neutralizing antibody titers (~3.17-10.17 log 2 titer) against all three poliovirus Sabin serotypes. Ability to store lyophilized plant cells expressing VP1 at ambient temperature indefinitely without loss of efficacy eliminates cold chain currently required for all vaccines. These findings provide evidence for plant-made booster vaccine to replace OPV or boost immunity among the elderly population with waning immunity for immunizations received early in life.

Definitions

It is to be understood that both the foregoing general description and the following detailed description are exemplary and explanatory only and are not intended to limit the scope of the current teachings. In this application, the use of the singular includes the plural unless specifically stated otherwise. For example, "at least one" means that more than one can be present. Also, the use of "comprise", "contain", and "include", or modifications of those root words, for example but not limited to, "comprises", "contained", and "including", are not intended to be limiting and means "including the following elements but not excluding others."

The term "consists essentially of," or "consisting essentially of," as used herein, excludes other elements from having any essential significance to the combination. Use of "or" means "and/or" unless stated otherwise. The term "and/or" means that the terms before and after can be taken together or separately. For illustration purposes, but not as a limitation, "X and/or Y" can mean "X" or "Y" or "X and Y".

As used herein, the terms "administering" or "administration" of an agent, drug, or peptide to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the terms "disease," "disorder," or "complication" refers to any deviation from a normal state in a subject.

As used herein, by the term "effective amount" "amount effective," or the like, it is meant an amount effective at dosages and for periods of time necessary to achieve the desired result.

As used herein, the term "inhibiting" or "treating" means causing the clinical symptoms of the disease state not to worsen or develop, e.g., inhibiting the onset of disease, in a subject that may be exposed to or predisposed to the disease state, but does not yet experience or display symptoms of the disease state.

As used herein, the term "CTB" refers cholera toxin B subunit. Cholera toxin is a protein complex comprising one A subunit and five B subunits. The B subunit is nontoxic and important to the protein complex as it allows the protein to bind to cellular surfaces via the pentasaccharide chain of ganglioside.

A "replicon" is any genetic element, for example, a plasmid, cosmid, bacmid, phage or virus, that is capable of replication largely under its own control. A replicon may be either RNA or DNA and may be single or double stranded.

A "vector" is any vehicle to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "promoter region" refers to the 5' regulatory regions of a gene (e.g., 5'UTR sequences (e.g., psbA sequences, promoters (e.g., universal Prnn promoters or psbA promoters endogenous to the plants to be transformed and optional enhancer elements.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The term "selectable marker gene" refers to a gene that when expressed confers a selectable phenotype, such as antibiotic resistance, on a transformed cell or plant. Selectable markers useful in plastid transformation vectors include, without limitation, those encoding for spectinomycin resistance, glyphosate resistance, BADH resistance, and kanamycin resistance.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "DNA construct" refers to a genetic sequence used to transform plants and generate progeny transgenic plants. These constructs may be administered to plants in a viral or plasmid vector. However, most preferred for use in the invention are plastid transformation vectors. Other methods of delivery such as *Agrobacterium* T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

As used herein, the term "chloroplast" includes organelles or plastids found in plant cells and other eukaryotic organisms that conduct photosynthesis. Chloroplasts capture light energy to conserve free energy in the form of ATP and reduce NADP to NADPH through a complex set of processes called photosynthesis. Chloroplasts contain chlorophyll. Chloroplasts have a higher copy number and expression levels of the transgene. Each chloroplast may contain up to 100 genomes, while each plant cell may contain up to 100 chloroplasts. Therefore, each plant cell may contain as many as 100000 chloroplast genomes which results in high expression levels of proteins expressed via the chloroplast genome. Chloroplasts further offer gene containment through maternal inheritance as the chloroplast genome is not transferred through pollen unlike nuclear genomic DNA. Chloroplasts have the ability to transcribe polycistronic RNA and can perform the correct processing of eukaryotic proteins including the ability to carry out post-translational modifications such as disulphide bonding, assembly of multimers and lipid modifications.

As used herein, a "composition," "pharmaceutical composition" or "therapeutic agent" all include a composition comprising a myelin basic protein comprising construct as described herein. Optionally, the "composition," "pharmaceutical composition" or "therapeutic agent" further comprises pharmaceutically acceptable diluents or carriers.

As used herein, the term "expression" in the context of a gene or polynucleotide involves the transcription of the gene or polynucleotide into RNA. The term can also, but not necessarily, involves the subsequent translation of the RNA into polypeptide chains and their assembly into proteins.

A plant remnant may include one or more molecules (such as, but not limited to, proteins and fragments thereof, minerals, nucleotides and fragments thereof, plant structural components, etc.) derived from the plant in which the protein of interest was expressed. Accordingly, a composition pertaining to whole plant material (e.g., whole or portions of plant leafs, stems, fruit, etc.) or crude plant extract would certainly contain a high concentration of plant remnants, as well as a composition comprising purified protein of interest that has one or more detectable plant remnants. In a specific embodiment, the plant remnant is rubisco.

In another embodiment, the invention pertains to an administrable composition for treating or preventing disease via administration of a therapeutic fusion protein produced in a plant chloroplast. The composition comprises a therapeutically-effective amount of the fusion protein expressed by a plant and a plant remnant.

Proteins expressed in accord with certain embodiments taught herein may be used in vivo by administration to a subject, human or animal in a variety of ways. The pharmaceutical compositions may be administered orally or parenterally, i.e., subcutaneously, intramuscularly or intravenously, though oral administration is preferred.

Oral compositions produced by embodiments of the present invention can be administered by the consumption of the foodstuff that has been manufactured with the transgenic plant producing the plastid derived therapeutic fusion protein. The edible part of the plant, or portion thereof, is used as a dietary component. The therapeutic compositions can be formulated in a classical manner using solid or liquid vehicles, diluents and additives appropriate to the desired mode of administration. Orally, the composition can be administered in the form of tablets, capsules, granules, powders, chewable gums, and the like with at least one vehicle, e.g., starch, calcium carbonate, sucrose, lactose, gelatin, etc. The preparation may also be emulsified. The active immunogenic or therapeutic ingredient is often mixed with excipients which are pharmaceutically acceptable and compatible with the active ingredient. Suitable excipients are, e.g., water, saline, dextrose, glycerol, ethanol or the like and combination thereof. In addition, if desired, the compositions may contain minor amounts of auxiliary substances such as wetting or emulsifying agents, pH buffering agents, or adjuvants. In a preferred embodiment the edible plant, juice, grain, leaves, tubers, stems, seeds, roots or other plant parts of the pharmaceutical producing transgenic plant is ingested by a human or an animal thus providing a very inexpensive means of treatment of or immunization against disease.

In a specific embodiment, plant material (e.g. lettuce, tomato, carrot, low nicotine tobacco material etc,) comprising chloroplasts capable of expressing the therapeutic fusion protein, is homogenized and encapsulated. In one specific embodiment, an extract of the lettuce material is encapsulated. In an alternative embodiment, the lettuce material is powderized before encapsulation.

In alternative embodiments, the compositions may be provided with the juice of the transgenic plants for the convenience of administration. For said purpose, the plants to be transformed are preferably selected from the edible plants consisting of tomato, carrot and apple, among others, which are consumed usually in the form of juice.

According to another embodiment, the subject invention pertains to a transformed chloroplast genome that has been transformed with a vector comprising a heterologous gene that expresses a therapeutic fusion protein or peptide as disclosed herein.

Reference to the protein sequences herein relate to the known full length amino acid sequences as well as at least 12, 15, 25, 50, 75, 100, 125, 150, 175, 200, 225, 250 or 265 contiguous amino acids selected from such amino acid sequences, or biologically active variants thereof. Typically, the polypeptide sequences relate to the known human versions of the sequences.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of polypeptide can be found using computer programs well known in the art, such as DNASTAR software. Whether an amino acid change results in a biologically active therapeutic fusion polypeptide can readily be determined by assaying for native activity, as described for example, in the specific Examples, below.

Reference to genetic sequences herein refers to single- or double-stranded nucleic acid sequences and comprises a coding sequence or the complement of a coding sequence for polypeptide of interest. Degenerate nucleic acid sequences encoding polypeptides, as well as homologous nucleotide sequences which are at least about 50, 55, 60, 65, 60, preferably about 75, 90, 96, or 98% identical to the cDNA may be used in accordance with the teachings herein polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of nucleic acid sequences which encode biologically active polypeptides also are useful polynucleotides.

Variants and homologs of the nucleic acid sequences described above also are useful nucleic acid sequences. Typically, homologous polynucleotide sequences can be identified by hybridization of candidate polynucleotides to known polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% base pair mismatches.

Species homologs of polynucleotides referred to herein also can be identified by making suitable probes or primers and screening cDNA expression libraries. It is well known that the Tm of a double-stranded DNA decreases by 1-1.5° C. with every 1% decrease in homology (Bonner et al., J. Mol. Biol. 81, 123 (1973). Nucleotide sequences which hybridize to polynucleotides of interest, or their complements following stringent hybridization and/or wash conditions also are also useful polynucleotides. Stringent wash conditions are well known and understood in the art and are disclosed, for example, in Sambrook et al., MOLECULAR CLONING: A LABORATORY MANUAL, $2^{nd}$ ed., 1989, at pages 9.50-9.51.

Typically, for stringent hybridization conditions a combination of temperature and salt concentrations should be chosen that is approximately 12-20° C. below the calculated $T_m$ of the hybrid under study. The $T_m$ of a hybrid between a polynucleotide of interest or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962): Tm=81.5° C.-16.6 (log 10 [Na+])+ 0.41 (% G+C)-0.63 (% formamide)-600/1), where 1=the length of the hybrid in base pairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C. The following materials and methods are provided to facilitate the practice of the present invention.

Codon Optimization

To maximize the expression of heterologous genes in chloroplasts, a chloroplast codon optimizer program was developed based on the codon preference of psbA genes across 133 seed plant species. All sequences were downloaded from the National Center for Biotechnology Information (NCBI, ncbi.nlm.nih.gov/genomes/GenomesGroup.cgi?taxid=2759&opt=plastid). The usage preference among synonymous codons for each amino acid was determined by analyzing a total of 46,500 codons from 133 psbA genes. The optimization algorithm (Chloroplast Optimizer v2.1) was made to facilitate changes from rare codons to codons that are frequently used in chloroplasts using JAVA.

Creation of Transplastomic Lines

The native sequence of the FVIII heavy chain (HC) was amplified using pAAV-TTR-hF8-mini plasmid (Sherman et al., 2014) as the PCR template. The codon-optimized HC sequence obtained using Codon Optimizer v2.1 was synthesized by GenScript (Piscataway, N.J., USA). We also optimized the FVIII light chain (LC), IFG-1 and mutanase. The native VP1 gene (906 bp) of Sabin 1 (provided by Dr. Konstantin Chumakov, FDA) was used as the template for PCR amplification. The codon-optimized VP1 sequence was also synthesized by GenScript. Amplified and synthetic gene sequences were cloned into chloroplast transformation vectors pLSLF and pLD-utr for *Lactuca sativa* and Petite Havana, respectively. Sequence-confirmed plasmids were used for bombardment to create transplastomic plants as described previously (Verma et al., 2008). Transplastomic lines were confirmed using Southern blot analysis as described previously (Verma et al., 2008) except for probe labeling and detection, for which DIG high prime DNA labeling and detection starter kit II (Roche, cat no. 11585624910) was used.

Evaluation of Translation

To compare the level of protein expression between native and codon-optimized sequences, immunoblot and densitometric assay were performed using anti-CNTB antibody. Total protein from *E. coli* was extracted by sonicating resuspended *E. coli* cells in 1×PBS and 5 mM EDTA. For total plant protein, powdered lyophilized plant cells were suspended in extraction buffer (100 mM NaCl, 10 mM EDTA, 200 mM Tris-Cl pH 8.0, 0.05% (v/v) Tween-20, 0.1% SDS, 14 mM β-ME, 400 mM sucrose, 2 mM PMSF, and proteinase inhibitor cocktail) in a ratio of 10 mg per 500 μL and incubated on ice for 1 h for rehydration. Suspended cells were sonicated (pulse on for 5 s and pulse off for 10 s, sonicator 3000, Misonix) after vortexing (~30 s). After Bradford assay, equal amounts of homogenized proteins were loaded and separated on SDS-polyacrylamide with known amounts of CNTB protein standard. To detect CNTB fusion proteins, anti-CNTB polyclonal antibody (GenWay Biotech Inc., San Diego, Calif.) was diluted 1:10,000 in 1×PBST (0.1% Tween-20) and then membranes were probed with goat anti-rabbit IgG-HRP secondary antibody (Southern Biotechnology, 4030-05) diluted 1:4,000 in 1×PBST. Chemiluminescent signals were developed on X-ray films, which were used for quantitative analysis with Image J software (IJ 1.46r; NIH).

Evaluation of Transcripts

Total RNA was extracted from leaves of plants grown in agar medium in tissue culture room using an easy-BLUE™ total RNA extraction kit (iNtRON, cat no. 17061). For the RNA gel blot, equal amounts of total RNA (4μg) were separated on a 0.8% agarose gel (containing 1.85% formaldehyde and 1×MOPS) and blotted onto a nylon membrane (Nytran SPC; Whatman, Buckinghamshire, UK). For northern blot, The PCR-amplified product from psbA 5' or 3'UTR region of chloroplast transformation plasmid was used as the probe. The hybridization signals on membranes were detected using DIG labeling and detection kit as described above.

Lyophilization

Confirmed homoplasmic lines were transferred to a temperature- and light-controlled greenhouse. Mature leaves from fully grown transplastomic plants were harvested and stored at −80° C. before lyophilization. To freeze-dry plant leaf materials, frozen, crumbled small leaf pieces were sublimated under 400 mTorr vacuum while increasing the chamber temperature from −40° C. to 25° C. for 3 days (Genesis 35XL, VirTis SP Scientific). Dehydrated leaves were powdered using a coffee grinder (Hamilton Beach) at maximum speed, tobacco was ground 3 times for 10 sec each and lettuce was ground 3 times for 5 sec. Powdered leaves were stored in a container under air-tight and moisture-free condition at room temperature with silica gel.

Frozen CTB-VP1 tobacco leaves were transported to a lyophilizer (Genesis 35XL, SP Scientific, Stone Ridge, N.Y.) on dry ice and lyophilized at −40° C., −30° C., −20° C., −15° C., −10° C., −5° C. and 25° C. for a total of 72 h under a 400 mTorr vacuum. Lyophilized leaf materials were ground in a coffee grinder (Hamilton Beach, Southern Pines, N.C., USA) 3 times at maximum speed (pulse on 10 s and off 30 s). The fine powder was stored with silica gel in a moisture-free environment at room temperature.

Protein Extraction and Sample Preparation for Mass Spectrometry Analysis Total protein was extracted from 10 mg of lyophilized leaf powder by adding 1 mL extraction buffer (2% SDS, 100 mM DTT, 20 mM TEAB). Lyophilized leaf powder was incubated for 30 min at RT with sporadic vortexing to allow rehydration of plant cells. Homogenates were then incubated for 1 h at 70° C., followed by overnight incubation at RT under constant rotation. Cell wall/membrane debris was pelleted by centrifugation at 14,000 rpm (approx. 20,800 rcf). The procedure was performed in duplicate.

All protein extracts (100 µl) were enzymatically digested with 10 µg trypsin/Lys-C (Promega) on a centrifugal device with a filter cut-off of 10 kDa (Vivacon) in the presence of 0.5% sodium deoxycholate, as previously described (Leon et al., 2013). After digestion, sodium deoxycholate was removed by acid precipitation with 1% (final concentration) trifluoroacetic acid. Stable Isotope standard (SIS) peptides (>97% purity, C-term Lys and Arg as Lys U-13C6; U-15N2 and Arg U-13C6; U-15N4, JPT Peptide Technologies) were spiked into the samples prior to desalting. Samples were desalted prior to MS analysis with OligoR3 stage-tips (Applied Biosystems). The initial protein extract (10 µl) was desalted on an OligoR3 stage tip column. Desalted material was then dried on a speed vacuum device and suspended in 6 µL of 0.1% formic acid in water. MS analysis was performed in duplicate by injecting 2 µl of desalted material into the column.

PRM Mass Spectrometry Analysis and Data Analysis

Liquid chromatography-coupled targeted mass spectrometry analysis was performed by injecting the column with 2 µL of peptide, corresponding to the amount of total protein extracted and digested from 33.3 µg of lyophilized leaf powder, with 34 fmol of each SIS peptide spiked in. Peptides were separated using an Easy-nLC 1000 (Thermo Scientific) on a home-made 30 cm×75 µm i.d. C18 column (1.9 µm particle size, ReproSil, Dr. Maisch HPLC GmbH). Mobile phases consisted of an aqueous solution of 0.1% formic acid (A) and 90% acetonitrile and 0.1% formic acid (B), both HPLC grade (Fluka). Peptides were loaded on the column at 250 nL/min with an aqueous solution of 4% solvent B. Peptides were eluted by applying a non-linear gradient for 4-7-27-36-65-80% B in 2-50-10-10-5 min, respectively.

MS analysis was performed using the parallel reaction monitoring (PRM) mode on a Qexactive mass spectrometer (Thermo Scientific) equipped with a nanospray Flex™ ion source (Gallien et al., 2012). Isolation of targets from the inclusion list with a 2 m/z window, a resolution of 35,000 (at m/z 200), a target AGC value of $1\times10^6$, and a maximum filling time of 120 ms. Normalized collision energy was set at 29. Retention time schedules were determined by the analysis of SIS peptides under equal nanoLC chromatography. A list of target precursor ions and retention time schedule is reported in the Supplementary Information. PRM data analysis was performed using Skyline software (MacLean et al., 2010).

Ribosome Profiling

Second and third leaves from the top of the plant were harvested for ribosome profiling. Lettuce plants were approximately 2 months old. Tobacco plants were 2.5 or 2 months old, for native and codon-optimized VP1 constructs, respectively. Leaves were harvested at noon and flash frozen in liquid nitrogen. Ribosome footprints were prepared as described in Zoschke et al (2013) except that ribonuclease I was substituted for micrococcal nuclease. Ribosome footprints were converted to a sequencing library with the NEXTflex Illumina Small RNA Sequencing Kit v2 (BIOO Scientific, 5132-03). rRNA contaminants were depleted by subtractive hybridization after first strand cDNA synthesis using biotinylated oligonucleotides corresponding to abundant rRNA contaminants observed in pilot experiments. Samples were sequenced at the University of Oregon Genomics Core Facility. Sequence reads were processed with cutadapt to remove adapter sequences and bowtie2 with default parameters to align reads to the engineered chloroplast genome sequence.

Chloroplast Vector Construction and Regeneration of Transplastomic Plants

The native VP1 gene (906 bp) of Sabin type 1 poliovirus (provided by Dr. Konstantin Chumakov, FDA) was amplified using forward primer 5'-gggCCCgggCCCCggCgTAAACgCTCTgTTgggT-TAggTCAgATg-3' (SEQ ID NO: 11) and reverse primer 5'-CgATCTAgATCAATATgTggTCAgATC-3' (SEQ ID NO: 12). The PCR-amplified fragment and the codon-optimized VP1 gene (synthesized by GenScript, Piscataway, N.J., USA) were cloned into tobacco and lettuce chloroplast transformation vectors. Biolistic delivery of chloroplast transformation vectors and regeneration of transplastomic tobacco (*Nicotiana tabacum* cv. Petit Havana) and lettuce (*Lactuca sativa* cv. Simpson Elite) lines were performed as previously described (Ruhlman et al., 2007; Verma et al., 2008).

Characterization of Transplastomic Tobacco and Lettuce Lines

To confirm transgene cassette integration into the chloroplast genome, PCR was performed using primer pairs 3P/3M and 5P/2M or 16S-Fw/3M and 5P/2M for tobacco and lettuce, respectively (Verma et al., 2008; Kanagaraj et al., 2011). Southern blot analysis was performed to confirm transgene integration and homoplasmy as previously described (Verma et al., 2008).

Immunoblot Analysis and Purification of Chloroplast-Derived Proteins

Immunoblot analysis and quantitation of CTB-VP1 fusion proteins were performed according to previously published methods (Davoodi-Semiromi et al., 2010). To detect CTB-VP1-fused proteins, blots were incubated with 1:10,000 rabbit anti-CTB polyclonal antibody (GeneWay, San Diego, Calif., USA) or 1:1,000 rabbit anti-VP1 polyclonal antibody (Alpha Diagnostic Intl. Inc., San Antonio, Tex., USA) followed by 1:4,000 goat anti rabbit IgG-HRP as secondary antibody (SouthernBiotech, Birmingham, Ala., USA). CTB (Sigma, St Louis, Mo., USA) and recombinant Sabin 1 VP1 (Alpha Diagnostic Intl. Inc., San Antonio, Tex., USA) were used as positive controls. To purify chloroplast-derived CTB-VP1 fusion proteins, His60 Ni Superflow Resin (Clontech Laboratories, Mountain View, Calif., USA) was used according to the manufacturer's instructions. Eluted fractions were dialyzed 3 times with sterile phosphate-buffered saline (PBS), aliquoted and stored at −20° C. Purified chloroplast-derived CTB-VP1 was used for immunoglobulin measurements.

Cholera Toxin-B-GM1-Ganglioside Receptor Binding Assay

To test the ability of the tobacco chloroplast-derived CTB-VP1 to form pentamers and bind to the GM1-ganglioside receptor, a CTB-GM1 binding assay was performed as described (Davoodi-Semiromi et al., 2010).

Mice and Immunization Schedule

Figure 4A:
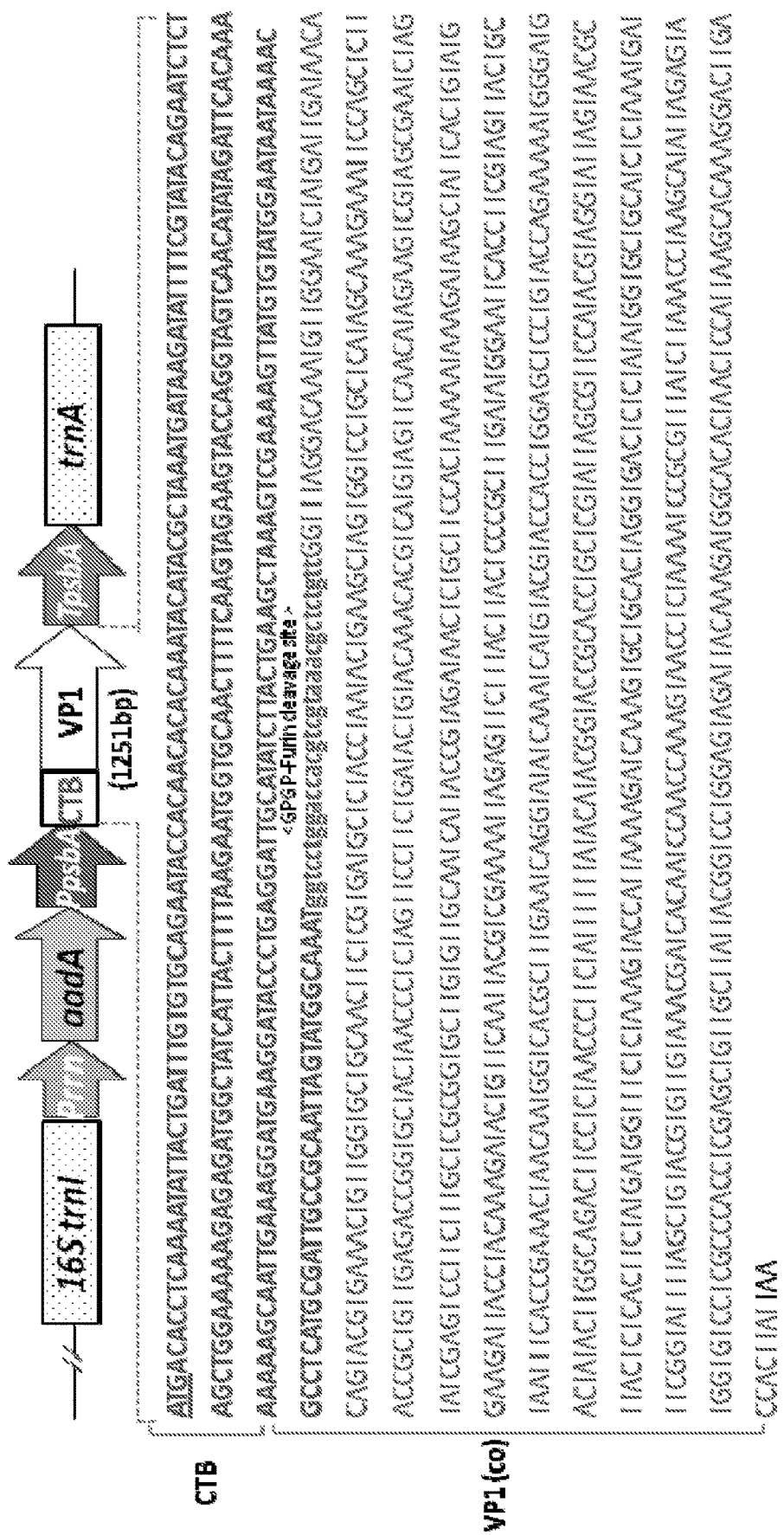
FIG. 4A-D: Creation and characterization of transplastomic tobacco and lettuce lines expressing native and codon-optimized CTB-VP1 and Quantitation of expression of CNTB-FVIII HC and VP1 genes by western blots.
Figure 4B:
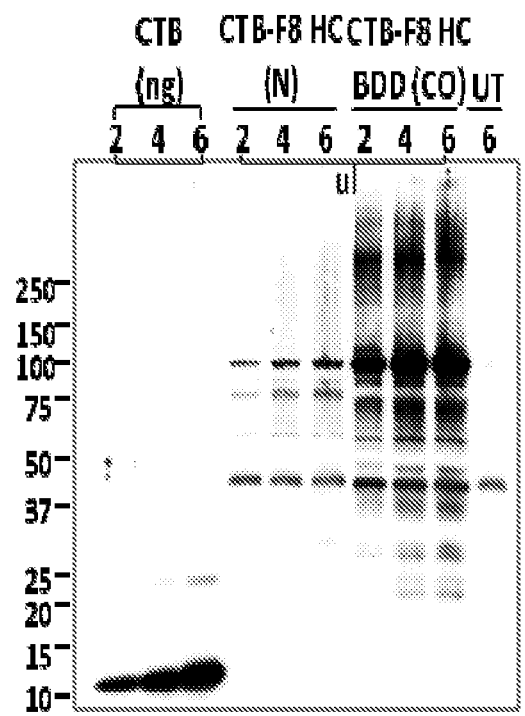

Female CD-1 mice aged 6-7 weeks were purchased from Charles River Laboratories (Wilmington, Mass., USA) and housed in microisolator cages. Experiments were conducted in accordance with guidelines of the University of Pennsylvania Institutional Animal Care and Use Committee. Mice were randomly divided into 9 groups of 10 mice per group. Group 1 was a control group in which mice were untreated. All mice from groups 2 through 8 were subcutaneously (s.c.) primed with 100 µl of IPV suspension of three types of poliovirus (Type 1 (Mahoney), Type 2 (MEF-1), and Type 3 (Saukett) (IPOL, Sanofi Pasteur SA)). Group 2 mice were s.c. boosted with the same IPV 30 days after priming. Mice in groups 3 through 9 were orally boosted with lyophilized plant material: mice in groups 3-8 were boosted once a week for 8 consecutive weeks starting one week after priming. Mice in groups 3 through 5 were orally boosted with lyophilized native CTB-VP1-expressing leaves; each mouse was boosted with 20 mg of material in 200 μl of PBS plus different adjuvants: saponin (group 3), squalene (group 4) or both (group 5). Mice in groups 6 through 9 were orally boosted with lyophilized codon-optimized CTB-VP1-expressing leaves; each mouse was boosted with 20 mg of material in 200 μl of PBS plus different adjuvants: saponin (group 6), squalene (group 7) or both (groups 8 and 9). Blood was collected one day prior to priming and 7 days after boosting. Serum samples were heat-inactivated at 56° C. for 30 min to destroy complement activity.

Preparation of Vaccine Formulations of Bioencapsulated, Plant-Made CTB-VP1 Protein Vaccine formulation was generally performed as previously described[39, 40] but with modifications. Briefly, the double emulsion technique was used to prepare vaccine formulations. To prepare VP1 antigen adjuvanted with squalene, the primary emulsion in the aqueous phase was made by mixing 0.05% Tween-80 in PBS with 20 mg of lyophilized VP1 antigen. The oil phase was a combination of squalene (80% v/v) and Span-80 (Sigma, P4780) (20% v/v). The emulsion was made by mixing the primary oil emulsion with the aqueous phase and adjusting the total volume to 200 μl per mouse with PBS, then homogenizing at 5,000 rpm for 5 min.

To prepare VP1 antigen adjuvanted with saponin, 20 mg lyophilized native or codon-optimized CTB-VP1 plant material was mixed with 2 mg saponin per mouse and PBS was added to a final volume of 200 μl. To prepare VP1 antigen with both adjuvants, a primary emulsion was made by mixing 20 mg of lyophilized native or codon-optimized VP1 with 2 mg saponin in PBS containing 0.05% Tween-80. Then, the primary emulsion was then gently mixed with a squalene emulsion containing squalene (80% v/v) and Span-80 (20% v/v).

Determination of Antibody Response by ELISA

Immunological responses, including serum levels of VP1-specific IgG1 and IgA titers, were assayed by direct ELISA and in vitro poliovirus Sabin 1, 2 and 3 neutralizing assays, which were performed by the Centers for Disease Control and Prevention (CDC). Briefly, for the antibody response assay, 10 μg/ml purified CTB-VP1 protein was used to coat 96-well Maxisorp ELISA plates (Nunc) overnight at 4° C. Plates were blocked with 1% BSA (Sigma 7906) in PBS with 0.05% Tween. Starting with a 1:400 dilution, two-fold dilutions of individual heat-inactivated sera samples were incubated overnight at 4° C. Secondary antibodies were HRP-conjugated rat anti-mouse IgG1 (BD Pharmingen, 559626, 1:1,000) and HRP-conjugated goat anti-mouse IgA (American Qualex, A138N, 1:5,000) diluted in blocking buffer and incubated at 37° C. for 1 h followed by color development with TMB substrate (ES001, EMD Millipore, CA) for 10 min at RT. The reaction was stopped by adding 100 μl of 2N sulfuric acid to each well, and absorbance was measured using an ELISA reader at 450 nm. Antibody titers were defined as the reciprocal of the highest dilution above the cut-off, which was three times the mean background[41]. All sera samples were tested in triplicate. Results are shown as individual antibody titer±SEM.

Poliovirus Sabin 1, 2, 3 Neutralization Assay

After the 10th oral boost with native or codon-optimized CTB-VP1 proteins adjuvanted with saponin and/or squalene or, for group 2, both priming and boosting with the IPV, serum samples were collected and saved at −80° C. for further neutralization assays at the CDC as previously described[21, 42]. Briefly, sera samples were tested in triplicate with the use of modified microneutralization assays for antibodies to Sabin strains type 1, 2, and 3. Serum samples from control and experimental groups were tested randomly and blindly. The serum dilution of a reciprocal titer at which no virus neutralization was detected was recorded as the log 2 (titer) of 2.5, or negative; a log 2 titer of 3 was considered protective. Individual titers for each mouse are plotted and the bar represents mean neutralizing titer±SEM.

Statistical Analysis

All data are reported for individual mice and mean±SEM is given for each group. Analyses for statistically significant differences in antibody titers between groups were performed using Student's t-test (GraphPad Prism version 6) and P values<0.05 were considered significant.

The following examples are provided to illustrate certain embodiments of the invention. They are not intended to limit the invention in any way.

Example I

Use of Genomic, Proteomic and Ribosome Profiling Tools for Comparative Analysis of Native and Codon Optimized Human or Viral Genes Enhances Understanding of Transgene Expression in Chloroplasts Codon-Optimization of Human/Viral Transgenes The differences in codon usage by chloroplasts are often associated with a decrease in translation. In efforts to increase expression of therapeutically relevant proteins, the native sequences of blood clotting factor VIII heavy chain (FVIII HC and FVIII LC), and IGF-1, from human, viral capsid protein 1 (VP1) from polio virus and mutanase from bacteria were analyzed as previous studies showed very low expression levels of <0.005% for FVIII and ~0.1% for VP1, for example. Codon optimization software was developed to increase translation using an algorithm based on the analysis of codons used in psbA genes from 133 plant species because the psbA gene is most highly expressed gene in chloroplasts (FIG. 1). Because the translation efficiency of the psbA gene is >200 times higher than the rbcL gene, this gene was chosen for optimization (Eibl et al., 1999). Furthermore, among 140 transgenes expressed in chloroplasts, >75% use the psbA regulatory sequences. The synonymous codons for each amino acid were ranked according to their frequency of use as shown in FIG. 1. Therefore, most of the rare codons of heterologous genes were modified by the codon optimizer program, according to codons used in psbA genes. In the development of the codon-optimization program, we also investigated expression of synthetic genes using only the highest preferred codon for each amino acid.

Evaluation of Translation of Native and Synthetic Genes in *E. coli*

In this study, the native sequences for FVIII HC (2262 bp), FVIII LC and FVIIISC[c] (a fusion form of codon-optimized FVIII heavy chain (HC including 14 amino acids from B domain) and light chain (LC) (FIG. 2A and FIG. 2E) and VP1 (FIG. 4A) (906) were codon-optimized using the newly developed chloroplast codon-optimizer and synthesized. After codon optimization, AT content of FVIII HC increased slightly from 56% to 62% and 383 codons out of 754 amino acids were optimized. For VP1 sequence from Sabin 1, 906-bp long native sequence was codon optimized, which slightly increased AT content from 51.98% to 59.03% and 187 codons out of 302 amino acids were optimized. The synthetic gene cassettes were inserted into the chloroplast transformation vector, pLSLF for lettuce or pLD-utr for tobacco (FIG. 2A and FIG. 4A). The native and synthetic genes were fused to the cholera non-toxic B subunit (CNTB) which is used for efficient mucosal delivery of the fused proteins via monosialo-tetrahexosylganglioside receptors (GM1) present on the intestinal epithelial cells. To eliminate possible steric hindrance caused by the fusion of two proteins and facilitate the release of tethered protein into circulation after internalization, nucleotide sequences for hinge (Gly-Pro-Gly-Pro) and furin cleavage site (Arg-Arg-Lys-Arg) were engineered between CNTB and fused proteins. The fusion genes were placed under identical psbA promoter, 5'UTR and 3' UTR for specific evaluation of codon optimization (FIG. 2A and FIG. 4A). For the selection of transformants, the gene for aminoglycoside-3"-adenylyl-transferase gene (aadA) was driven by the ribosomal RNA promoter (Prrn) to confer transformed cells resistance to spectinomycin. The expression cassettes were flanked by sequences for isoleucyl-tRNA synthetase (trnI) and for alanyl-tRNA synthetase (trnA) gene, which are identical to the endogenous chloroplast genome sequences, leading to efficient double homologous recombination and optimal processing of introns with flanking sequences.

Figure 2B:
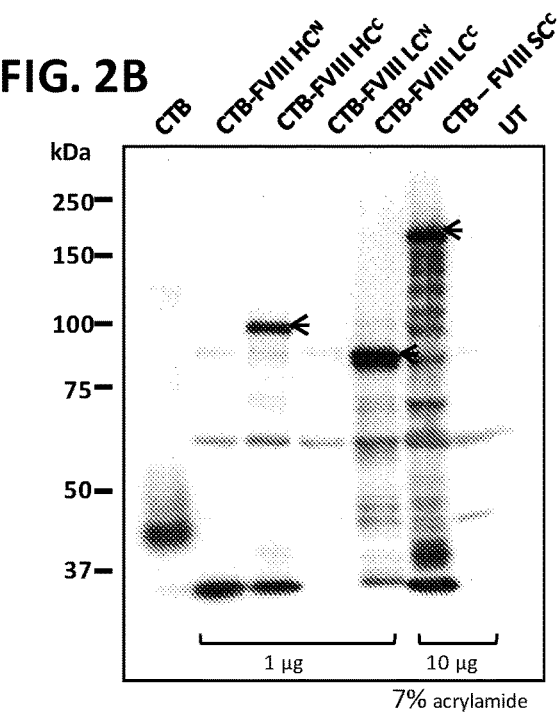
Figure 2C:
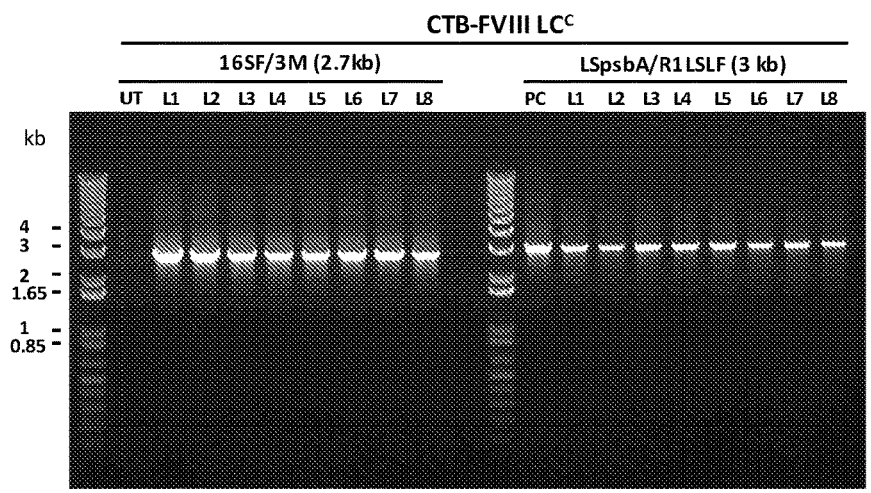

Before creation of transplastomic plants expressing the codon-optimized CNTB-FVIII HC and CNTB-VP1, the synthetic genes were first transformed into *E. coli* to evaluate their expression. Because of prokaryotic origin, chloroplasts have similar transcription/translation machinery. As seen in FIG. 2B, the expression level of the native FVIII gene was ~11 times less than synthetic FVIII gene which was cloned into both lettuce and tobacco chloroplast transformation vectors. In contrast, the synthetic FVIII gene composed of only most highly preferred codons was not even detectable in western blots. For CNTB-VP1, the codon-optimized sequence expressed 3 fold higher than the native sequence. Also, synthetic VP1 gene composed of only the highly preferred codons showed 2 fold less expression than the native sequence.

Figure 2D:
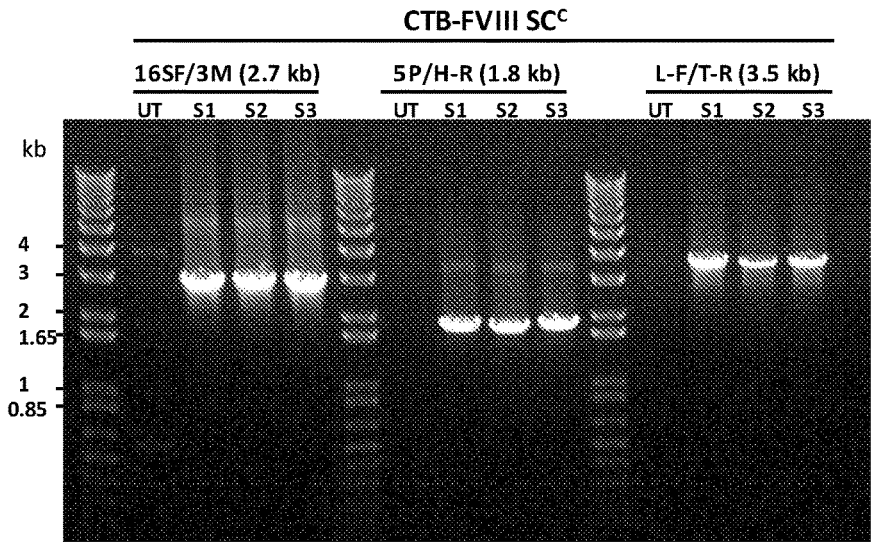
Figure 2E:
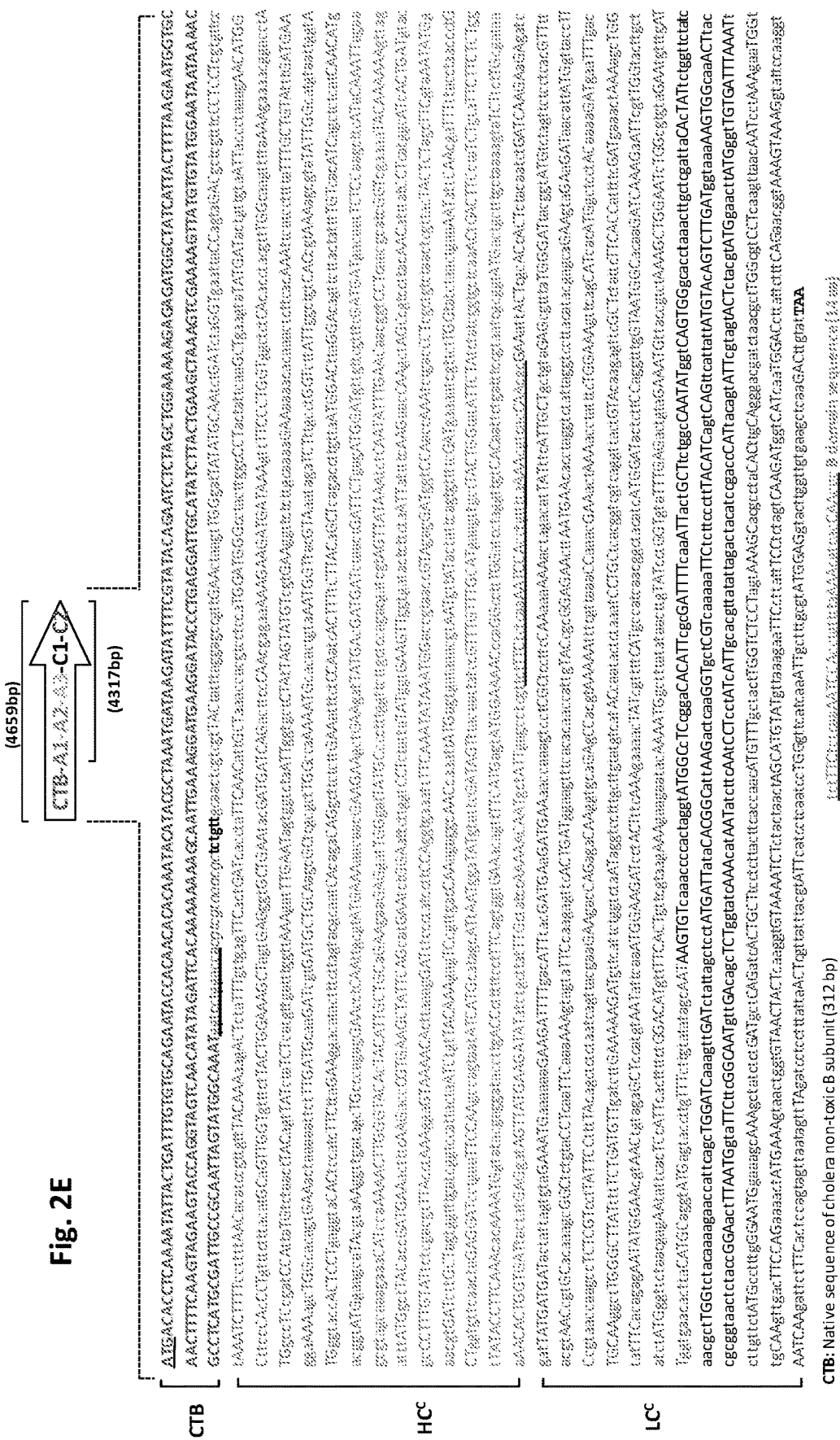

Translation Efficiency of Native and Codon-Optimized Genes in Lettuce and Tobacco Chloroplasts After confirmation of improvement in expression of synthetic sequences in *E. coli*, the transformation vectors containing synthetic FVIII HC and VP1 sequence were used to create transplastomic lettuce and tobacco plants expressing codon-optimized HC and VP1. To confirm homoplasmy, Southern blot analysis was performed with four independent lettuce and tobacco lines expressing native and codon-optimized FVIII HC, and lines expressing native and codon-optimized VP1. For lettuce plants expressing CNTB-FVIII HC, native and codon-optimized sequence, chloroplast genomic DNA was digested by HindIII and probed with dig-labelled probe spanning flanking region (FIG. 2D). For tobacco plants expressing CNTB-HVIII HC (codon-optimized), AflIII was used for digestion of genomic DNA. All selected lines showed the expected distinct hybridizing fragments with no untransformed fragment (FIG. 3A). In case of tobacco plants expressing CNTB-VP1 encoded by the construct shown in FIG. 4A, the extracted total genomic DNA from four independent transplastomic lines was digested by AflIII and probed with flanking sequence, showed two distinct hybridization fragments with no 4.4 kb untransformed fragment. Therefore, these data confirm homoplasmy of all transplastomic lines and their expression levels should therefore be directly related to translation efficiency and not the transgene copy number.

Figure 4C:
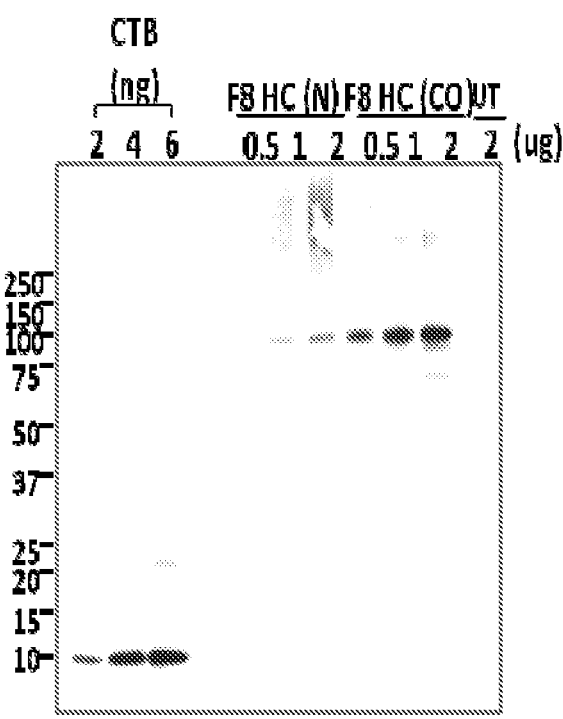
Figure 4D:
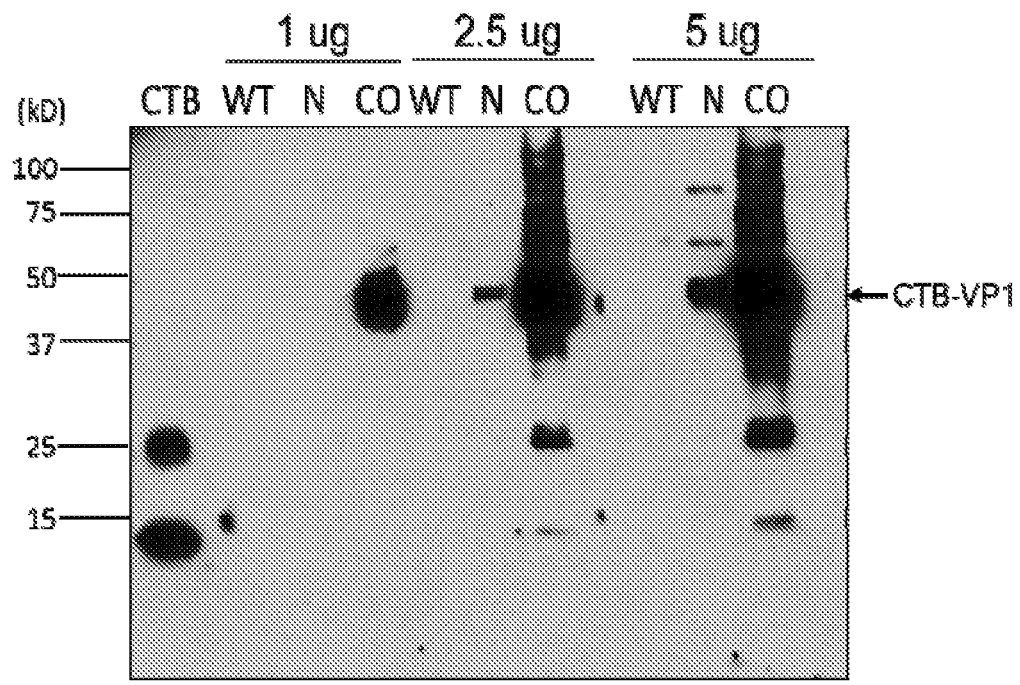

Expression levels of codon-optimized or native gene sequences were quantified using immunoblot and densitometry assays (FIGS. 4C and 4D). The concentration of FVIII HC of codon-optimized gene between about 100.7 to about 596.6 ug/g DW, was 1.76 to 29.8 fold higher than that of lettuce plant expressing the native FVIII HC gene which was between about 20.0 to about 57.2 µg/g DW. Percentage of total leaf protein (% TLP) was about 2.23 to about 25.33-fold higher in codon-optimized (0.058 to about 0.38%) than the native human gene sequence (0.015 to about 0.026%). Such variations in expression levels are due to the age of leaves and different developmental stages. The batch used for PRM mass spectrometry in this study showed a 5.02 fold increase based on dry weight (100.7 vs 20.0 µg/g DW) or a 3.98 fold increase based on total leaf protein (0.074 vs 0.016% TLP) between codon-optimized and native sequence, respectively. In case of tobacco plants, the concentration in codon-optimized plants was between about 847.7 and 1266.0 µg/g DW, and expressed about 9.92 to 34.6 fold higher FVIII protein than the native gene which was between about 36.6 and about 85.5 µg/g DW, or about 4.0 to about 13.9 fold higher based on TLP. For the tobacco plants expressing CNTB-VP1, the batch used for PRM mass spectrometry showed 48 fold higher based on DW (2,600 vs 54 µg/g DW) and 46 fold higher based on TLP (4.6% vs 0.1%) between codon-optimized and native sequence, respectively (FIG. 4D). From these data, the codon-optimized sequences obtained from our newly developed codon optimizer program significantly improved translation of transgenes to different levels, based on the coding sequence.

Figure 5A:
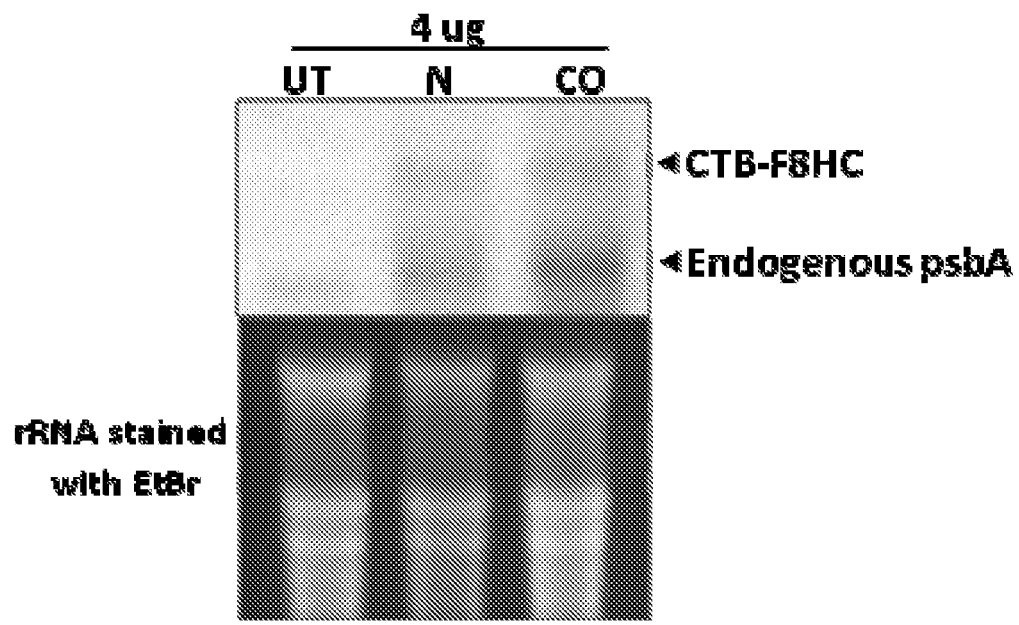
FIGS. 5A-B: Quantitation of transgene transcripts by northern blots. Northern blot of CNTB-F8 HC (FIG. 5A) and CNTB-VP1 (FIG. 5B) genes probed with 200 bp of psbA 5'UTR (for FVIII) or psbA 3'UTR (for VP1) regulatory sequences. Lower and upper transcripts represent the endogenous psbA gene and CNTB-FVIII genes. Ethidium bromide (EtBr) stained gels are included for evaluation of equal loading. UT, untransformed wild type; N, native sequence; CO, codon-optimized sequence.
Figure 5B:
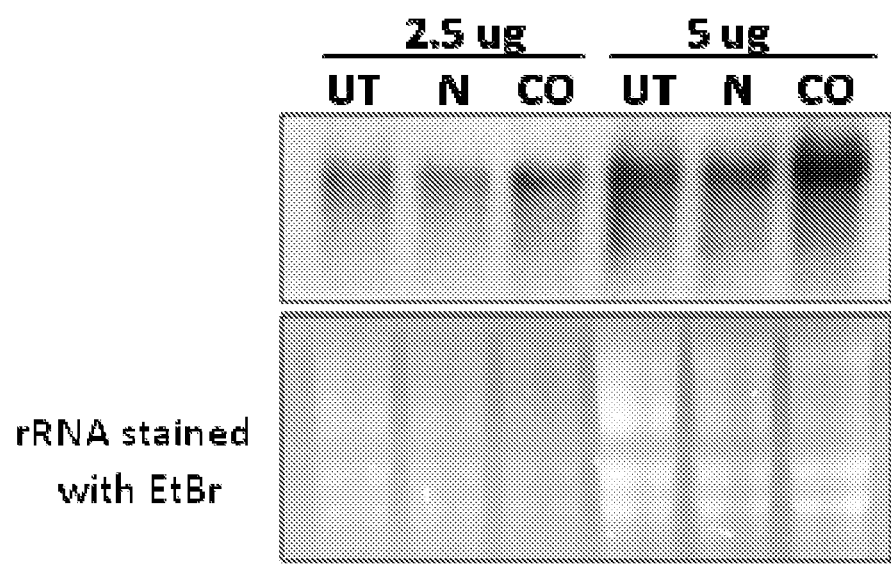

To investigate the impact of codon optimization on transcript stability, northern blots were performed with a probe, psbA 5' or 3' UTR sequence (FIG. 5A-B). Extracted total RNAs were loaded in a serial manner and the detected mRNA levels of codon-optimized and native sequence for CNTB-FVIII HC and CNTB-VP1 were normalized to endogenous psbA transcript using densitometry and then the normalized ratios were compared. Northern blots indicated that the increase of codon-optimized CNTB-F VIII and -VP1 accumulation is at translational level rather than RNA transcript abundance or stability.

Absolute Quantitation by PRM Analysis

Figure 6A:
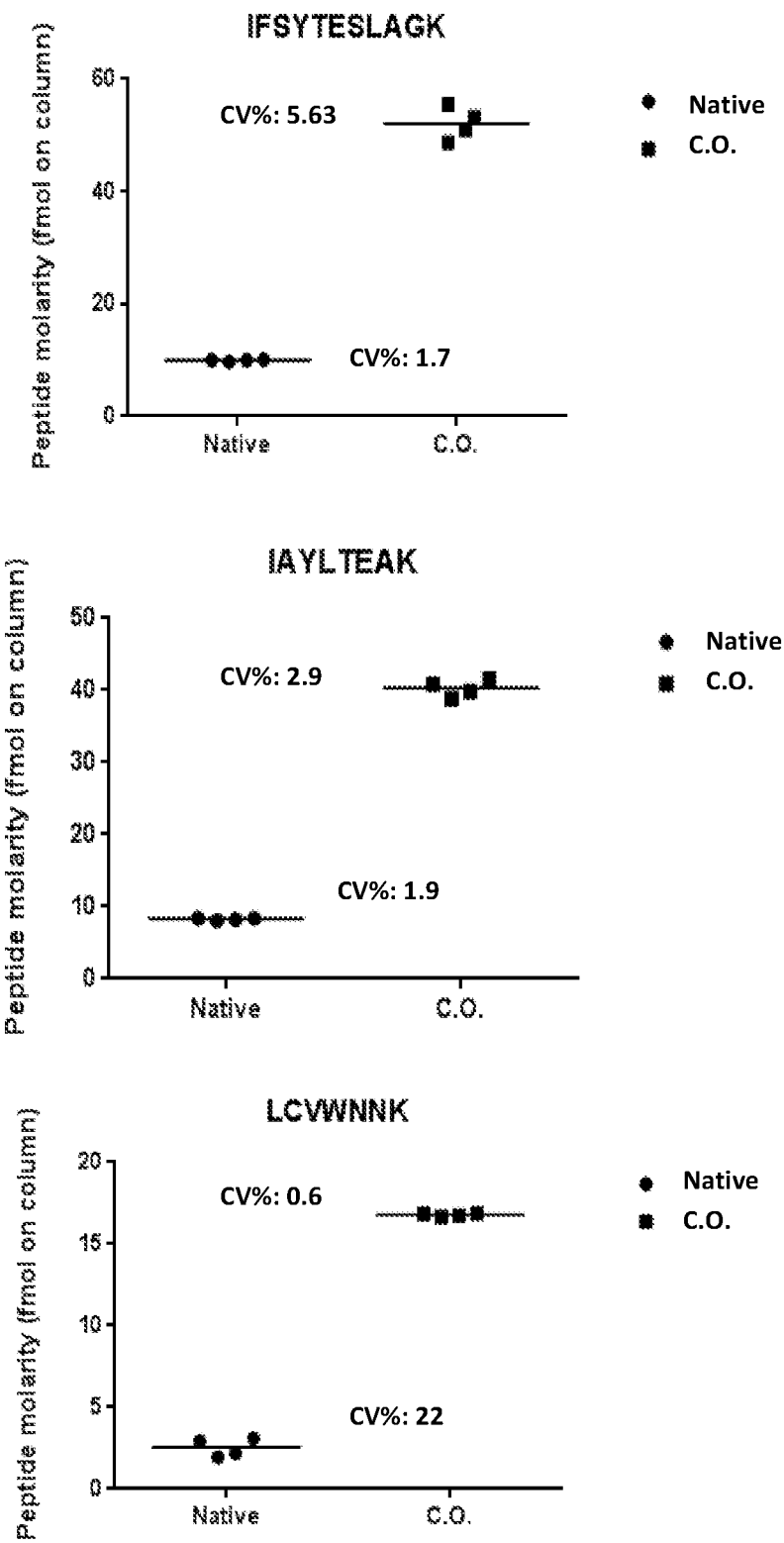
Figure 6B:
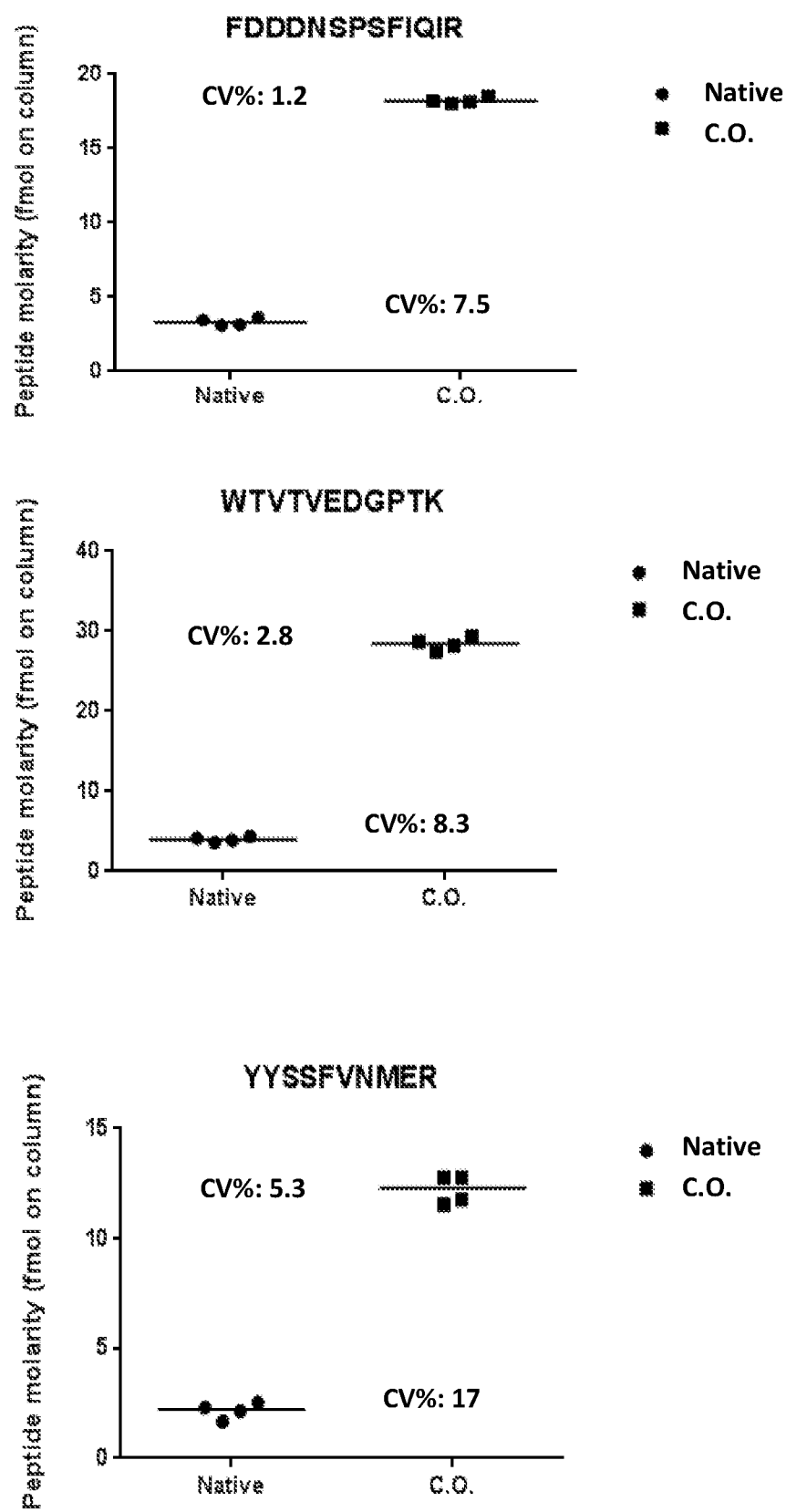
Figure 7A:
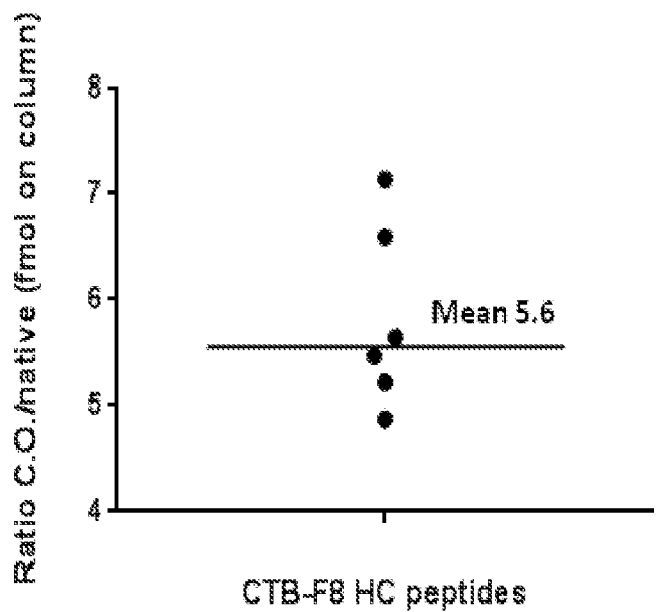
FIG. 7A-B: PRM mass spectrometry analysis and fold changes observed after codon optimization. The reported fold change increase represents the median of the results from six and three peptides, CNTB-FVIII (FIG. 7A) and CNTB-VP1 (FIG. 7B), respectively. Exe-y represents the fold change increase (based on measured fmol on column) of peptides from codon optimized or native plant extracts. CNTB: peptide 1, IFSYTESLAGK (SEQ ID NO: 5); peptide 2, IAYLTEAK (SEQ ID NO: 6); peptide 3, LCVWNNK (SEQ ID NO: 7). FVIII: peptide 4, FDDDNSPSFIQIR (SEQ ID NO: 8); peptide 5, WTVTVEDGPTK (SEQ ID NO: 9); peptide 6, YYSSFVNMER (SEQ ID NO: 10).

Expression levels of codon-optimized and native gene sequences were also quantified using PRM mass spectrometry (FIG. 6A-C). To select the optimal proteotypic peptides for PRM analysis of the CNTB and FVIII HC sequences, we first performed a standard MS/MS analysis (data not shown) of a tryptic digest of lettuce plant expressing CNTB-FVIII HC. From this experiment we chose three peptides from CNTB (peptide 1, IFSYTESLAGK (SEQ ID NO: 5); peptide 2, IAYLTEAK (SEQ ID NO: 6); peptide 3, LCVWNNK (SEQ ID NO: 7) and three FVIII HC tryptic peptides (peptide 4, FDDDNSPSFIQIR (SEQ ID NO: 8); peptide 5, WTVTVEDGPTK (SEQ ID NO: 9); peptide 6, YYSSFVNMER (SEQ ID NO: 10). The content of FVIII HC protein of codon-optimized plant was calculated as results of PRM measurement of the three CNTB tryptic peptides and the three FVIII HC tryptic peptides (FIG. 6A-B). The Tcontent of FVIII HC protein of codon-optimized lettuce plant was 5.6 fold higher than that of lettuce plant expressing native sequence (FIG. 7A). Peptides chosen from CTB showed the range of fold change between native and codon-optimized construct from 4.9 (IAYLTEAK) (SEQ ID NO: 6) to 5.2 (IFSYTESLAGK) (SEQ ID NO: 5) to 6.6 (LCVWNNK) (SEQ ID NO: 7). Peptides chosen from F VIII HC showed the range from 5.5 (FDDDNSPSFIQIR) (SEQ ID NO: 8) to 5.7 (YYSSFVNMER) (SEQ ID NO: 10) to 7.1 (WTVT-VEDGPTK) (SEQ ID NO: 9)(FIG. 7A). These results are reported in Table 1. Linearity of the quantification range was also determined (data not shown). For all the six peptides we observed an $R^2$ value over 0.98.

TABLE 1

Fold change CO with regards to native at peptide level.

| Peptide Sequence | Protein Name | Protein Sequence Type | Protein Target | Ratio AUC To Standard (ratio L/H) | fmol Based on SIS amount | Median (fmol) of 4 Replicates | Standard Desv. | CV (%) | Fold change CO with Regards Native at Peptide level |
|---|---|---|---|---|---|---|---|---|---|
| IFSYTESLAGK | CTB | Native | CNTB-FVIII HC | 0.2862 | 9.7308 | 9.9634 | 0.173388889 | 1.73990897 | |
| IFSYTESLAGK | | | | 0.2985 | 10.149 | | | | |
| IFSYTESLAGK | | | | 0.2941 | 9.9994 | | | | |
| IFSYTESLAGK | | | | 0.2936 | 9.9824 | | | | |
| IFSYTESLAGK | CTB | C.O. | CNTB-FVIII HC | 1.5653 | 53.2202 | 52.0846 | 2.937310801 | 5.639883576 | 5.226543842 |
| IFSYTESLAGK | | | | 1.6327 | 55.5118 | | | | |
| IFSYTESLAGK | | | | 1.4973 | 50.9082 | | | | |
| IFSYTESLAGK | | | | 1.4323 | 48.6982 | | | | |
| IAYLTEAK | CTB | Native | CNTB-FVIII HC | 0.2466 | 8.3844 | 8.2671 | 0.156165767 | 1.889002995 | |
| IAYLTEAK | | | | 0.2425 | 8.245 | | | | |
| IAYLTEAK | | | | 0.2466 | 8.3844 | | | | |
| IAYLTEAK | | | | 0.2369 | 8.0546 | | | | |
| IAYLTEAK | CTB | C.O. | CNTB-FVIII HC | 1.2004 | 40.8136 | 40.2373 | 1.179920839 | 2.932405602 | 4.867160189 |
| IAYLTEAK | | | | 1.2211 | 41.5174 | | | | |
| IAYLTEAK | | | | 1.14174 | 38.8178 | | | | |
| IAYLTEAK | | | | 1.1706 | 39.8004 | | | | |
| LCVWNNK | CTB | Native | CNTB-FVIII HC | 0.064 | 2.176 | 2.5398 | 0.562861759 | 21.16165679 | |
| LCVWNNK | | | | 0.0573 | 1.9482 | | | | |
| LCVWNNK | | | | 0.0865 | 2.941 | | | | |
| LCVWNNK | | | | 0.091 | 3.094 | | | | |
| LCVWNNK | CTB | C.O. | CNTB-FVIII HC | 0.4949 | 16.8266 | 16.7654 | 0.096524473 | 0.575748107 | 6.60107095 |
| LCVWNNK | | | | 0.4893 | 16.6362 | | | | |
| LCVWNNK | | | | 0.4926 | 16.7484 | | | | |
| LCVWNNK | | | | 0.4956 | 16.8504 | | | | |

TABLE 1-continued

Fold change CO with regards to native at peptide level.

| Peptide Sequence | Protein Name | Sequence Type | Protein Target | Ratio AUC To Standard (ratio L/H) | fmol Based on SIS amount | Median (fmol) of 4 Replicates | Standard Desv. | CV (%) | Fold change CO with Regards Native at Peptide level |
|---|---|---|---|---|---|---|---|---|---|
| FDDDNSPSFIQIR FDDDNSPSFIQIR FDDDNSPSFIQIR FDDDNSPSFIQIR | FVIII HC | Native | CNTB-FVIII HC | 0.091 0.0923 0.1016 0.1063 | 3.094 3.1382 3.4544 3.6142 | 3.3252 | 0.2507562437 | 7.541087539 | |
| FDDDNSPSFIQIR FDDDNSPSFIQIR FDDDNSPSFIQIR FDDDNSPSFIQIR | FVIII HC | C.O. | CNTB-FVIII HC | 0.5301 0.5451 0.5334 0.5337 | 18.0234 18.5334 18.2104 18.1458 | 18.22825 | 0.217712861 | 1.194370614 | 5.48185O716 |
| WTVTVEDGPTK WTVTVEDGPTK WTVTVEDGPTK WTVTVEDGPTK | FVIII HC | Native | CNTB-FVIII HC | 0.128 0.1212 0.114 0.1054 | 4.352 4.1208 3.876 3.5836 | 3.9831 | 0.329706516 | 8O277635911 | |
| WTVTVEDGPTK WTVTVEDGPTK WTVTVEDGPTK WTVTVEDGPTK | FVIII HC | C.O. | CNTB-FVIII HC | 0.8629 0.845 0.8277 0.8086 | 29.3386 28.73 28.1418 27.4924 | 28.4257 | 0.791124305 | 2.783130426 | 7.136577038 |
| YYSSFVNMER YYSSFVNMER YYSSFVNMER YYSSFVNMER | FVIII HC | Native | CNTB-FVIII HC | 0.0491 0.0745 0.0674 0.0632 | 1.6694 2.533 2.2916 2.1488 | 2.1607 | 3.363895315 | 16.8415474 | |
| YYSSFVNMER YYSSFVNMER YYSSFVNMER YYSSFVNMER | FVIII HC | C.O. | CNTB-FVIII HC | 0.376 0.3759 0.3463 0.3396 | 12.784 12.7806 11.7742 11.5464 | 12.2213 | 0.654430083 | 5.354831997 | 5.656176239 |
| IFSYTESLAGK | CTB | Native | CNTB- | 0.1231 | 4.1854 | 4.36645 | 0.291829995 | | |

TABLE 1-continued

Fold change CO with regards to native at peptide level.

| Peptide Sequence | Protein Name | Sequence Type | Protein Target | Ratio AUC To Standard (ratio L/H) | fmol Based on SIS amount | Median (fmol) of 4 Replicates | Standard Desv. | CV (%) | Fold change CO with Regards Native at Peptide level |
|---|---|---|---|---|---|---|---|---|---|
| IFSYTESLAGK | | | VP1 | 0.1172 | 3.9848 | | | | |
| IFSYTESLAGK | | | | 0.1354 | 4.6036 | | | | |
| IFSYTESLAGK | | | | 0.138 | 4.692 | | | | |
| IFSYTESLAGK | CTB | C.O. | CNTB- | 3.4942 | 118.8028 | 122.2028 | 2.987506114 | 2.444711671 | 27.9867627 |
| IFSYTESLAGK | | | VP1 | 3.7283 | 126.7622 | | | | |
| IFSYTESLAGK | | | | 3.6112 | 122.7808 | | | | |
| IFSYTESLAGK | | | | 3.5431 | 120.4654 | | | | |
| IAYLTEAK | CTB | Native | CNTB- | 0.1049 | 3.5666 | 3.621 | 0.072124892 | 1.991850088 | |
| IAYLTEAK | | | VP1 | 0.1043 | 3.5462 | | | | |
| IAYLTEAK | | | | 0.1071 | 3.6414 | | | | |
| IAYLTEAK | | | | 0.1097 | 3.7298 | | | | |
| IAYLTEAK | CTB | C.O. | CNTB- | 2.7673 | 94.0882 | 94.13155 | 1.357152441 | 1.441761493 | 25.99600939 |
| IAYLTEAK | | | VP1 | 2.8341 | 96.3594 | | | | |
| IAYLTEAK | | | | 2.7333 | 92.9492 | | | | |
| IAYLTEAK | | | | 2.7391 | 93.1294 | | | | |
| LCVWNNK | CTB | Native | CNTB- | 0.0393 | 1.3362 | 1.47475 | 0.14677952 | 9.952840822 | |
| LCVWNNK | | | VP1 | 0.0392 | 1.3328 | | | | |
| LCVWNNK | | | | 0.0493 | 1.6762 | | | | |
| LCVWNNK | | | | 0.0457 | 1.5538 | | | | |
| LCVWNNK | CTB | C.O. | CNTB- | 0.9762 | 33.1908 | 33.1585 | 0.681449829 | 2.055128638 | 22.48414986 |
| LCVWNNK | | | VP1 | 1.0074 | 34.2516 | | | | |
| LCVWNNK | | | | 0.9622 | 32.7148 | | | | |
| LCVWNNK | | | | 0.9552 | 32.4768 | | | | |

The content of VP1 protein of codon-optimized plant was calculated as results of PRM measurement of the three CNTB tryptic peptides (FIG. 6C). The content of VP1 protein of codon-optimized plant was calculated as 25.9 fold higher than that of tobacco plant expressing native sequence VP1 The fold increase ranges from 22.5 (LCVWNNK) (SEQ ID NO: 7) to 26.0 (IAYLTEAK) (SEQ ID NO: 6) to 28.0 (IFSYTESLAGK) (SEQ ID NO: 5) (FIG. 7B). Linearity of the quantification range was also investigated by spiking SIS peptides in a constant amount of plant digest (1:1:1:1 mix of all 4 types of plant materials) in a dynamic range covering from 220 atomols to 170 fmol (values equivalent on column per injection).

Absolute quantitation can be achieved by spiking a known amount of the counterpart SIS peptide into the samples. For each counterpart SIS peptide (34 fmol) was injected on column mixed with protein digest (equivalent to protein extracted from 33.3 μg lyophilized leaf powder). By calculating ratios of area under the curve (AUC) of each, SIS and endogenous peptides, we estimated the endogenous peptide molarity, expressed as femtomole on column (FIG. 6A-C). The mean of all calculated ratios of fentomoles on column (6 and 3 peptides, CNTB-FVIII HC and CNTB-VP1, respectively) for codon optimized and native sequences is reported as fold increase of protein expression in the codon optimized constructs. The high reproducibility of the sample preparation and PRM analysis is shown in FIG. 6A-C. All peptide measurements were the result of four technical replicates, two sample preparation replicates (from leaf powder to extraction to protein digestion) and two MS technical replicates. Coefficients of variation (%) among the 4 measurements per peptide ranged from 0.5% to 10% in all but in two cases were where it was 16% and 22%.

Ribosome Profiling Studies

Ribosome profiling uses deep sequencing to map "ribosome footprints"—the mRNA fragments that are protected by ribosomes from exogenous nuclease attack. The method provides a genome-wide, high resolution, and quantitative snapshot of mRNA segments occupied by ribosomes in vivo (Ingolia et al., 2009). Overall ribosome footprint coverage can provide an estimate of translational output, and positions at which ribosomes slow or stall are marked by regions of particularly high ribosome occupancy.

To examine how codon optimization influenced ribosome behavior, we profiled ribosomes from plants expressing the native and codon optimized CNTB-FVIII HC and CNTB-VP1 transgenes. FIGS. 8A-8C show the abundance of ribosome footprints as a function of position in each transgene; footprint coverage on the endogenous chloroplast psbA and rbcL genes is shown as a means to normalize the transgene data between the optimized and native constructs. Ribosome footprint coverage was much higher in the codon-optimized VP1 sample than in the native VP1 sample (FIG. 8A). However, the magnitude of this increase varies depending upon how the data are normalized (FIG. 8C): the increase is 5-fold, 16-fold, or 1.5-fold when normalized to total chloroplast ribosome footprints, psbA ribosome footprints, or rbcL ribosome footprints, respectively. These numbers are considerably lower than the 22-28 fold increase in VP1 protein abundance inferred from the quantitative mass spectrometry data. The topography of ribosome profiles is generally highly reproducible among biological replicates (see for example, rbcL and psbA in FIG. 8B). In that context it is noteworthy that the peaks and valleys in the endogenous psbA and rbcL genes are quite different in the native and optimized tobacco VP1 lines. Many of the large peaks (presumed ribosome pauses) observed in these endogenous genes specifically in the native VP1 line map to paired alanine codons (asterisks in FIG. 8A). It is possible that global differences in ribosome behavior at alanine codons may contribute to differential transgene expression in the native and codon optimized lines.

The number of ribosome footprints in FVIII line decreased ~2-fold in the codon-optimized line, whereas protein accumulation increased 5-7 fold. However, a major ribosome pause can be observed near the 3' end of the native transgene, followed by a region of very low ribosome occupancy (see bracketed region in FIG. 8B). This ribosome pause maps to a pair of CTC leucine codons, a codon that is never used in native psbA genes (see FIG. 1). These results strongly suggest that the stalling of ribosomes at these leucine codons limits translation of the downstream sequences and overall protein output, while also causing a build up of ribosomes on the upstream sequences. Thus, overall ribosome occupancy does not reflect translational output in this case. Modification of those leucine codons in the codon-optimized variant eliminated this ribosome stall and resulted in a much more even ribosome distribution over the transgene (FIG. 8B, right). Ribosome footprint coverage is much more uniform on the codon-optimized transgene (FIG. 8C).

DISCUSSION

Codon Usage is not Similar Between *E. coli* and Chloroplasts

The codon-optimized FVIII HC, LC and SC sequences improved expression level in *E. coli* 7-10 fold. Homoplasmic lines (transformation of all chloroplast genomes) were confirmed by Southern blot. The highest levels of expression level of codon-optimized CTB-FVIII heavy chain (100 kDa), light chain (92 kDa) and single chain (179 kDa) were 2440, 160 and 230 μg/g in lyophilized plant cells, respectively. In single chain lettuce, the expression level increased from 150 μg/g to 230 μg/g with age from 26-day to 48-day. Translation efficiency of synthetic genes was first tested in *E. coli* expression system because of the prokaryotic origin of chloroplasts. However, the expression of the synthetic VP1 gene showed only 3 times higher than the native gene. Lower level of translation of synthetic VP1 than FVIII HC could be due to differences in rarely used codons between *E. coli* and chloroplast. In *E. coli*, among 6 arginine codons, four (AGG, AGA, CGG and CGA) codons are not preferred. Also, GGA for glycine, AUA for isoleucine, CUA for leucine, and CCC for proline (Kane, 1995) are least preferred codons in *E. coli*. Usually the small number of rare codons do not cause severe impediment in translation. However, clustering of a large number of the rare codons affects translation. Arginine codons AGG/AGA have been extensively studied for their detrimental effect on protein expression in *E. coli*. In a study which used a test protein with different magnitude of tandem repeat of AGG codons, translation was drastically reduced when the number of AGG clusters was two to five (Rosenberg et al., 1993). While there is no clustering issue of the rare codons for the native VP1, it was found that the native sequence of FVIII HC has 3 clustering sites where rare codons for arginine or glycine were consecutively placed, for example, at codons 3 and 4 (AGA-AGA), codons 489 and 499 (AGG-AGA), and codons 562 and 563 (AGA-GGA). So the elimination of the multiple repeat of rare Arg codons from native FVIII HC sequence by codon optimization could increase translation of the synthetic HC in *E. coli*. In contrast, the native sequence of VP1 has no such tandem repeats of the rare codons so that the expression efficiency was less affected than FVIII HC native sequence. In view of these data it is clear that production and oral delivery of FVIII SC clotting factor using edible lettuce will benefit patients with increased compliance, in a cost-effective and safe manner. Large scale/clinical grade production of therapeutic plant leaves at cGMP facility will reinforce evaluation of plant-made clotting factors in large animal models, non-human primates and facilitate toxicology studies.

Codon Optimization Significantly Enhances Translation in Chloroplasts

The increase of 22.5~28.0 fold (by PRM) and 46-48 fold (by WB) between the native and codon-optimized VP1 in chloroplasts is quite remarkable. Since the codon optimizer was designed to optimize expression of heterologous genes in chloroplasts, it is expected that improvement of expression level between native and synthetic sequence in chloroplasts is much greater than that of expression in E. coli. For example, CUA for leucine is rarely used in E. coli but the same codon is most favorably used in chloroplasts. The codon optimization program increased the ratio of CUA among 6 leucine codons from 27.8% of native sequence to 38.9% of codon-optimized sequence for VP1. In contrast to expression in E. coli, fold difference of protein level between VP1 plants expressing native and codon-optimized sequence was greater than that of plants expressing FVIII HC between native and codon-optimized sequence. Given that higher molecular weight of FVIII (754 amino acids) than VP1 (302 amino acids) requiring more tRNAs and amino acids in chloroplasts, the resultant protein synthesis will be less efficient. Considering that chloroplasts have an extremely high capacity to synthesize and accumulate foreign proteins, the nitrogen supply and amino acid pool could be a major concern for accumulation of recombinant proteins. As seen in previous report (Bally et al., 2009), total amino acid content of transplastomic plants was significantly affected with reduction of resident proteins, especially Rubisco, due to the limited resources of protein synthesis, which usually functions as a major leaf amino acid storage protein.

Figure 8A:
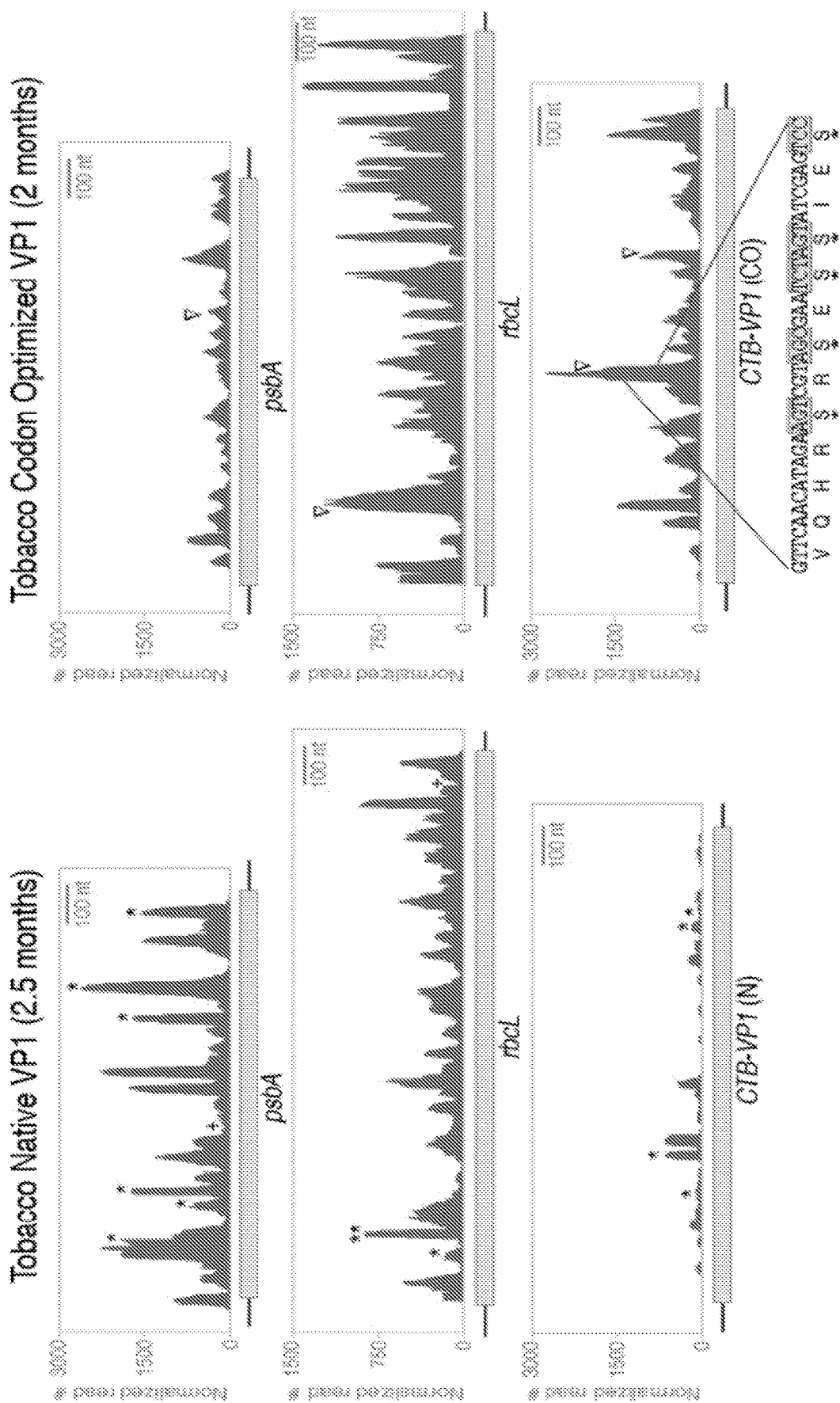
Figure 8B:
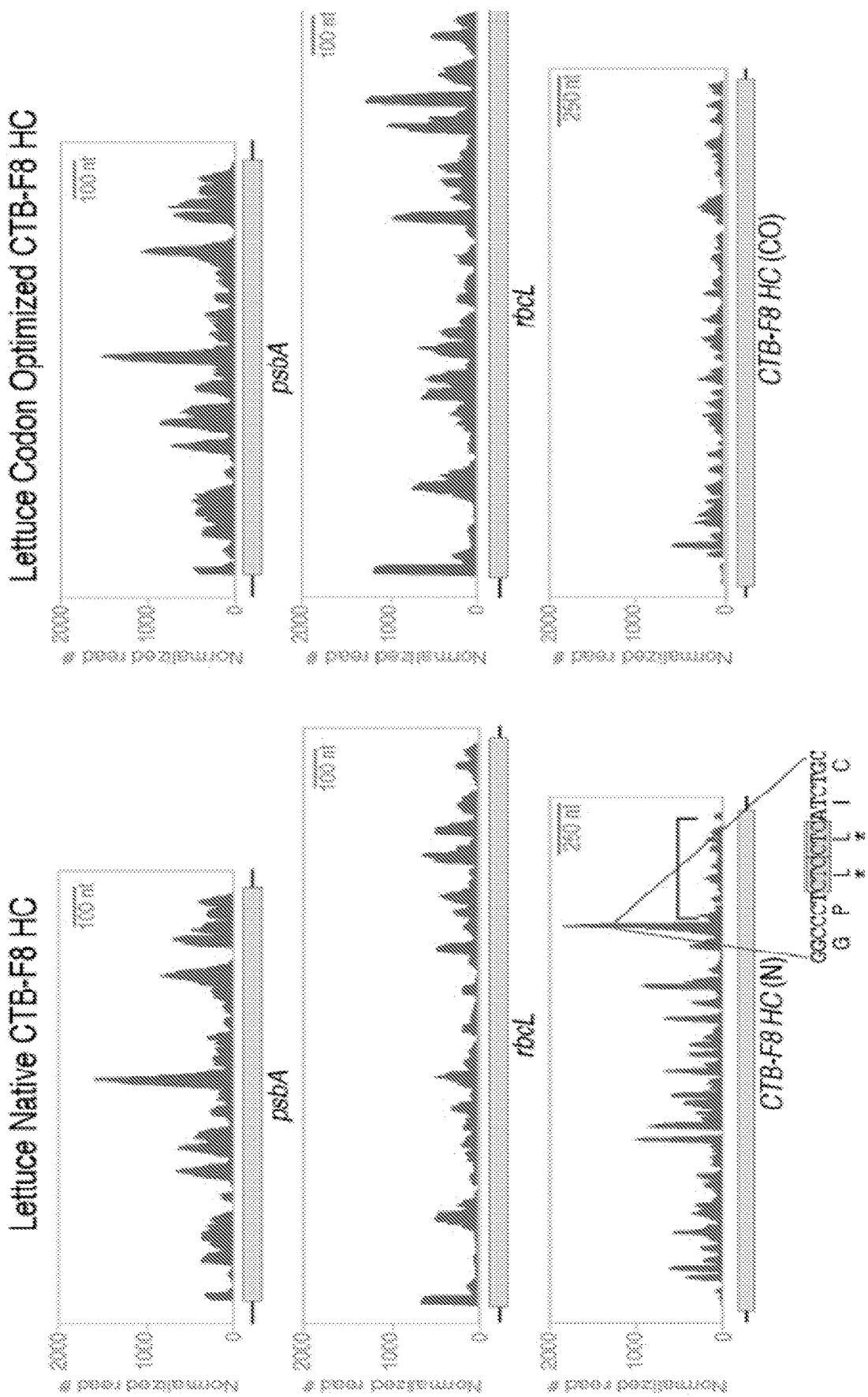

Codon usage in psbA (our program) is different for preferred Arg, Asn, Gly, His, Leu and Phe codons than those reported for 79 tobacco chloroplast mRNAs based on in vitro studies (Nakamura and Sugiura, 2007). Preferred codons are decoded more rapidly than non-preferred codons, presumably due to higher concentrations of the corresponding tRNAs that recognize the preferred codons, which speed up elongation rate of protein synthesis (Yu et al., 2015). Higher plant chloroplast genomes code for a conserved set of 30 tRNAs. This set is believed to be sufficient to support translation machinery in chloroplast (Lung et al., 2006). In the ribosome profiling data for codon optimized VP1, two major peaks representing presumed sites of ribosome stalling correlated with an unusually high concentration of serine codons (FIG. 8A). Five serine codons were clustered at codons 71, 73, 75, 76 and 79. And three other serine codons were found at codons 178, 179 and 182. Two adjacent serines in each cluster, (codons 75 and 76 (UCU-AGU), and codons 178 and 179 (UCC-UCU)) (see triangles in FIG. 8A) show a high level of ribosome stalling. Thus, further increases in expression of the codon-optimized VP1 transgene can be obtained by replacing these codons with codons for a different but similar amino acid.

In previous studies, codon modification to improve expression level of heterologous genes was focused on the increase of AT content by changing third nucleotide of codons. In case of IGF-1 (Daniell et al., 2009), the synthesized sequence of IGF-1 changed by $3^{rd}$ position of codons showed the dramatic fold increase of expression over the native sequence in E. coli system but no increase of expression level was observed in chloroplasts, suggesting that increase of AT content is not the major contributing factor in enhancing translation. As seen in this study, the AT content of codon optimized VP1 was marginally increased but the protein level of the optimized CTB-VP1 was dramatically increased up to 22.56~28.0 fold (by PRM) and 46-48 fold (by WB) over native sequence when expressed in chloroplasts. Therefore, several other factors play a key role in regulating efficiency of translation. As observed in ribosome profiling studies of CNTB-VP1, the availability and density of specific codons could severely impact translation. Similarly, FVIII HC, ribosome footprint results showed that ribosome pause was mapped to CTC leucine codons which are almost not used in psbA genes. The codon is also rarely used in lettuce rbcL gene (2.44%) and for tobacco rbcL, the codon is never used. Native FVIII HC uses the CTC codon as high as 15.28% but CTC codon was eliminated from the codon-optimized sequence according to psbA codon usage. More detailed analysis of codon frequency of the native FVIII HC and the psbA gene reveals further insight into rare codons; GGG for Gly is used 2.3% in psbA but 11.63% in HC native; CTG for Leu is 3.7% in psbA but 26.39% in HC native; CCC for Pro is 1.9% vs 11.9%; CGG for Arg is 0.5% vs 10.81%; CTG for Val is 1.7% vs 25.49%. So, similar to CTC codon, several other rare codons described above in the native human gene should have decreased translational efficiency in chloroplasts.

New Solution for Quantitation of Insoluble Multimeric Proteins

Figure 7B:
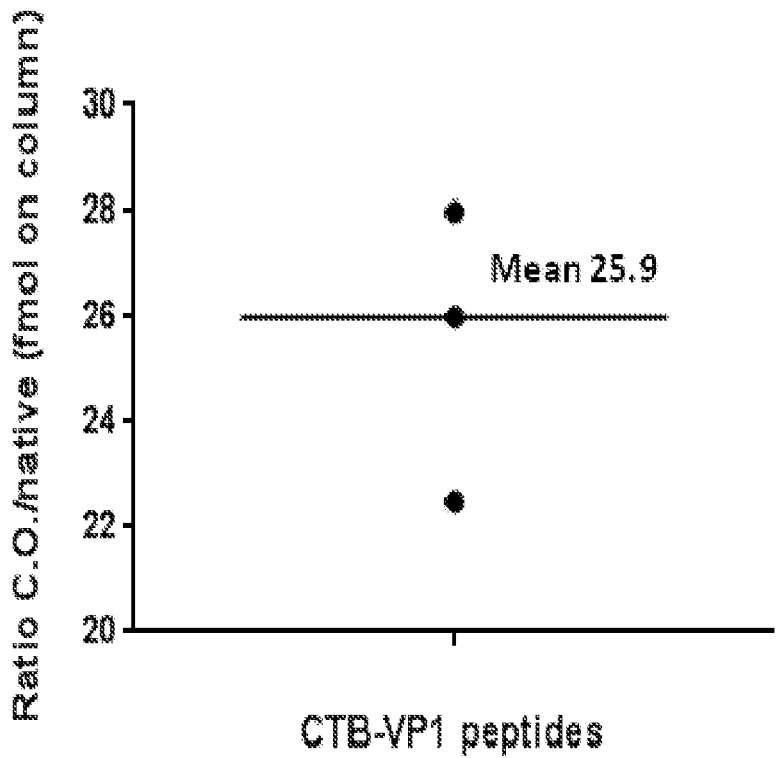

A major challenge is the lack of reliable methods to quantify insoluble proteins because the only reliable method (ELISA) can't be used due to aggregation or formation of multimeric structures. However, delivering accurate doses of protein drugs is a fundamental requirement for their clinical use. Therefore, in this study we carried out parallel reaction monitoring (PRM) analysis for absolute quantitation of CNTB-FVIII HC and CNTB-VP1 in plants carrying codon optimized and native sequences. PRM analysis has been broadly adopted in quantitative proteomics studies, e.g. biomarker discovery in plasma, due to its high sensitivity, specificity and precise quantitation of specific protein targets whiting complex protein matrices (Gallien et al., 2012). These qualities clearly show the advantage of using PRM in the quantification of specific protein targets, independently of the protein matrix source (e.g. plant extracts from tobacco or lettuce) or complexity. Moreover, the development of a PRM assay for hand full of proteins can be achieved in a relatively short time and at low costs (not taken in consideration the MS instrumentation). As a peptide-centric quantitation methodology also offers robustness and versatility of protein extraction methods and keeping the protein of interest in a native conformation is not required. However, it is intrinsically biased by the enzymatic cleavage site access of the enzymes used for digestion. In order to overcome this bias, we have used strong denaturing conditions (i.e. 2% SDS) and buffers that favor activity of the proteolytic enzymes (i.e. sodium deoxycholate based buffers) (Leon et al., 2013). For FVIII HC (FIGS. 6 and 7), there was no significant variations in the values for fold increases of codon-optimized over native sequences, which were determined by the peptides chosen for quantification. Three peptides selected from CNTB region (N-terminus of the fusion protein) showed that the range of the fold increase was from 4.9~6.4 while the range was 5.3~7.1 for the peptides chosen from FVIII regions (C-terminus of the fusion protein). So quantification results obtained from PRM analysis is consistent, irrespective of the selected region of the fusion protein (N or C-terminus) or the component protein (CNTB or FVIII HC). Also, the same three CNTB peptides for CNTBVP1 showed consistent in fold increase, ranging from 22.5~28.0. PRM analysis is better than western blots because it eliminated variations introduced by mobility and transfer of different size proteins and saturation of antibody probes. Overall, the PRM workflow consisted first on the selection of proteotypic peptides from CNTB and FVIII HC sequences; and synthesis of the counterpart SIS peptides. Six peptides were selected and scheduled for PRM analysis on the Qexactive mass spectrometer, based on observed retention time (RT) on the chromatography with a window of ±5 min and mass over charge (m/z) of double and/or triple charge state of these peptides. This double way of targeting the selection of precursor ions, in addition to the high resolution of the Qexactive MS, contributes to the high specificity of the assay. The PRM data analysis, post-acquisition, also offers a high specificity to the assay. The five most intense fragment ions, with no clear contaminant contribution from the matrix, are then selected for the quantification of the peptide. The confidence of the fragment ion assignment by the bioinformatics tool used, i.e. Skyline (MacLean et al., 2010) is finally achieved by the comparison of the reference MS/MS spectra and the RT profiles, generated with each of the counterpart SIS peptides. The high sensitivity, specificity, versatility and robustness of the PRM offer a new opportunity for characterizing translational systems in plants.

Conclusions

Heterologous gene expression utilizing chloroplast genome sequences, ribosome profiling and targeted mass spectrometry (MS) was analyzed to enhance our understanding of synthesis of valuable biopharmaceuticals in chloroplasts. Targeted Proteomic Quantification by Mass Spectrometry showed that codon optimization increases translation efficiency 5-50 fold based on the coding sequence, validating this approach for the first time for quantitation of protein drug dosage in plant cells. The lack of reliable methods to quantify insoluble proteins due to aggregation or formation of multimeric structures is a major challenge. Both biopharmaceuticals used in this study are CNTB fusion proteins that form pentamers, which is a requirement for their binding to intestinal epithelial GM1 receptors. Such a multimeric structure excluded the commonly used ELISA for quantitation of dosage. However, delivering accurate doses of protein drugs is a fundamental requirement for their clinical use and this important goal was accomplished in this study. Indeed plant biomass generated in this study has resulted in development of a polio booster vaccine, validated by the Center for Disease Control, a timely invention to meet World Health Organization requirement to withdraw current oral polio vaccine in April 2016, that cause severe polio in outbreak areas.

Such increase of codon-optimized protein accumulation is at the translational level rather than any impact on transcript abundance or stability. The codon-optimizer program increases transgene expression in chloroplasts in both tobacco and lettuce, with no species specificity. In contrast to previous in vitro studies, first in depth in vivo studies of heterologous gene expression using a wealth of newly sequenced chloroplast genomes facilitated the development of a new codon optimizer program which was tested using two important proteins for clinical applications. Ribosome foot prints obtained using profiling studies did not increase proportionately with VP1 translation or even decreased after FVIII codon optimization but it is a valuable tool for diagnosing rate limiting steps in translation. A major ribosome pause at CTC leucine codons, a rarely used codon in chloroplasts was eliminated from the native gene after codon optimization. Ribosome stalls observed at clusters of other codons in the codon-optimized genes provide opportunity for further optimization by eliminating the codons that cause such stalls.

REFERENCES

Arlen P A, Falconer R, Cherukumilli S, Cole A, Cole A M, Oishi K K, Daniell H (2007) Field production and functional evaluation of chloroplast-derived interferon-alpha2b. Plant Biotechnol J 5:511-525

Bally J, Nadal M, Vitel M, Rolland A, Dumain R, Dubald M (2009) Plant physiological adaptations to the massive foreign protein synthesis occurring in recombinant chloroplasts. Plant Physiol 150:1474-1481

Barkan A (1988) Proteins encoded by a complex chloroplast transcription unit are each translated from both monocistronic and polycistronic mRNAs. EMBO J 7:2637-2644

Boyhan D, Daniell H (2011) Low-cost production of proinsulin in tobacco and lettuce chloroplasts for injectable or oral delivery of functional insulin and C-peptide. Plant Biotechnol J 9:585-598

Birch-Machin I, Newell C A, Hibberd J M, Gray J C (2004) Accumulation of rotavirus VP6 protein in chloroplasts of transplastomic tobacco is limited by protein stability. Plant Biotechnol J 2:261-270

Chan H T, Daniell H (2015) Plant-made oral vaccines against human infectious diseases—Are we there yet? Plant Biotechnol J 13:1056-1070

Dniell H, Datta R, Varma S, Gray S, Lee S B (1998) Containment of herbicide resistance through genetic engineering of the chloroplast genome. Nat Biotechnol 16:345-348

Daniell H, Vivekananda J, Nielsen B L, Ye G N, Tewari K K, Sanford J C (1990) Transient foreign gene expression in chloroplasts of cultured tobacco cells after biolistic delivery of chloroplast vectors. Proc Natl Acad Sci USA 87:88-92

Daniell H, Ruiz G, Denes B, Sandberg L, Langridge W (2009) Optimization of codon composition and regulatory elements for expression of human insulin like growth factor-1 in transgenic chloroplasts and evaluation of structural identity and function. BMC Biotechnol 9:33

De Cosa B, Moar W, Lee S B, Miller M, Daniell H (2001) Overexpression of the Bt cry2Aa2 operon in chloroplasts leads to formation of insecticidal crystals. Nat Biotechnol 19:71-74

DeGray G, Rajasekaran K, Smith F, Sanford J, Daniell H (2001) Expression of an antimicrobial peptide via the chloroplast genome to control phytopathogenic bacteria and fungi. Plant Physiol 127:852-862

Domon B, Aebersold R (2010) Options and considerations when selecting a quantitative proteomics strategy. Nat Biotechnol 28:710-721

Eibl C, Zou Z, Beck A, Kim M, Mullet J, Koop H U (1999) In vivo analysis of plastid psbA, rbcL and rp132 UTR elements by chloroplast transformation: tobacco plastid gene expression is controlled by modulation of transcript levels and translation efficiency. Plant J 19:333-345

Gallien S, Duriez E, Crone C, Kellmann M, Moehring T, Domon B (2012) Targeted proteomic quantification on quadrupole-orbitrap mass spectrometer. Mol Cell Proteomics 11:1709-1723

Hassan S W, Waheed M T, Müller M, Clarke J L, Shinwari Z K, Loss' A G (2014) Expression of HPV-16 L1 capsomeres with glutathione-S-transferase as a fusion protein in tobacco plastids: an approach for a capsomere-based HPV vaccine. Hum Vaccin Immunother 10:2975-2982

Ingolia N T, Ghaemmaghami S, Newman J R, Weissman J S (2009) Genome-wide analysis in vivo of translation with nucleotide resolution using ribosome profiling. Science 324:218-223

Inka Borchers A M, Gonzalez-Rabade N, Gray J C (2012) Increased accumulation and stability of rotavirus VP6 protein in tobacco chloroplasts following changes to the 5' untranslated region and the 5' end of the coding region. Plant Biotechnol J 10:422-434

Jabeen R, Khan M S, Zafar Y, Anjum T (2010) Codon optimization of cry1Ab gene for hyper expression in plant organelles. Mol Biol Rep 37:1011-1017

Jin S, Daniell H (2015) The Engineered Chloroplast Genome Just Got Smarter. Trends Plant Sci 20:622-640

Kane J F (1995) Effects of rare codon clusters on high-level expression of heterologous proteins in *Escherichia coli*. Curr Opin Biotechnol 6:494-500

Kohli N, Westerveld D R, Ayache A C, Verma A, Shil P, Prasad T, Zhu P, Chan S L, Li Q, Daniell H (2014) Oral delivery of bioencapsulated proteins across blood-brain and blood-retinal barriers. Mol Ther 22:535-546

Kwon K C, Nityanandam R, New J S, Daniell H (2013a) Oral delivery of bioencapsulated exendin-4 expressed in chloroplasts lowers blood glucose level in mice and stimulates insulin secretion in beta-TC6 cells. Plant Biotechnol J 11:77-86

Lakshmi P S, Verma D, Yang X, Lloyd B, Daniell H (2013) Low cost tuberculosis vaccine antigens in capsules: expression in chloroplasts, bio-encapsulation, stability and functional evaluation in vitro. PLoS One 8:e54708

Lee S B, Li B, Jin S, Daniell H (2011) Expression and characterization of antimicrobial peptides Retrocyclin-101 and Protegrin-1 in chloroplasts to control viral and bacterial infections. Plant Biotechnol J 9:100-115

Lenzi P, Scotti N, Alagna F, Tornesello M L, Pompa A, Vitale A, De Stradis A, Monti L, Grillo S, Buonaguro F M, Maliga P, Cardi T (2008) Translational fusion of chloroplast-expressed human papillomavirus type 16 L1 capsid protein enhances antigen accumulation in transplastomic tobacco. Transgenic Res. 17:1091-1102.

Leon I R, Schwämmle V, Jensen O N, Sprenger R R (2013) Quantitative assessment of in-solution digestion efficiency identifies optimal protocols for unbiased protein analysis. Mol Cell Proteomics 12:2992-3005

Lung B, Zemann A, Madej M J, Schuelke M, Techritz S, Ruf S, Bock R, Hüttenhofer A (2006) Identification of small non-coding RNAs from mitochondria and chloroplasts. Nucleic Acids Res 34:3842-3852

McCabe M S, Klaas M, Gonzalez-Rabade N, Poage M, Badillo-Corona J A, Zhou F, Karcher D, Bock R, Gray J C, Dix P J (2008) Plastid transformation of high-biomass tobacco variety Maryland Mammoth for production of human immunodeficiency virus type 1 (HIV-1) p24 antigen. Plant Biotechnol J 6:914-929

MacLean B, Tomazela D M, Shulman N, Chambers M, Finney G L, Frewen B, Kern R, Tabb D L, Liebler D C, MacCoss M J (2010) Skyline: an open source document editor for creating and analyzing targeted proteomics experiments. Bioinformatics 26:966-968

Nakamura, M. and Sugiura, M (2007) Translation efficiencies of synonymous codons are not always correlated with codon usage in tobacco chloroplasts. Plant J 49:128-134

Quesada-Vargas T, Ruiz O N, Daniell H (2005) Characterization of heterologous multigene operons in transgenic chloroplasts: transcription, processing, and translation. Plant Physiol 8:1746-1762

Rosenberg A H, Goldman E, Dunn J J, Studier F W, Zubay G (1993) Effects of consecutive AGG codons on translation in *Escherichia coli*, demonstrated with a versatile codon test system. J Bacteriol 175:716-722

Ruhlman T, Verma D, Samson N, Daniell H (2010) The role of heterologous chloroplast sequence elements in transgene integration and expression. Plant Physiol 152:2088-2104

Shenoy V, Kwon K C, Rathinasabapathy A, Lin S, Jin G, Song C, Shil P, Nair A, Qi Y, Li Q, Francis J, Katovich M J, Daniell H, Raizada M K (2014) Oral delivery of Angiotensin-converting enzyme 2 and Angiotensin-(1-7) bioencapsulated in plant cells attenuates pulmonary hypertension. Hypertension 64:1248-1259

Sherman A, Su J, Lin S, Wang X, Herzog R W, Daniell H (2014) Suppression of inhibitor formation against FVIII in a murine model of hemophilia A by oral delivery of antigens bioencapsulated in plant cells. Blood 124:1659-1668

Shil P K, Kwon K C, Zhu P, Verma A, Daniell H, Li Q (2014) Oral delivery of ACE2/Ang-(1-7) bioencapsulated in plant cells protects against experimental uveitis and autoimmune uveoretinitis. Mol Ther 22:2069-2082

Verma D, Moghimi B, LoDuca P A, Singh H D, Hoffman B E, Herzog R W, Daniell H (2010) Oral delivery of bioencapsulated coagulation factor IX prevents inhibitor formation and fatal anaphylaxis in hemophilia B mice. Proc Natl Acad Sci USA 107:7101-7106

Verma D, Samson N P, Koya V, Daniell H (2008) A protocol for expression of foreign genes in chloroplasts. Nat Protoc 3:739-758

Waheed M T, Thönes N, Müller M, Hassan S W, Gottschamel J, Loss' E, Kaul H P, Loss' A G (2011a) Plastid expression of a double-pentameric vaccine candidate containing human papillomavirus-16 L1 antigen fused with LTB as adjuvant: transplastomic plants show pleiotropic phenotypes. Plant Biotechnol J 9:651-660

Waheed M T, Thones N, Müller M, Hassan S W, Razavi N M, Loss' E, Kaul H P, Loss' A G (2011b) Transplastomic expression of a modified human papillomavirus L1 protein leading to the assembly of capsomeres in tobacco: a step towards cost-effective second-generation vaccines. Transgenic Res 20:271-282

Wang X, Su J, Sherman A, Rogers G L, Liao G, Hoffman B E, Leong K W, Terhorst C, Daniell H, Herzog R W (2015) Plant-based oral tolerance to hemophilia therapy employs a complex immune regulatory response including LAP+ CD4+ T cells. Blood 125:2418-2427

Ye G N, Hajdukiewicz P T J, Broyles D, Rodriquez D, Xu C W, Nehra N, Staub J M (2001) Plastid-expressed 5-enolpyruvylshikimate-3-phosphate synthase genes provide high level glyphosate tolerance in tobacco. Plant J 25:261-270

Yu C H, Dang Y, Zhou Z, Wu C, Zhao F, Sachs M S, Liu Y (2015) Codon usage influences the local rate of translation elongation to regulate co-translational protein folding. Mol Cell 59:744-754

Zoschke R, Barkan A (2015) Genome-wide analysis of thylakoid-bound ribosomes in maize reveals principles of cotranslational targeting to the thylakoid membrane. Proc Natl Acad Sci USA 112:E1678-87

Zoschke R, Watkins K P, Barkan A (2013) A rapid ribosome profiling method elucidates chloroplast ribosome behavior in vivo. Plant Cell 25:2265-2275

Burns, C. C., Diop, O. M., Sutter, R. W. & Kew, O. M. Vaccine-derived polioviruses. J. Infect. Dis. 210 (Suppl. 1), S283-S293 (2014).

Famulare, M. & Hu, H. Extracting transmission networks from phylogeographic data for epidemic and endemic diseases: Ebola virus in Sierra Leone, 2009 H1N1 pandemic influenza and polio in Nigeria. Int. Health 7, 130-138 (2015).

Burns, C. C. et al. Multiple independent emergences of type 2 vaccine-derived polioviruses during a large outbreak in northern Nigeria. J. Virol. 87, 4907-4922 (2013).

Laxmivandana, R., Yergolkar, P., Gopalkrishna, V. & Chitambar, S. D. Characterization of the non-polio enterovirus infections associated with acute flaccid paralysis in South-Western India. PLoS One 8, e61650 (2013).

Dhole, T. N. et al. Non-polio enteroviruses in acute flaccid paralysis children of India: vital assessment before polio eradication. J. Paediatr. Child. Health 45, 409-413 (2009).

Brown, B., M. S. Oberste, K. Maher, & M. A. Pallansch. Complete genomic sequencing shows that polioviruses and members of human enterovirus species C are closely related in the noncapsid coding region. J. Virol. 77, 8973-8984 (2003).

Rakoto-Andrianarivelo, M. et al. High frequency of human enterovirus species C circulation in Madagascar. J. Clin. Microbiol. 43, 242-249 (2005).

Adeniji, J. A. & Faleye, T. O. Enterovirus C strains circulating in Nigeria and their contribution to the emergence of recombinant circulating vaccine-derived polioviruses. Arch. Virol. 160, 675-683 (2015).

Jiang, P. et al. Evidence for emergence of diverse polioviruses from C-cluster coxsackie A viruses and implications for global poliovirus eradication. Proc. Natl. Acad. Sci. USA 104, 9457-9462 (2007).

Kouiayskaia, D. et al. Intradermal inactivated poliovirus vaccine: a preclinical dose-finding study. J. Infect. Dis. 211, 1447-1450 (2015).

Parker, E. P., Molodecky, N. A., Pons-Salort, M., O'Reilly, K. M. & Grassly, N. C. Impact of inactivated poliovirus vaccine on mucosal immunity: implications for the polio eradication endgame. Expert Rev. Vaccines 14, 1113-1123 (2015).

Chan, H. T. & Daniell, H. Plant-made oral vaccines against human infectious diseases—Are we there yet? Plant Biotechnol. J. 13, 1056-1070 (2015).

Xiao, Y. et al. Low cost delivery of proteins bioencapsulated in plant cells to human non-immune or immune modulatory cells. Biomaterials doi:10.1016/j.biomaterials.2015.11.051 (2015).

Jin, S. & Daniell, H. The engineered chloroplast genome just got smarter. Trends Plant Sci. 20, 622-640 (2015).

Kwon, K. C., Verma, D., Singh, N. D., Herzog, R. & Daniell H. Oral delivery of human biopharmaceuticals, autoantigens and vaccine antigens bioencapsulated in plant cells. Adv. Drug Deliv. Rev. 65, 782-799 (2013).

Kong., Q. et al. Oral immunization with hepatitis B surface antigen expressed in transgenic plants. Proc. Natl. Acad. Sci. USA 98, 11539-11544 (2001).

Thanavala, Y. et al. Immunogenicity in humans of an edible vaccine for hepatitis B. Proc. Natl. Acad. Sci. USA 102, 3378-3382 (2005).

Rybicki, E. P. Plant-based vaccines against viruses. Virol. J. 11, 205-224 (2014).

Ruhlman, T., Ahangari, R. Devine, A. Samsam, M. & Daniell H. Expression of cholera toxin B-proinsulin fusion protein in lettuce and tobacco chloroplasts-oral administration protects against development of insulitis in non-obese diabetic mice. Plant Biotechnol. J. 5, 495-510 (2007).

Verma, D., Samson, N. P., Koya, V. & Daniell, H. A protocol for expression of foreign genes in chloroplasts. Nat. Protoc. 3, 739-758 (2008).

Kanagaraj, A. P., Verma, D. & Daniell H. Expression of dengue-3 premembrane and envelope polyprotein in lettuce chloroplasts. Plant Mol. Biol. 76, 323-333 (2011).

Domingos, M. de O. et al. A new oil-based antigen delivery formulation for both oral and parenteral vaccination. Open Drug Deliv. J. 2, 52-60 (2008).

Lee, G. et al. Oral immunization of haemaggulutinin H5 expressed in plant endoplasmic reticulum with adjuvant saponin protects mice against highly pathogenic avian influenza A virus infection. Plant Biotechnol. J. 13, 62-72 (2015).

Frey, A., Di Canzio & J., Zurakowski, D. A statistically defined endpoint titer determination method for immunoassays. J. Immunol. Methods 221, 35-41 (1998).

Dietrich, J., Andreasen, L. V., Andersen, P. & Agger, E. M. Inducing dose sparing with inactivated polio virus formulated in adjuvant CAF01. PLoS One 9, e100879 (2014).

Example II

Cold Chain and Virus Free Plant-made Booster Vaccine to Confer Immunity Against Different Polio Virus Serotypes Construction of Plant Transformation Vectors Two VP1 proteins derived from Sabin 1 coding sequences (CDS) were expressed in tobacco and lettuce chloroplasts. See FIG. 4A. The first sequence encompassed the native 906-bp VP1 sequence (51.98% AT) fused with the transmucosal carrier CTB. The second was codon-optimized for expression in tobacco and lettuce chloroplasts as described in Example I. Of the 302 amino acids in the protein, 187 codons were optimized by changing the codon usage frequency to resemble that of the chloroplast psbA gene (the most highly translated chloroplast gene). Rare codons were replaced with optimal codons for transgene expression in chloroplasts and the AT content of the optimized VP1 gene increased from 51.98% to 59.03%. Both CTB-VP1 fusion genes were constructed with a GPGP (Gly-Pro-Gly-Pro) (SEQ ID NO: 13) hinge region to minimize steric hindrance of the fused VP1, as well as a furin cleavage site, RRKRSV (Arg-Arg-Lys-Arg-Ser-Val) (SEQ ID NO: 14) (FIG. 10A). The fusion gene was driven by the psbA promoter and 5' untranslated region (UTR) to increase expression, and the transcript was stabilized by the psbA 3'-UTR.

Integration of Foreign Genes into Tobacco and Lettuce Plastomes

Figure 9A:
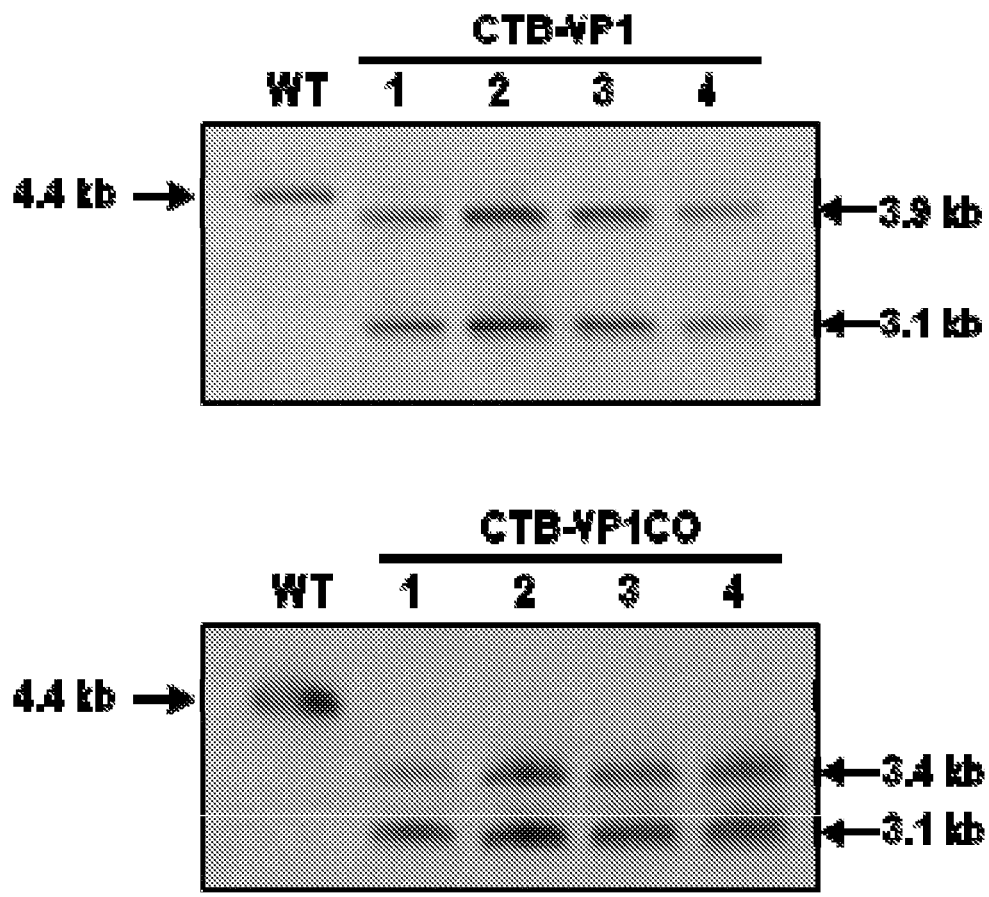
FIGS. 9A-9D: Creation and characterization of transplastomic tobacco and lettuce lines expressing native and codon-optimized CTB-VP1.
Figure 9B:
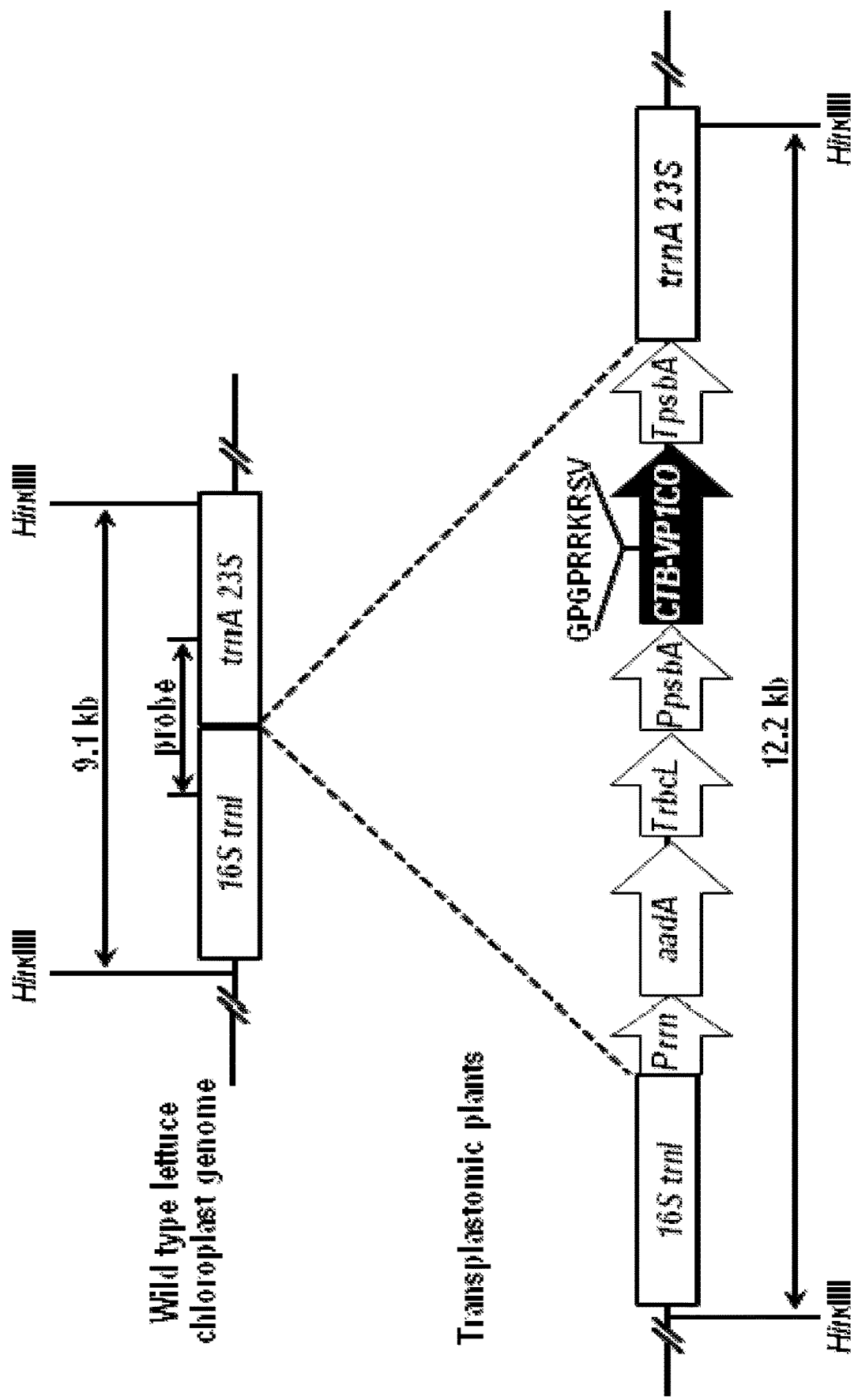
Figure 9C:
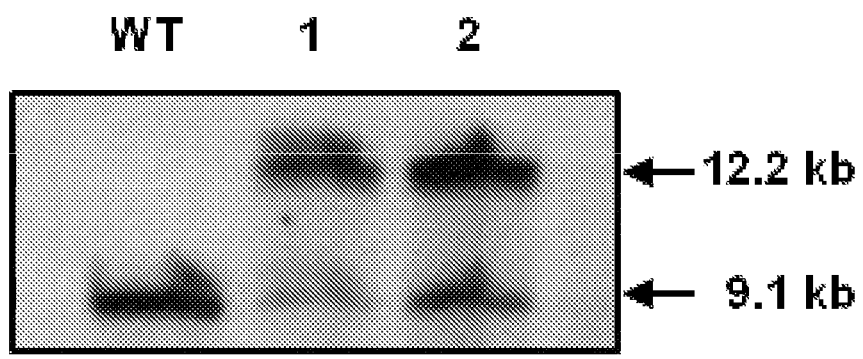
Figure 9D:
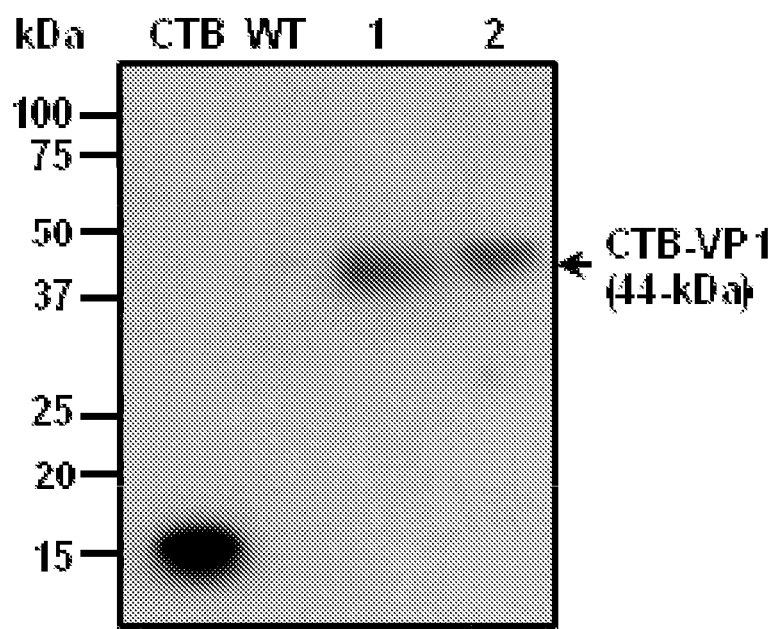

CTB-VP1 transplastomic lines were generated by biolistic particle bombardment. After selection on spectinomycin-containing media, putative transplastomic lines were confirmed by PCR analysis with primer sets 3P/3M and 5P/2M for tobacco or 16S-Fw/3M and 5P/2M for lettuce (data not shown). Targeted integration and homoplasmy of the CTB-VP1 gene was further verified by Southern blot probed with the trnI and trnA flanking sequence (FIG. 9B). All independent transplastomic tobacco lines showed distinct hybridization fragments with the correct size, but not the 4.4-kb fragment from wild type in the AflIII-digested total DNA blot (FIG. 9A). Transplastomic lettuce lines showed a hybridizing fragment of expected size of 12.2 kb but also the 9.1-kb fragment from untransformed wild type plants, indicating heteroplasmy. However, after 2 rounds of selection, transplastomic lettuce line 1 almost reached homoplasmy (FIGS. 9C and 9D). Thus Southern blot analysis confirmed the site-specific stable integration of the transgenes into the chloroplast genome and transgene homoplasmy. As shown in FIG. 9D, lettuce-derived CTB-VP1 was detected with the correct molecular mass of 44 kDa.

Folding, Stability and CTB-VP1 Pentamer Assembly in Lyophilized Tobacco Leaves

Figure 10:
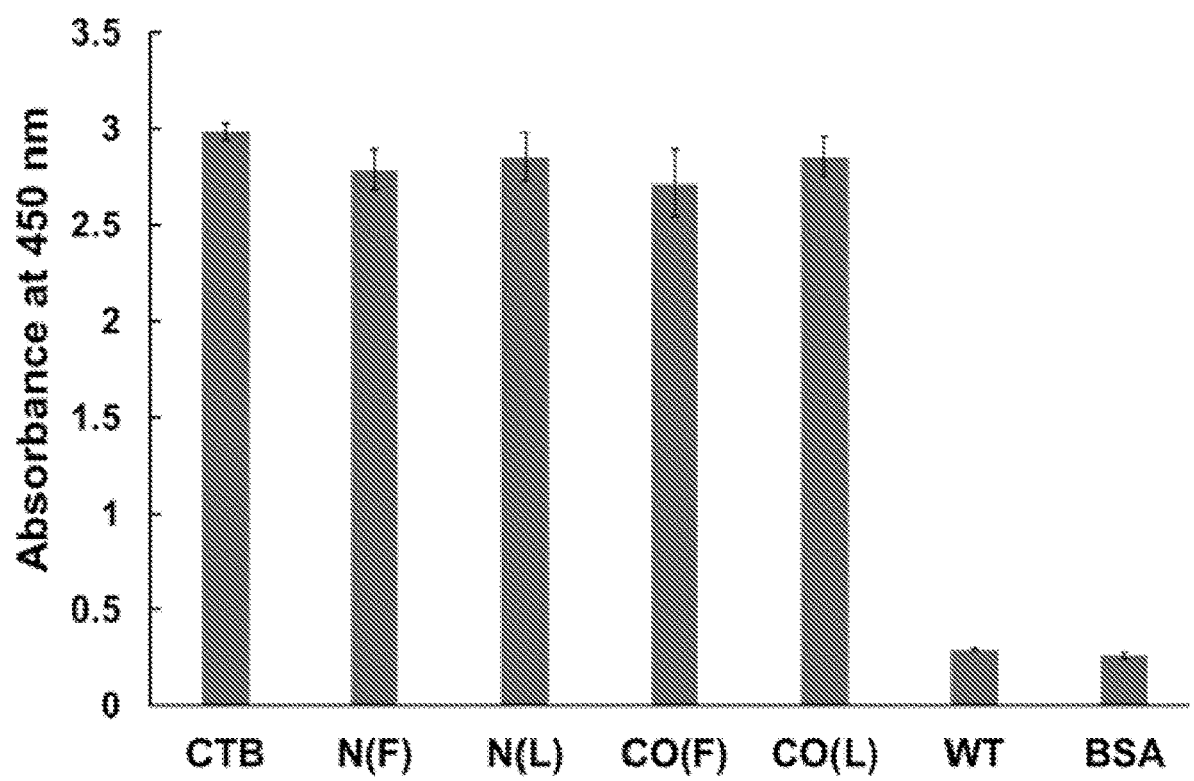
Figures 11A, 11B, 11C:
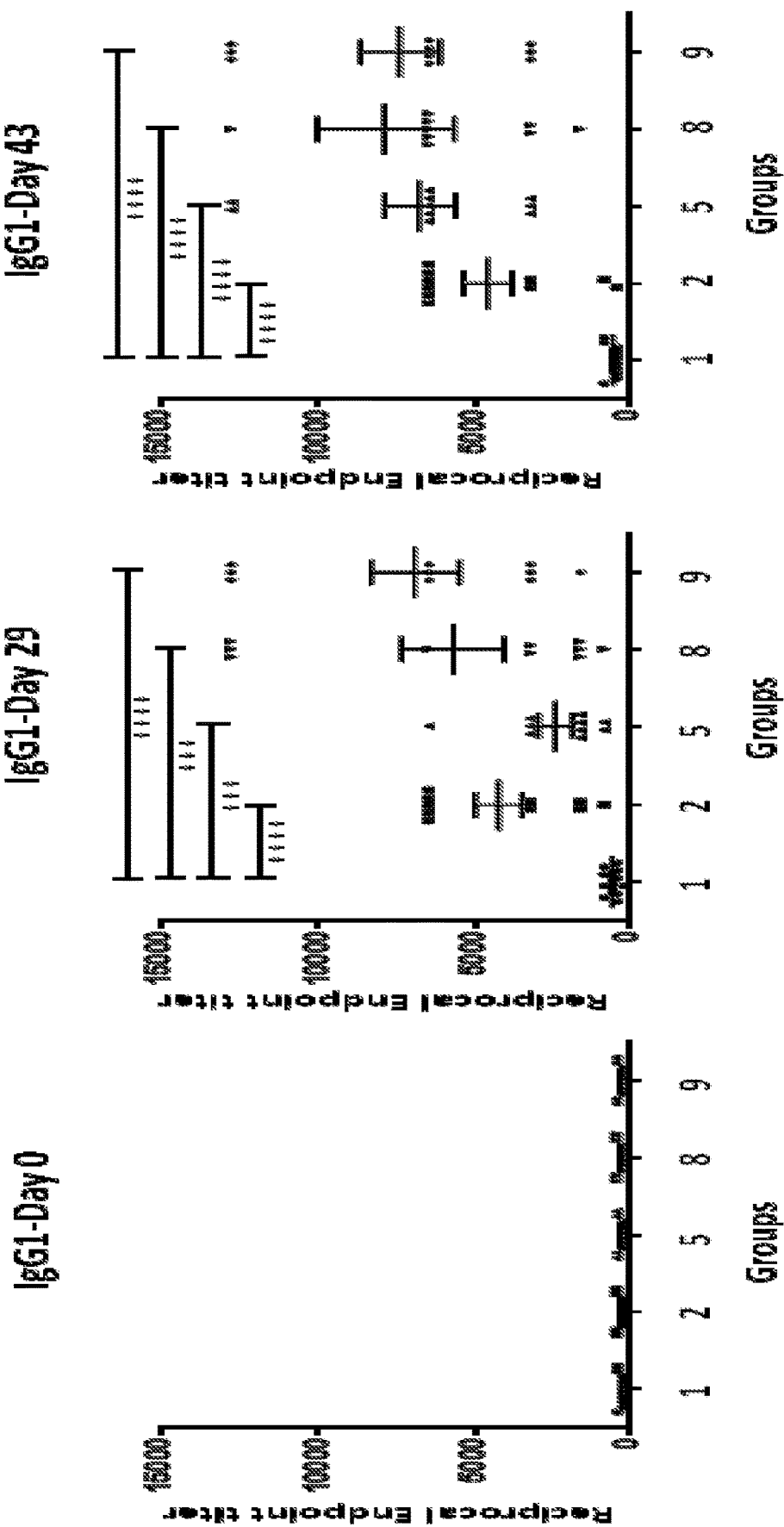
Figures 11D, 11E, 11F:
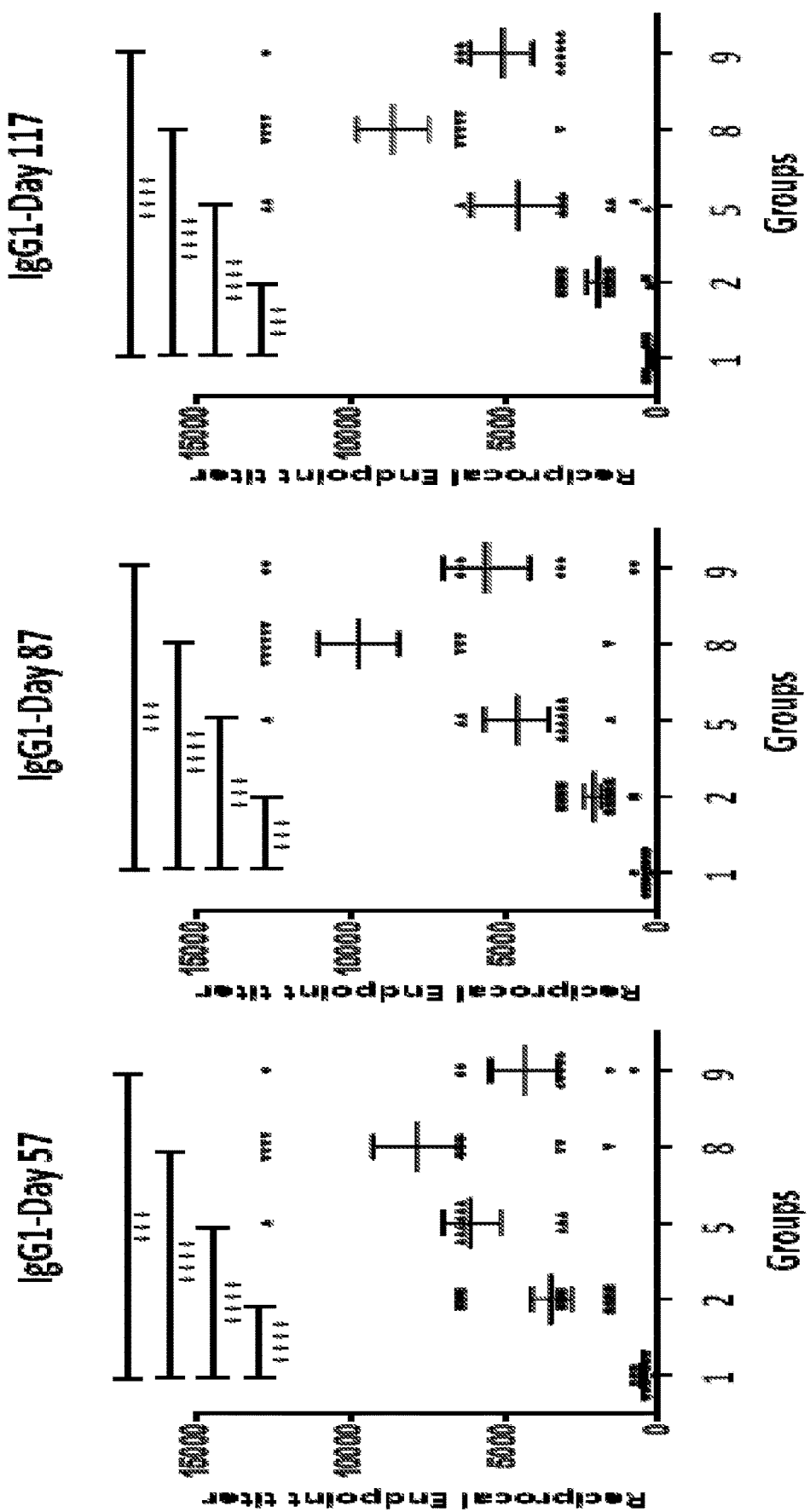
Figure 11H:
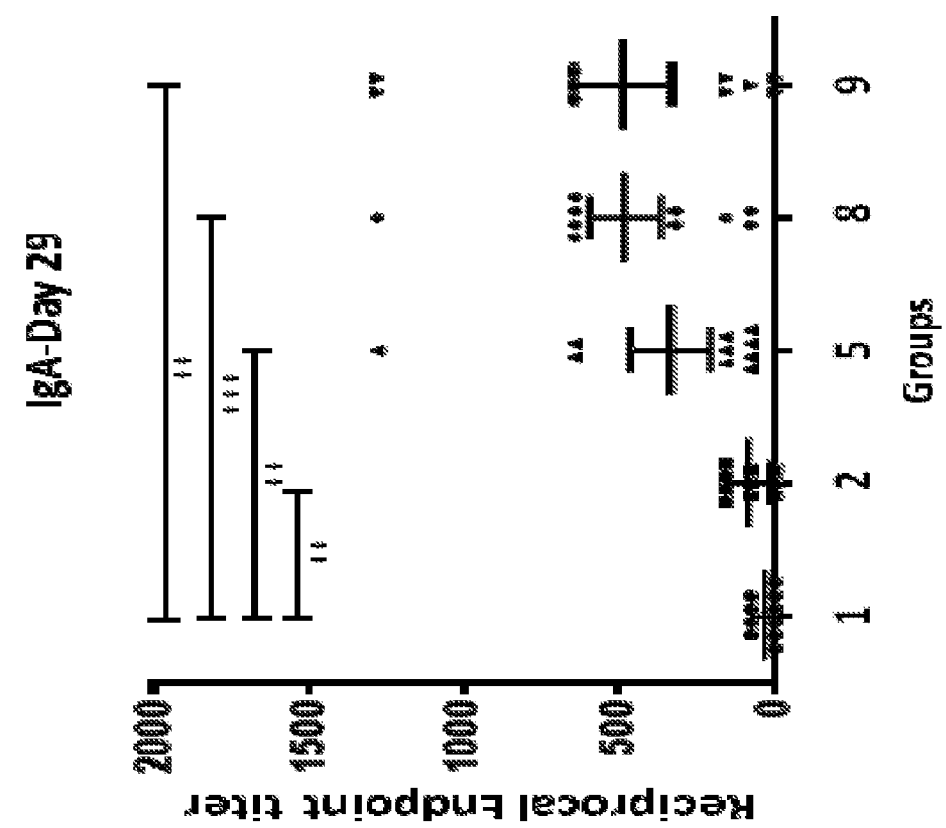
Figure 11G:
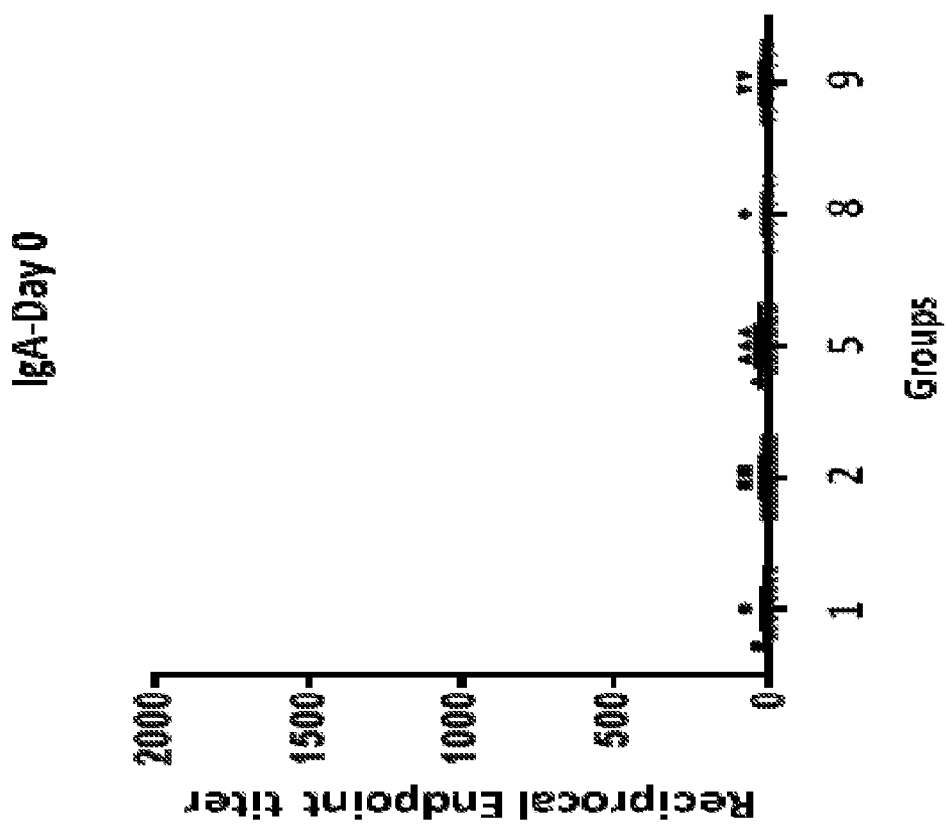
Figure 11J:
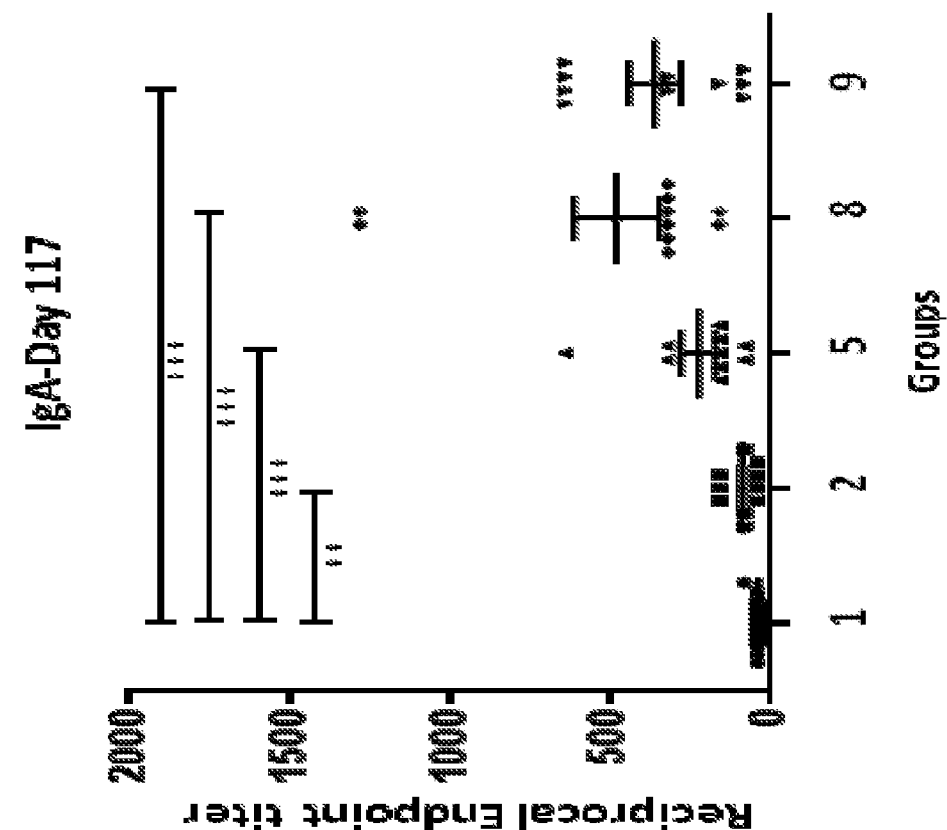
Figure 11I:
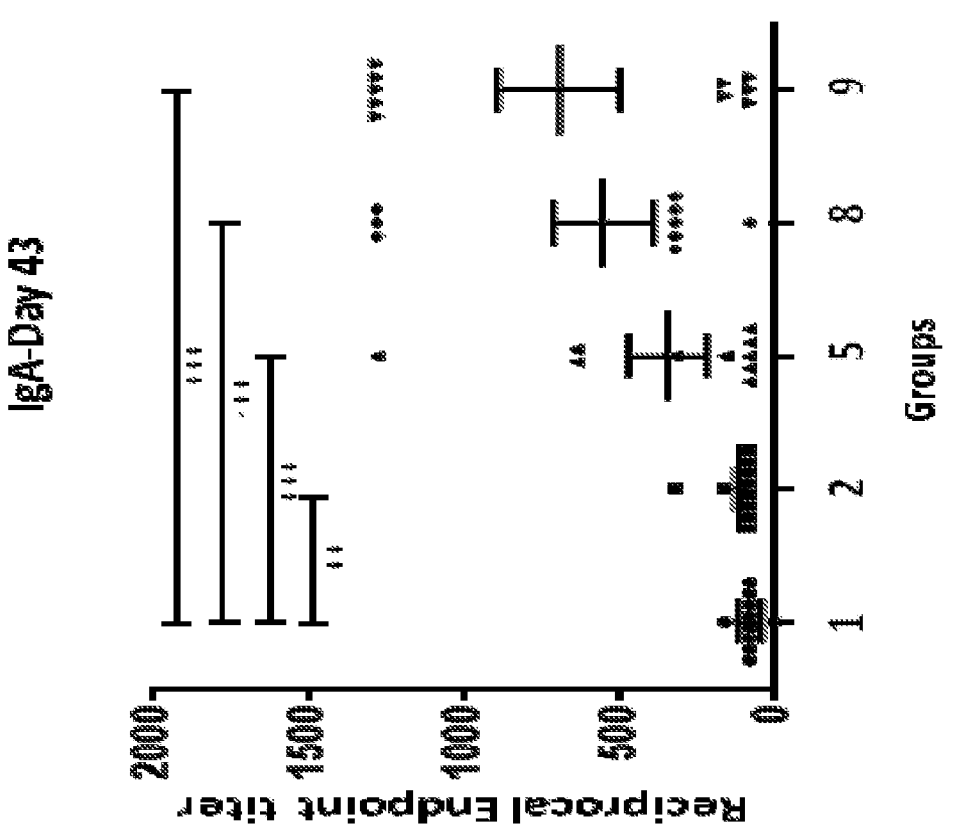

CTB-VP1 accumulation in transplastomic plants was quantified by western blot analysis. Intensities of CTB-VP1 protein in the bands in native and codon-optimized plants were compared with known amounts of CTB standard. The western blot analysis indicated that the codon-optimized VP1 sequence significantly increased accumulation of CTB-VP1 when compared with the native VP1 gene product. Native and codon-optimized CTB-VP1 reached up to 0.1% and 4-5% of the total leaf protein, respectively (up to 100-fold increase based on quantitation using targeted MS or western blots, data not shown). As shown in FIG. 9D, the monomer CTB-VP1 fusion protein with the correct molecular mass of 44 kDa was detected with anti-CTB or VP1 antibody. CTB-VP1 antigen increased ~20-fold in lyophilized cells when compared with frozen leaf samples. The intact monomer band of CTB-VP1 fusion proteins was observed without any detectable degradation of CTB-VP1 in all tested lyophilized samples after storage for 4 and 8 months at ambient temperature. Formation of pentameric structures of the CTB-VP1 expressed in chloroplasts was evaluated using GM1 binding ELISA assays. As shown in FIG. 10, both native and codon-optimized fresh and lyophilized CTB-VP1 from tobacco showed comparable absorbance to CTB (positive control), whereas no signals were detected from wild type plants or BSA (negative controls). This indicates that CTB-VP1 fusion protein expressed in both fresh and lyophilized chloroplasts formed proper pentameric structures that could bind the GM1-ganglioside receptor, which is a requirement for protein drug delivery. The stability of VP1, efficacy of binding to GM1-ganglioside receptor, proper folding and pentamer assembly were maintained after lyophilization and prolonged storage for eight months at ambient temperature.

Animal Vaccination and Antibody Responses to VP1

Plant-derived subunit vaccines are heat-stable and are free from contamination with animal pathogens. They can also be engineered to contain multiple antigens and transmucosal carrires, to protect against multiple infectious diseases. Such mechanistic and conceptual advances could revolutionize vaccine delivery by eliminating the cost of complex production systems, such as fermentation, purification, cold storage and transportation. Two major challenges to plant based vaccine production include the low levels of expression of antigens via the nuclear genome and the potential to induce tolerance without injectable priming of antigens with adjuvants.

In order to address inadequacies of the current OPV, including poor vaccine efficacy, instability and reversion to neuro-virulence, shedding of circulating vaccine-derived polio viruses, and the high cost and inadequate mucosal immunity of inactivated poliovirus vaccine (IPV), a low-cost booster vaccine has been developed in this study using polio viral antigen bioencapsulated in plant cells. The strategy of using a plant-made viral protein 1 (VP1) subunit vaccine for an oral booster rather than repeated OPV vaccination is a novel approach to achieve the goal of global PV eradication. In this study, we provide evidence that oral boosting with chloroplast-derived VP1 together with plant-made adjuvants (saponin and squalene) induces strong immune responses that confer protective immunity against different PV serotypes.

In the previous example, we describe lyophilized CTB-VP1 protein. In the present example, this protein was formulated with plant-derived adjuvants (saponin and/or squalene) which induce specific antibody immunogenicity and neutralize different polio virus serotypes. Mice were divided into groups as described in the Methods section and in the Table below.

| Group | Number of mice | Prime | Boost with IPV (s.c) or VP1 (oral) |
|---|---|---|---|
| 1 | 10 | N/A | N/A |
| 2 | 10 | IPV | IPV |
| 3 | 10 | IPV | N/A |
| 4 | 10 | IPV | VP1 1 µg/ Saponin |
| 5 | 10 | IPV | VP1 1 µg/Squalene |
| 6 | 10 | IPV | VP1 1 µg/Saponin/Squalene |
| 7 | 10 | IPV | VP1 25 µg/Saponin |
| 8 | 10 | IPV | VP1 25 µg/Squalene |
| 9 | 10 | IPV | VP1 25 µg/Saponin/Squalene |
| 10 | 10 | N/A | VP1 25 µg Saponin/Squalene |

Construction of Plant Transformation Vectors

Two VP1 proteins derived from Sabin 1 coding sequences (CDS) were expressed in tobacco chloroplasts. The first sequence encompassed the native 906-bp VP1 sequence (51.98% AT) fused with the transmucosal carrier CTB. The second was codon-optimized for expression in tobacco and lettuce chloroplasts. Of the 302 amino acids in the protein, 187 codons were optimized by changing the codon usage frequency to resemble that of the chloroplast psbA gene (the most highly translated chloroplast gene). Rare codons were replaced with optimal codons for transgene expression in chloroplasts and the AT content of the optimized VP1 gene increased from 51.98% to 59.03%. Both CTB-VP1 fusion genes were constructed with a GPGP (Gly-Pro-Gly-Pro) hinge region to minimize steric hindrance of the fused VP1, as well as a furin cleavage site, RRKRSV (Arg-Arg-Lys-Arg-Ser-Val) (SEQ ID NO: 14) (FIG. 4A and FIG. 9B). The fusion gene was driven by the psbA promoter and 5' untranslated region (UTR) to increase expression, and the transcript was stabilized by the psbA 3'-UTR.

Animal Vaccination and Antibody Responses to VP1

As mentioned above, mice were divided into groups as set forth in the table above. One day prior to immunization, mice from all groups were bled. We determined serum titers of VP1-specific IgG1 and IgA antibodies at various time points on days 29, 43, 57, 87 and 117 after boosting with IPV or CTB-VP1 with adjuvants. At all tested time points, systemic and mucosal immune responses were quantified with ELISA. VP1-IgG1 titers reached highest levels in the first month and remained at the same level. Further boosting did not increase VP1-IgG1 levels (See FIG. 11). Mice boosted with codon-optimized CTB-VP1 plus both adjuvants also had higher anti-VP1 IgG1 antibody titers than those boosted with IPV (group 9, see FIG. 11B-F). Similarly, VP1-IgA titers increased after oral boosting in the first month and subsequent boosting resulted in marginal increase in IgA titers (FIG. 11G-J). In sharp contrast, IPV boosting did not increase IgA titers, confirming limitation of systemic vaccine delivery. These results show that oral boosting with plant cells expressing CTB-VP1 can induce both mucosal and systemic immune responses whereas IPV prime/boost developed lower levels of IgG1 and negligible IgA titers.

Furthermore, vaccination with codon-optimized VP1 induced significantly higher serum titers of specific anti-VP1 IgG1 and IgA, showing that high expression of antigen in lyophilized codon-optimized material is critical for effective immunization. Moreover, boosting with either native or codon-optimized VP1 antigens combined with two adjuvants (groups 5, 8 and 9) induced stronger IgG1 and IgA immune responses than with either one adjuvant, suggesting that plant-derived adjuvants enhance delivering antigens via the mucosal rote and developing strong mucosal and systemic immune responses.

Figure 12A:
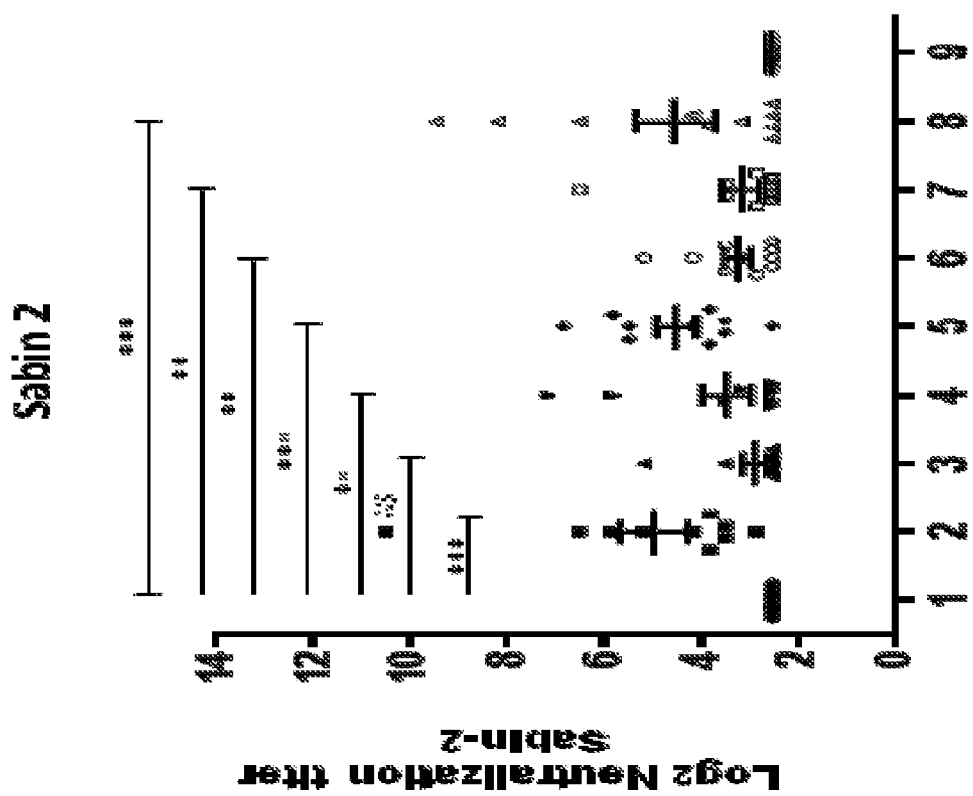
Figure 12B:
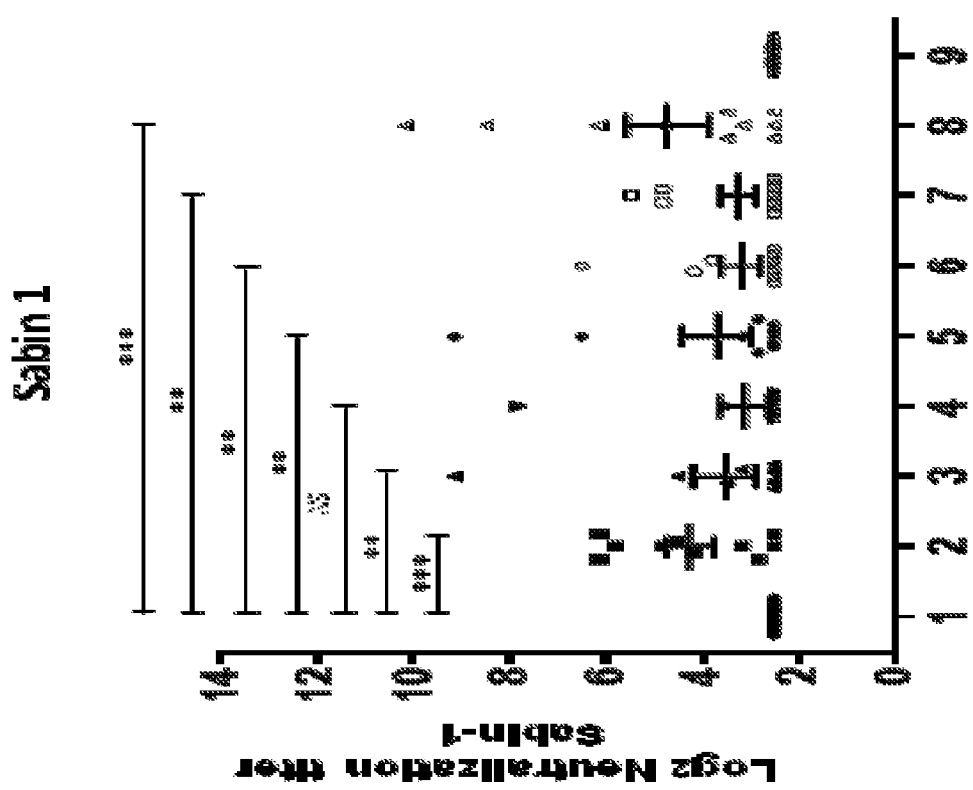
Figure 12C:
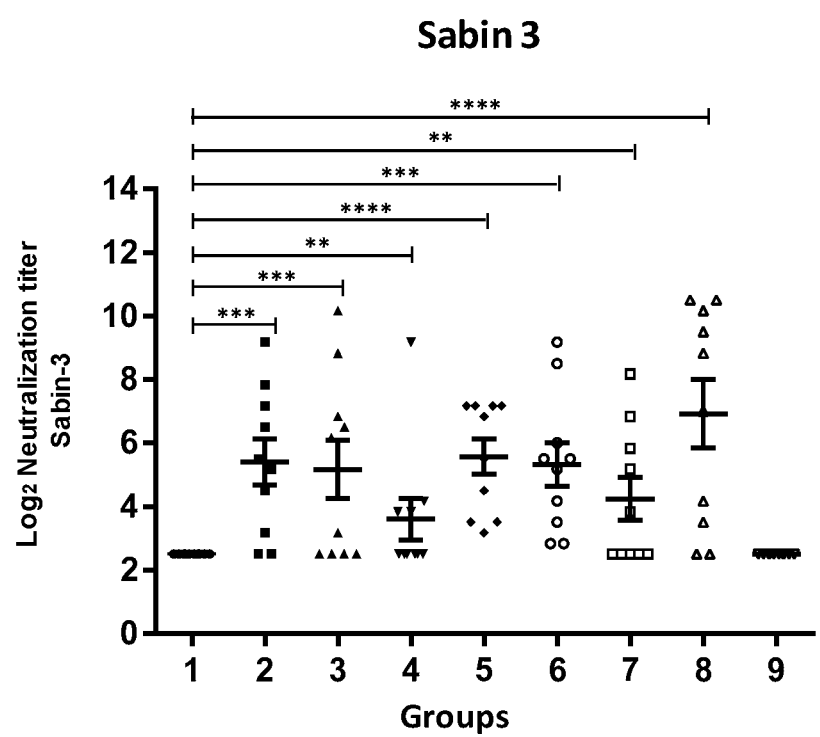
Figure 13A:
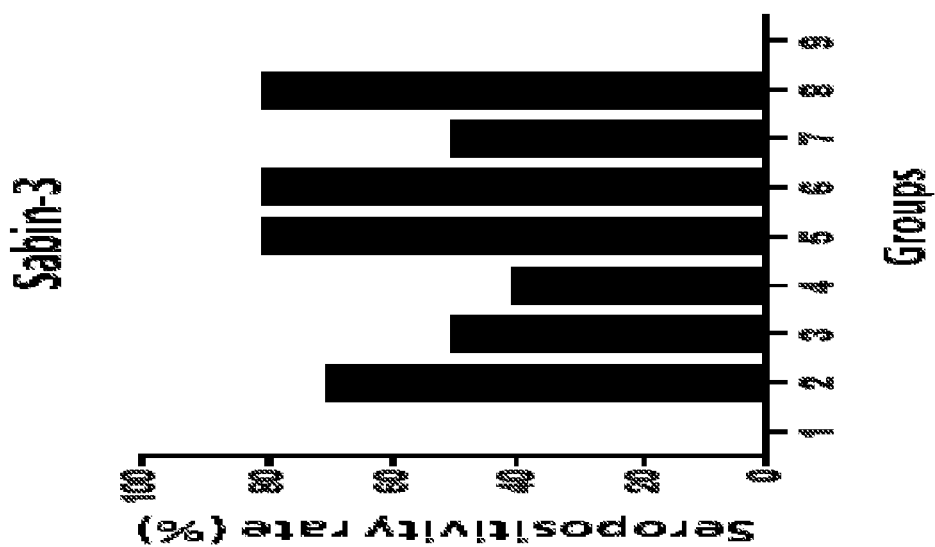
Figure 13B:
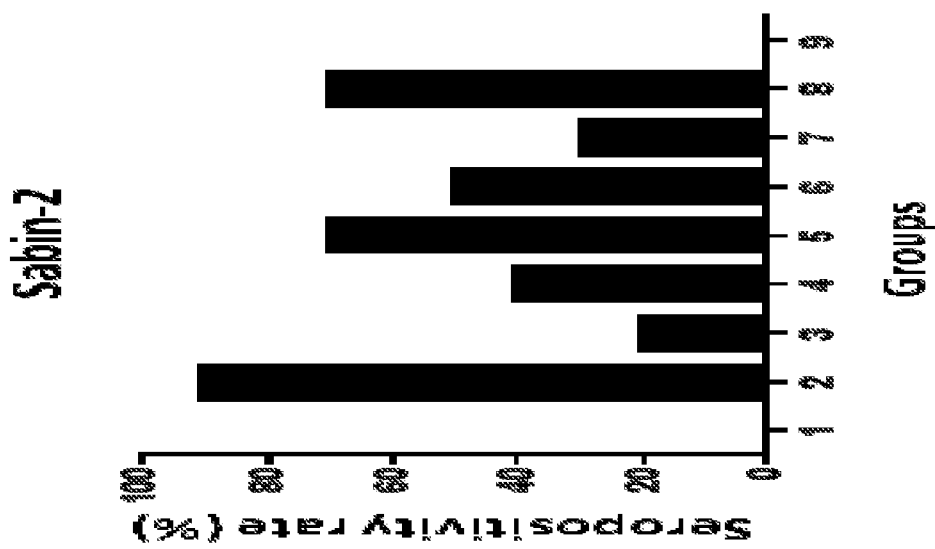
Figure 13C:
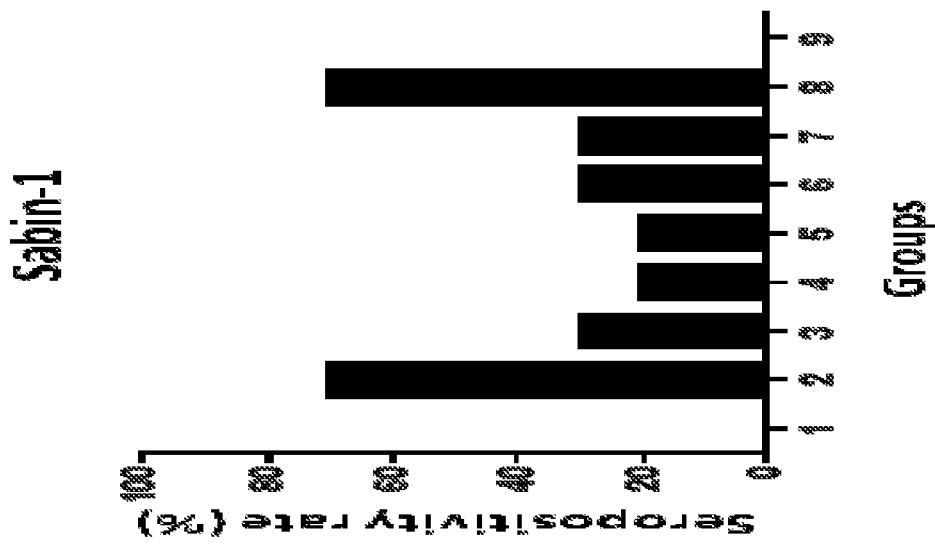
Figure 13E:
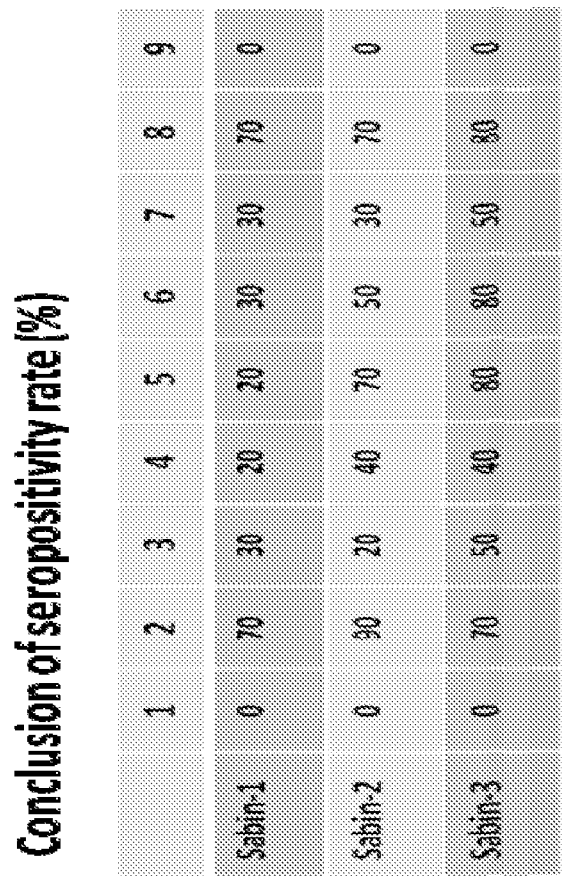
Figure 13D:
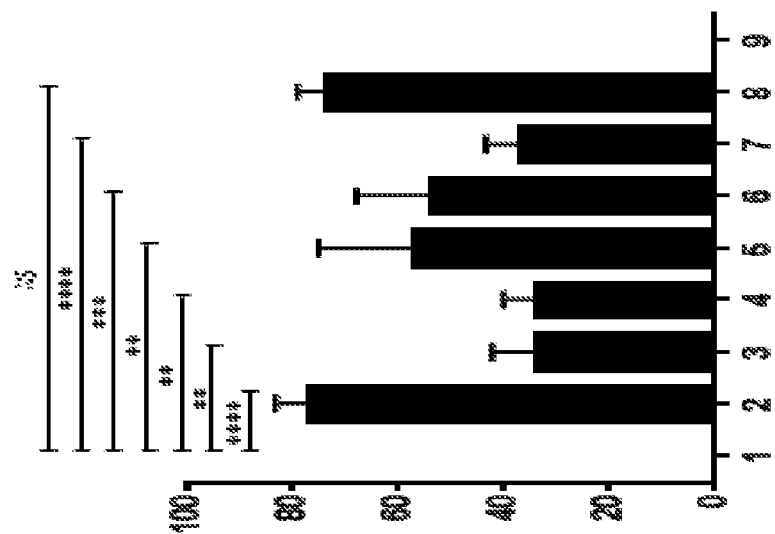

Poliovirus Neutralizing Titers Against all Sabin 1, 2 and 3 Strains Following Priming and Boosting To determine if anti-VP1 IgG1 and IgA antibodies can neutralize poliovirus, virus neutralization titers were measured for all three Sabin serotypes. Blood samples from all experimental and untreated groups were tested in a double blind manner and in triplicate samples at CDC. A serum sample was considered seropositive if antibodies were present at a $\log_2$ titer$\geq$2.5. Individual neutralization titers were plotted, and the bar represents the mean neutralizing titer$\pm$SEM of each group. Results show that after IPV priming, all experimental groups—oral boosting with native (groups 3-5) or codon-optimized VP1 antigen plus either one or both adjuvants (groups 6-9), as well as priming and boosting only with the same IPV (group 2) induced significantly higher neutralizing titers against all three Sabin strain serotypes. Results show that oral boosting with codon-optimized VP1 plus saponin and squalene (group 8) produced the most Sabin 1, Sabin 2 and Sabin 3 neutralizing antibodies, similar to the group of mice that were both primed and boosted with IPV (group 2) (FIG. 12). There was no significant statistical difference in neutralizing efficacy among different Sabin virus serotypes, although Sabin 3 had the highest neutralizing titers with IPV prime/boost ($P<0.01$) and with oral boosting using plant cells ($P<0.001$). However, no neutralizing antibodies were detected in sera from mice that were only orally boosted with codon-optimized VP1 without IPV priming.

To determine the seropositivity rate of poliovirus-neutralizing antibodies, for each Sabin strain, the number of mice with seroprevalence (neutralizing antibody $\log_2$ (titer)$\geq$3) was compared with the total number of mice in each group. Mice boosted with IPV (group 2) or orally boosted with codon-optimized VP1 antigen with saponin and squalene adjuvants (group 8) showed high seropositivity for poliovirus Sabin 1, 2 and 3 neutralizing antibodies (FIG. 13-D). Seropositivity rate varied between 70-90% for IPV prime/boost versus oral boosting with VP1 but there was no statistical difference with similar P values ($<0.001$). These results show that codon-optimized VP1 antigen adjuvanted with both saponin and squalene has the greatest seropositivity rate (FIG. 13) and virus neutralizing titers (FIG. 13) ($\log_2$ titer~3.17-10.17) against all Sabin 1, 2 and 3 strains. This result demonstrates that subunit vaccines bioencapsulated in plant cells can be used as cost-effective booster vaccines against poliomyelitis in countries suffering from a resurgence of wild type poliovirus or cVDPV, which is thought to be caused by OPV boosting.

Discussion

After the outbreak of VDPV2, several critical global policies and processes were adopted in 2013 to support the introduction of at least one dose of IPV into routine immunization schedules to mitigate risks of withdrawal of serotype 2 OPV. The WHO's Strategic Advisory Group of Experts (SAGE) recommended the withdrawal of OPV2 from routine immunization programmes in all countries, facilitated by the introduction of at least one dose of IPV in all OPV-using countries in 2015 and the withdrawal of OPV2 globally in 2016 (the global polio eradication initiative (GPEI), 2015). To accomplish these current priorities, emphasis should be placed on needed activities including licensure and increased availability of bivalent OPV for routine immunization, as well as solid implementation of at least one dose of IPV for all OPV-using countries. However, multiple risks still remain in preparation for the global introduction of IPV and the upcoming switch from trivalent OPV (tOPV) to bivalent OPV (bOPV), including tight IPV supply, persistent cVDPV transmission and challenges to meet containment requirements (GPEI Polio Eradication & Endgame Midterm Review, 2015). Most importantly, there is no booster technology available except IPV which is not affordable for most developing countries. Further, the routine use of OPV vaccination must be discontinued for the global PV eradication, and global introduction of IPV instead of OPV is needed. At the same time, high levels of population immunity against the emergence of VDPV and future outbreaks of wild PV need to be maintained. However, the current cost per vaccine dose of IPV is too high for developing countries.

Expression of VP1 in chloroplasts and bioencapsulation in plant cells can protect antigens from the digestive system upon oral delivery and facilitates their release into the immune system in the gut by commensal microbes[22,23]. CTB-antigen fusions facilitate transmucosal delivery to the immune system via the GM1 intestinal epithelial receptor[24]. Further, CTB-fused vaccine antigens stimulate production of antigen-specific IgG and IgA after priming and oral boosters, conferring protection against toxin/pathogen challenge[22]. Production of green vaccines against infectious diseases with ease of oral administration that does not require a cold chain is an important need, especially in areas with limited access to cold storage and transportation[22]. Previous studies have demonstrated that biopharmaceutical or antigen proteins can be stored in lyophilized plant material at room temperature for several months or even 2 years without any detectable degradation[25-27]. VP1 is highly stable in lyophilized plant cells when stored at ambient temperature for several months.

Antigen-specific IgG and IgA were significantly induced after few oral boosts are adequate to generate high levels of systemic and mucosal immunity. Both VP1-IgG1 and VP1-IgA titers reached highest levels after the first month of oral boosting and did not increase further with more number of boosters. Although neutralization data from later stage sera collection is provided here, previous batches evaluated for Sabin serotype 1 neutralization showed similar results in groups boosted with plant cells expressing VP1 (data not shown). In this study, plant cells were suspended in PBS before oral delivery but for delivery to children, suitable formulation with sugar syrup can be required. Although IPV is highly effective in inducing systemic antibodies to protect against paralytic disease, it is less efficient in inducing the mucosal immunity that is needed to prevent re-infection and excretion of polioviruses into the environment. Our results confirmed that in mice s.c. primed/boosted with IPV minimal IgA titers, explaining the inadequate mucosal immunity of IPV. Mice s.c. primed with IPV and orally boosted with bioencapsulated VP1 elicited strong antigen-specific serum IgG1 (>12,800 titer) and IgA (>800 titer) responses, confirming that oral delivery of VP1 antigen with adjuvants generated both systemic and mucosal immune responses. Unlike viral immunization, subunit vaccines mainly induce Th2 response with IgG1 isotype antibody[28-30]. Oral boosting with subunit vaccines elicits both the mucosal and systemic immune response, as shown by high IgG1/IgA titers.

In this study, we evaluated both native and codon-optimized VP1 antigens expressed in chloroplasts. The level of VP1 protein was much higher in plants expressing codon-optimized VP1. Our in vivo study also showed that vaccination with codon-optimized VP1 induced much higher IgG1 and IgA antibody responses (FIG. 11A-J) than native VP1, indicating that the higher amount of antigen proteins orally delivered in the vaccine formulations is more effective for oral immunization. The antibody titers increased despite the longer interval between boosts, indicating that boosting with subunit vaccines can produce a strong memory immune response.

Neutralizing antibody levels at a titer above the 1:8 dilution (3 $\log_2$(titer)) threshold are accepted by all national regulatory agencies as having a good correlation with protection when reviewing license applications for IPV-containing vaccines[21, 31]. As expected, virus-neutralizing titers induced by priming and boosting with IPV were high for all Sabin strains. In our study, priming with IPV and orally boosting with bioencapsulated VP1 with adjuvant (saponin and squalene) showed the highest seropositivity and virus neutralizing titers (range 3.17-10.17 $\log_2$ titer) against all Sabin 1, 2, 3 strains. Although mice that were only boosted with VP1 plus two adjuvants but not primed (group 9) showed the strongest VP1-specific antibody (IgG1 and IgA) production, no neutralizing virus titers were observed in this group when compared to the mice that were primed with IPV. Thus, the only oral boosting with subunit vaccination appears to be insufficient to induce a good neutralizing antibody response to the antigen. These high anti-VP1 antibodies by ELISA might only bind to viral protein which are expressed on the surface of infected cells but not, to a significant degree, on free virus particles, so that they cannot neutralize virus and protect cells against viral infection[32]. The high concentrations of neutralizing antibody are required to inhibit cell-cell transmission of virus infection[33-35]. These results demonstrate that oral priming is essential to induce adequate immunity against pathogens.

Although this study focuses on polio booster vaccine, there is greater need to boost immunity as life expectancy is on the rise. Loss of immunity against infectious diseases among elderly population is a growing concern. For example, shingles occur when latent chickenpox virus is reactivated when aging weakens the immune system and this is rarely observed due to new viral infections. Therefore, to enhance immunity against a number of infectious diseases among elderly population, low cost oral booster vaccines could serve this purpose. In conclusion, virus- and cold chain-free vaccines are not currently available for any infectious disease. Therefore, production and oral delivery of vaccines using transplastomic technology will facilitate the development of low-cost cold chain- and virus-free booster vaccines. Here we show a low-cost booster vaccine using bioencapsulated polio antigens as an alternative strategy to avoid repeated OPV vaccinations for global PV eradication and the prevention of polio outbreaks in endemic areas.

REFERENCES

1. Burns, C. C., Diop, O. M., Sutter, R. W. & Kew, O. M. Vaccine-derived polioviruses. *J. Infect. Dis.* 210 (Suppl. 1), S283-S293 (2014).
2. Famulare, M. & Hu, H. Extracting transmission networks from phylogeographic data for epidemic and endemic diseases: Ebola virus in Sierra Leone, 2009 H1N1 pandemic influenza and polio in Nigeria. *Int. Health* 7, 130-138 (2015).
3. Burns, C. C. et al. Multiple independent emergences of type 2 vaccine-derived polioviruses during a large outbreak in northern Nigeria. *J. Virol.* 87, 4907-4922 (2013).
4. Laxmivandana, R., Yergolkar, P., Gopalkrishna, V. & Chitambar, S. D. Characterization of the non-polio enterovirus infections associated with acute flaccid paralysis in South-Western India. *PLoS One* 8, e61650 (2013).
5. Dhole, T. N. et al. Non-polio enteroviruses in acute flaccid paralysis children of India: vital assessment before polio eradication. *J. Paediatr. Child. Health* 45, 409-413 (2009).
6. Brown, B., M. S. Oberste, K. Maher, & M. A. Pallansch. Complete genomic sequencing shows that polioviruses and members of human enterovirus species C are closely related in the noncapsid coding region. *J. Virol.* 77, 8973-8984 (2003).
7. Rakoto-Andrianarivelo, M. et al. High frequency of human enterovirus species C circulation in Madagascar. *J. Clin. Microbiol.* 43, 242-249 (2005).
8. Adeniji, J. A. & Faleye, T. O. Enterovirus C strains circulating in Nigeria and their contribution to the emergence of recombinant circulating vaccine-derived polioviruses. *Arch. Virol.* 160, 675-683 (2015).
9. Jiang, P. et al. Evidence for emergence of diverse polioviruses from C-cluster coxsackie A viruses and implications for global poliovirus eradication. *Proc. Natl. Acad. Sci. USA* 104, 9457-9462 (2007).
10. Kouiayskaia, D. et al. Intradermal inactivated poliovirus vaccine: a preclinical dose-finding study. *J. Infect. Dis.* 211, 1447-1450 (2015).
11. Parker, E. P., Molodecky, N. A., Pons-Salort, M., O'Reilly, K. M. & Grassly, N. C. Impact of inactivated poliovirus vaccine on mucosal immunity: implications for the polio eradication endgame. *Expert Rev. Vaccines* 14, 1113-1123 (2015).
12. Chan, H. T. & Daniell, H. Plant-made oral vaccines against human infectious diseases—Are we there yet? *Plant Biotechnol. J.* 13, 1056-1070 (2015).
13. Xiao, Y. et al. Low cost delivery of proteins bioencapsulated in plant cells to human non-immune or immune modulatory cells. *Biomaterials* doi:10.1016/j.biomaterials.2015.11.051 (2015).
14. Jin, S. & Daniell, H. The engineered chloroplast genome just got smarter. *Trends Plant Sci.* 20, 622-640 (2015).
15. Kwon, K. C., Verma, D., Singh, N. D., Herzog, R. & Daniell H. Oral delivery of human biopharmaceuticals, autoantigens and vaccine antigens bioencapsulated in plant cells. *Adv. Drug Deliv. Rev.* 65, 782-799 (2013).
16. Kong., Q. et al. Oral immunization with hepatitis B surface antigen expressed in transgenic plants. *Proc. Natl. Acad. Sci. USA* 98, 11539-11544 (2001).

17. Thanavala, Y. et al. Immunogenicity in humans of an edible vaccine for hepatitis B. *Proc. Natl. Acad. Sci. USA* 102, 3378-3382 (2005).
18. Rybicki, E. P. Plant-based vaccines against viruses. *Virol. J.* 11, 205-224 (2014).
19. de Costa, F. et al. Alternative inactivated poliovirus vaccines adjuvanted with Quillaja *brasiliensis* or Quil-a saponins are equally effective in inducing specific immune responses. *PLoS One* 9, e105374 (2014).
20. Malik, B., Gupta, R. K., Rath, G. & Goyal, A. K. Development of pH responsive novel emulsion adjuvant for oral immunization and in vivo evaluation. *Eur. J. Pharm. Biopharm.* 87, 589-597 (2014).
21. Verdijk, P. et al. Safety and immunogenicity of a primary series of Sabin-IPV with and without aluminum hydroxide in infants. *Vaccine* 32, 4938-4944 (2014).
22. Davoodi-Semiromi, A. et al. Chloroplast-derived vaccine antigens confer dual immunity against cholera and malaria by oral or injectable delivery. *Plant Biotechnol. J.* 8, 223-242 (2010).
23. Limaye, A., Koya, V., Samsam, M. & Daniell, H. Receptor-mediated oral delivery of a bioencapsulated green fluorescent protein expressed in transgenic chloroplasts into the mouse circulatory system. *FASEB J.* 20, 959-961 (2006).
24. Verma, D. et al. Oral delivery of bioencapsulated coagulation factor IX prevents inhibitor formation and fatal anaphylaxis in hemophilia B mice. *Proc. Natl. Acad. Sci. USA* 107, 7101-7106 (2010).
25. Lakshmi, P. S., Verma, D., Yang, X., Lloyd, B. & Daniell, H. Low cost tuberculosis vaccine antigens in capsules: expression in chloroplasts, bio-encapsulation, stability and functional evaluation in vitro. *PLoS One* 8, e54708 (2013).
26. Shil, P. K. et al. Oral delivery of ACE2/Ang-(1-7) bioencapsulated in plant cells protects against experimental uveitis and autoimmune uveoretinitis. *Mol. Ther.* 22, 2069-2082 (2014).
27. Su, J. et al. Low cost industrial production of coagulation factor IX bioencapsulated in lettuce cells for oral tolerance induction in hemophilia B. *Biomaterials* 70, 84-93 (2015).
28. Buchman, G. W. et al. A protein-based smallpox vaccine protects non-human primates from a lethal monkeypox virus challenge. *Vaccine* 28, 6627-6636 (2010).
29. Fogg, C. N. et al. Adjuvant-enhanced antibody responses to recombinant proteins correlates with protection of mice and monkeys to orthopoxvirus challenges. *Vaccine* 25, 2787-2799 (2007).
30. Fogg, C. et al. Protective immunity to vaccinia virus induced by vaccination with multiple recombinant outer membrane proteins of intracellular and extracellular virions. *J. Virol.* 78, 10230-10237 (2004).
31. Plotkin, S. A. Correlates of protection induced by vaccination. *Clin. Vaccine Immunol.* 17, 1055-1065 (2010).
32. Burton, D. R. Antibodies, viruses and vaccines. *Nat. Rev. Immunol.* 2, 706-713 (2002).
33. Burioni, R., Williamson, R. A., Sanna, P. P., Bloom, F. E. & Burton, D. R. Recombinant human Fab to glycoprotein D neutralizes infectivity and prevents cell-to-cell transmission of herpes simplex viruses 1 and 2 in vitro. *Proc. Natl. Acad. Sci. USA* 91, 355-359 (1994).
34. Hooks, J. J., Burns, W., Hayashi, K., Geis, S. & Notkins, A. L. Viral spread in the presence of neutralizing antibody: mechanisms of persistence in foamy virus infection. *Infect. Immun.* 14, 1172-1178 (1976).
35. Pantaleo, G. et al. Effect of anti-V3 antibodies on cell-free and cell-to-cell human immunodeficiency virus transmission. *Eur. J. Immunol.* 25, 226-231 (1995).
36. Ruhlman, T., Ahangari, R. Devine, A. Samsam, M. & Daniell H. Expression of cholera toxin B-proinsulin fusion protein in lettuce and tobacco chloroplasts-oral administration protects against development of insulitis in non-obese diabetic mice. *Plant Biotechnol. J.* 5, 495-510 (2007).
37. Verma, D., Samson, N. P., Koya, V. & Daniell, H. A protocol for expression of foreign genes in chloroplasts. *Nat. Protoc.* 3, 739-758 (2008).
38. Kanagaraj, A. P., Verma, D. & Daniell H. Expression of dengue-3 premembrane and envelope polyprotein in lettuce chloroplasts. *Plant Mol. Biol.* 76, 323-333 (2011).
39. Domingos, M. de 0. et al. A new oil-based antigen delivery formulation for both oral and parenteral vaccination. *Open Drug Deliv. J.* 2, 52-60 (2008).
40. Lee, G. et al. Oral immunization of haemaggulutinin H5 expressed in plant endoplasmic reticulum with adjuvant saponin protects mice against highly pathogenic avian influenza A virus infection. *Plant Biotechnol. J.* 13, 62-72 (2015).
41. Frey, A., Di Canzio & J., Zurakowski, D. A statistically defined endpoint titer determination method for immunoassays. *J. Immunol. Methods* 221, 35-41 (1998).
42. Dietrich, J., Andreasen, L. V., Andersen, P. & Agger, E. M. Inducing dose sparing with inactivated polio virus formulated in adjuvant CAF01. *PLoS One* 9, e100879 (2014).

Example III

Oral Delivery of Codon Optimized Insulin-Like Growth Factor-1

Bioencapsulated in Plant Chloroplasts

Human insulin-like growth factor 1 (IGF-1) plays important roles in growth and development of skeletal muscle in myoblast/fiber formation, differentiation and regeneration after injury. Because E peptide enhances efficacy of IGF-1, it is desirable to express Pro-IGF-1 in chloroplasts to reduce cost and facilitate oral delivery.

Figure 17A:
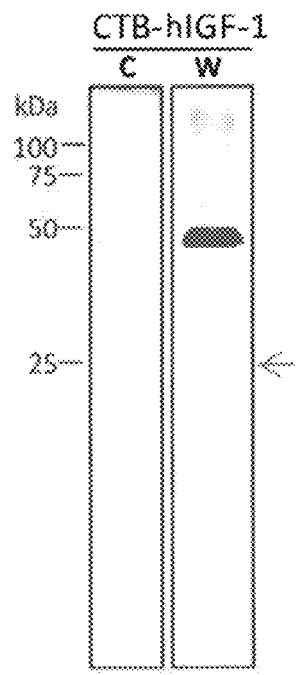
Figure 17B:
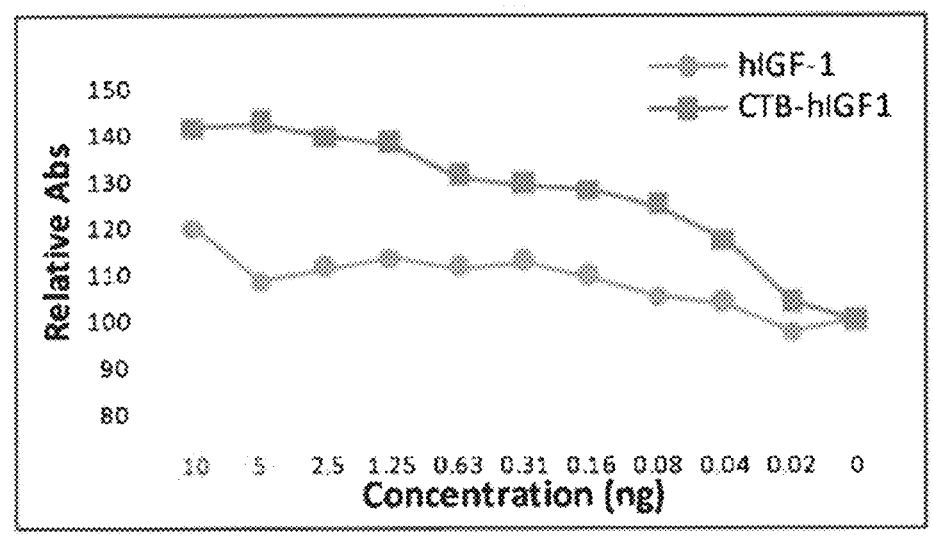
Figure 17C:
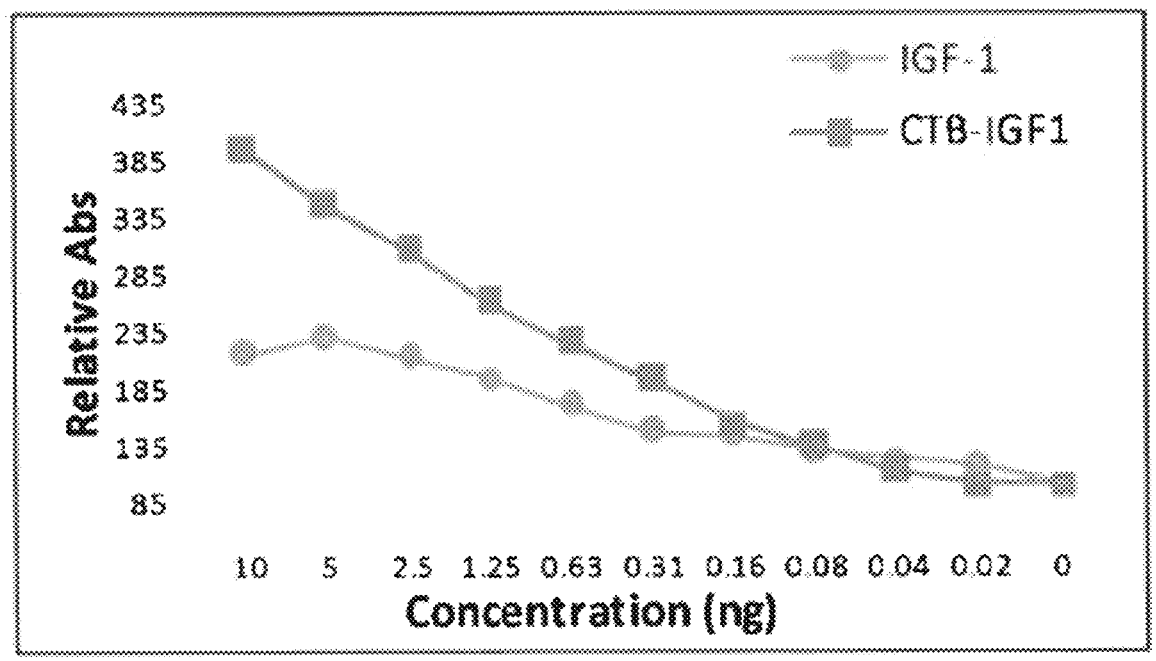
Figure 17D:
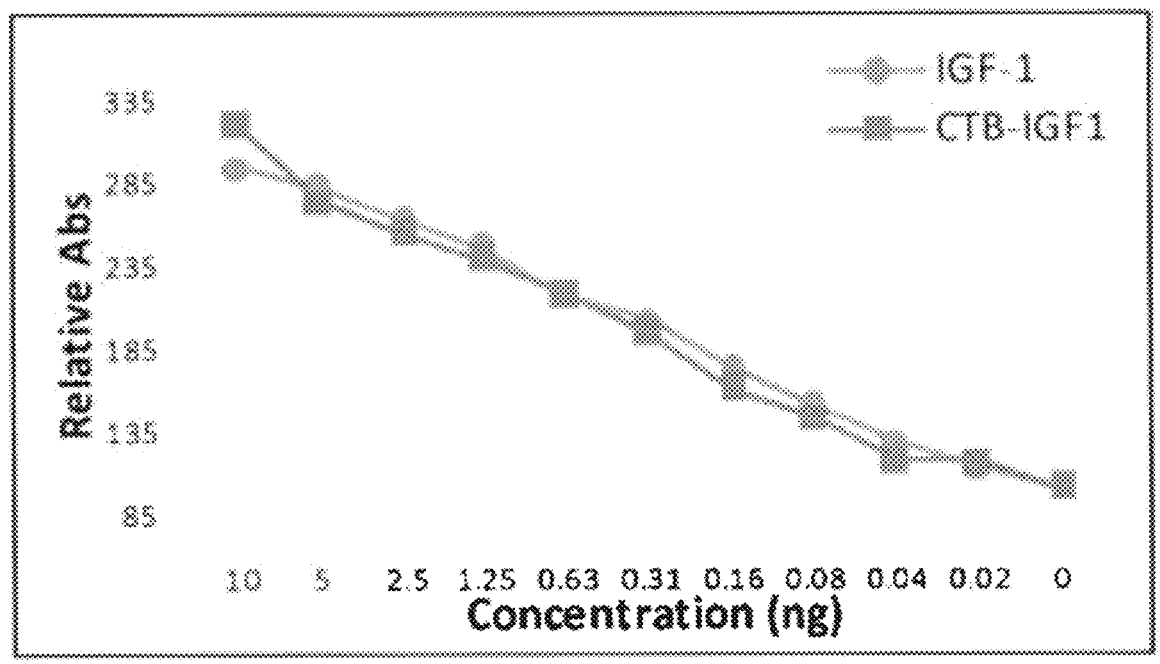
Figure 17E:
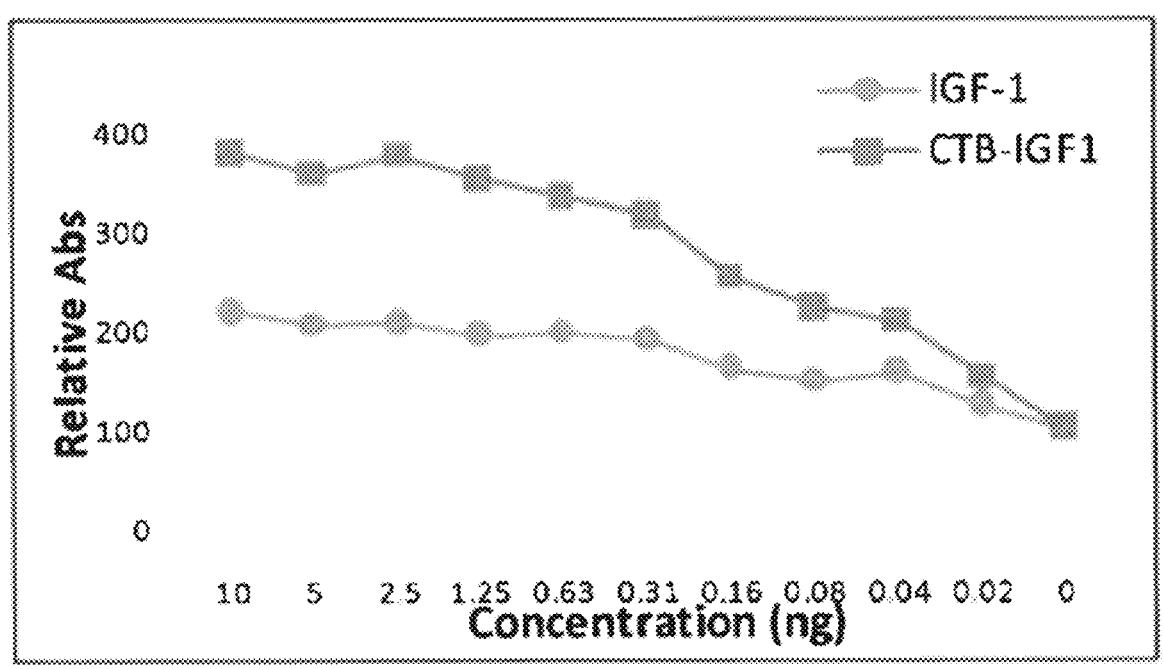

Pro-IGF-1E (105 aa) was codon-optimized using a software developed described in Example I based the most highly expressed chloroplast gene from 133 plant species (See FIG. 17F). The synthetic pro-IGF-1E was fused to native sequence Cholera toxin B subunit (CTB) and inserted into chloroplast vector as shown in FIG. 14A. Immunoblot assays for the expression of codon-optimized sequences for IGF-1 were performed in *E. coli*. Total proteins were extracted from transformed *E. coli* with chloroplast expression vectors containing two codon-optimized sequences ($C^o$, codon-optimized old; $C^N$, codon-optimized new) for IGF-1. Arrow in FIG. 14B indicates expected proteins in size (CTB-IGF-1, 24.3 kDa). Southern blot analysis of CTB-IGF-1 transplastomic lines is shown in FIG. 14C. FIGS. 15A-15D show quantification and functional analysis of codon-optimized IGF-1 in transplastomic cell lines.

Figure 16B:
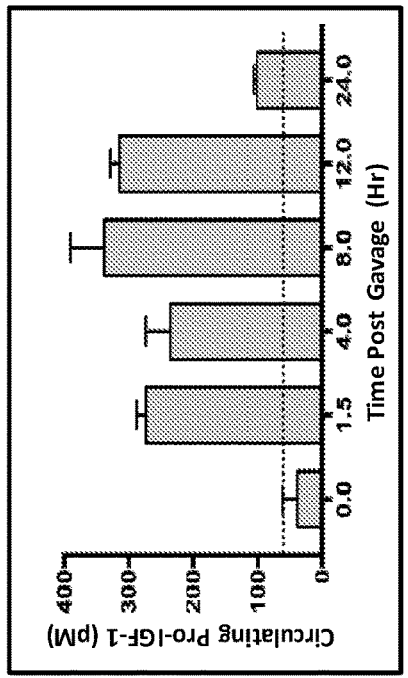
Figure 16D:
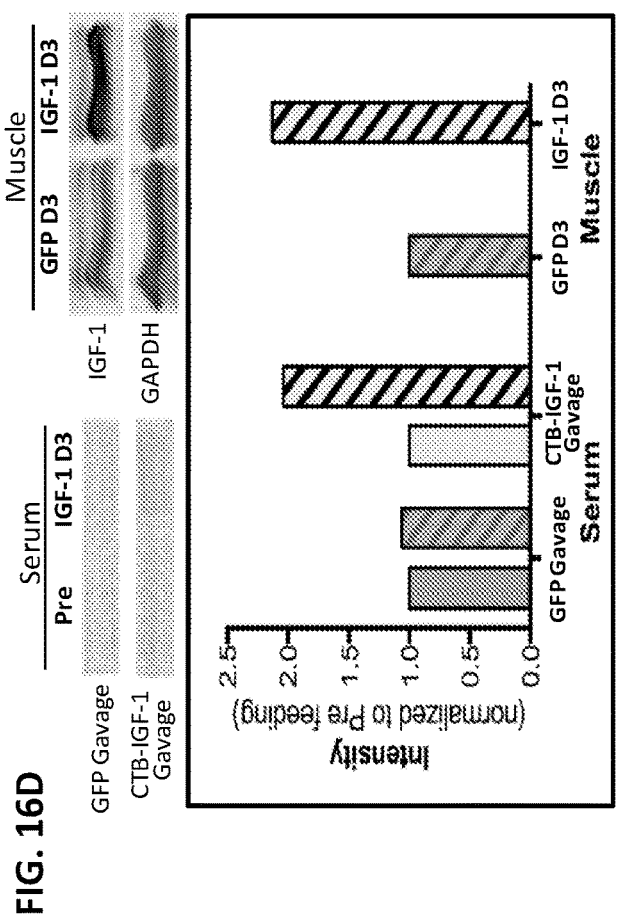
Figure 16A:
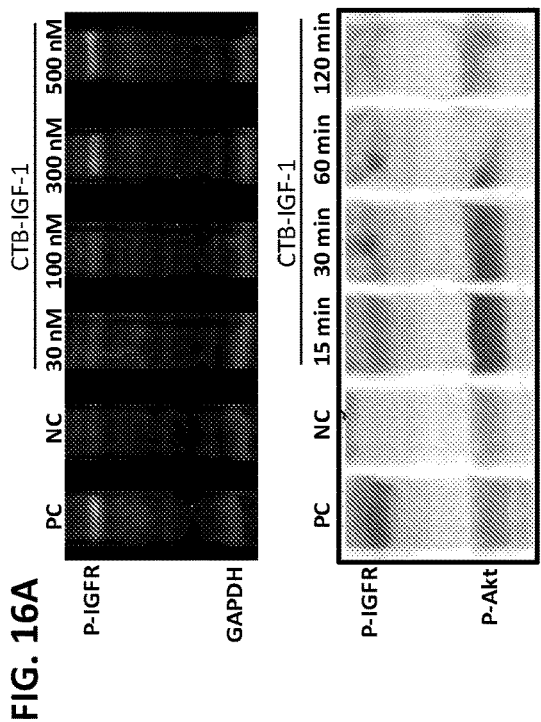
Figure 16C:
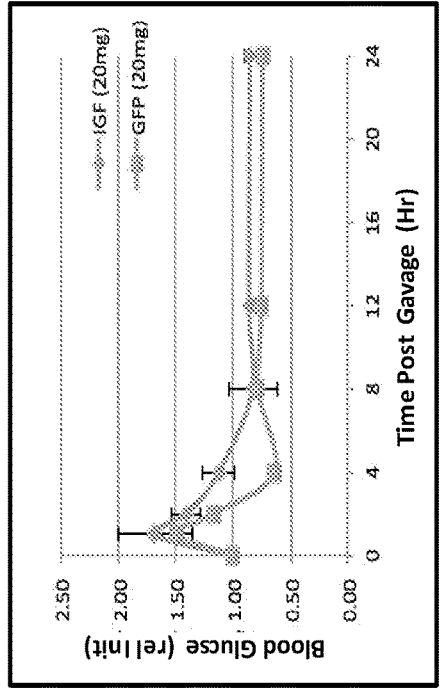

Phosphorylation of IGF-1 receptor (IGFR) by plant derived CTB-Pro-IGF-1 was examined in vitro and the results are shown in FIG. 16A. FIGS. 16B-D show free Pro-IGF-1 in circulatory system as measured in mice after oral gavage of CTB-Pro-IGF-1. CTB-Pro-IGF-1 was also evaluated by proliferation assay of four human/mouse oral cell lines. See FIG. 17A-17E.

Among 105 aa, 73 codons were modified resulting in 57% AT content in codon optimized IGF-1 gene. To avoid glycosylation Lsy68, Arg74 and Arg77 were changed to Gly68, Ala74 and Ala77. See FIG. 17F. Examined lines showed homoplasmy (integration into all chloroplast genomes) in Southern blots and high level expression of CTB-IGF1. GM1 ELISA in the lyophilized plant cells confirmed preservation of pentameric form of CTB-Pro-IGF-1 and folding with disulfide bonds. Chloroplast-derived CTB-Pro-IGF-1 phosphorylated IGF-1 Receptor (IGFR) in P6 cells in a dose- and time-dependent manner.

Figure 18A:
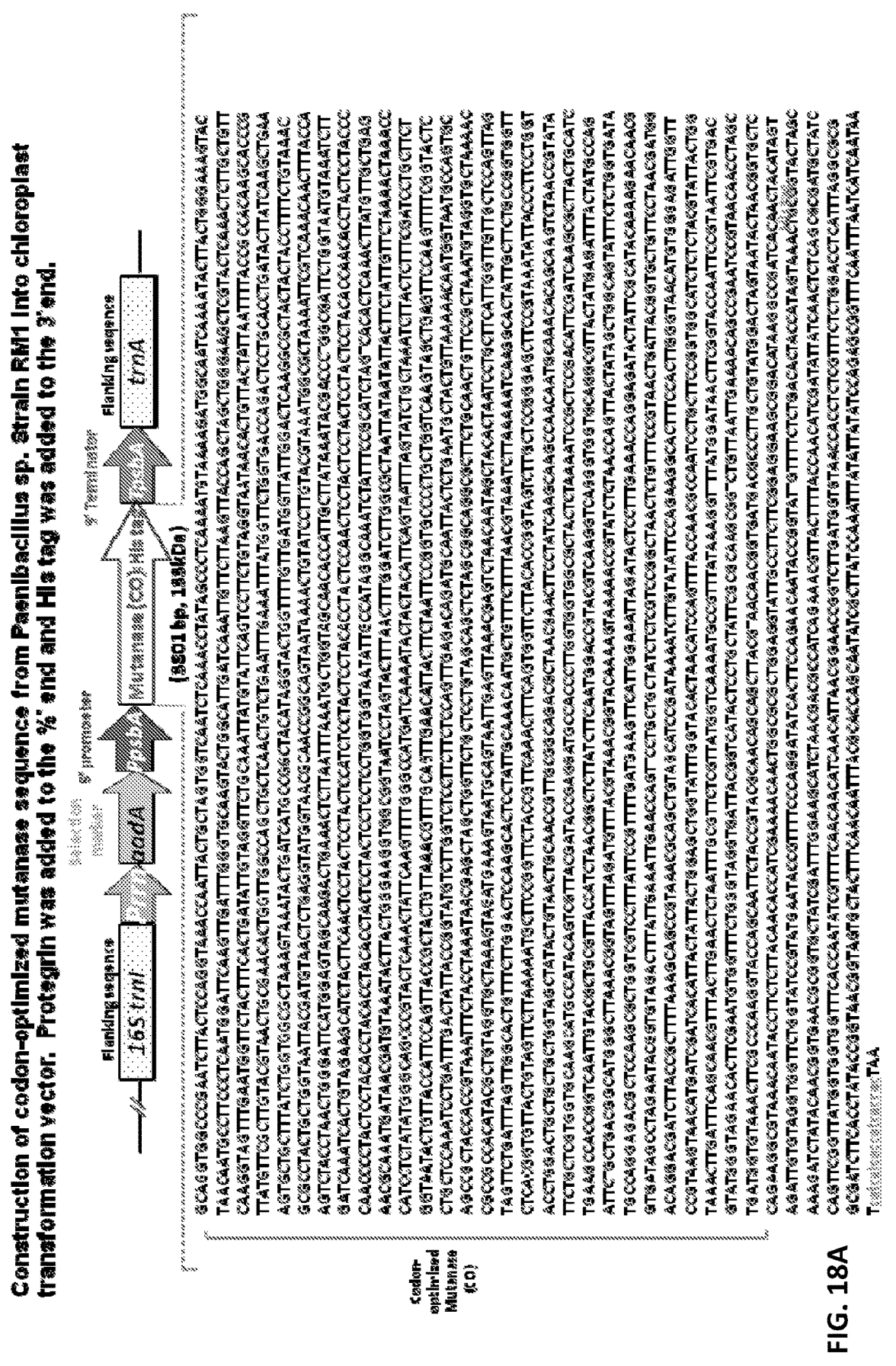

Pro-IGF-1 increased 3-fold in blood after oral delivery of lyophilized plant cells at 8 hrs and was maintained up to 24 hrs (FIG. 18C); pro-IGF-1 was 2-fold higher in the muscle tissue (FIG. 16D). Purified CTB-Pro-IGF-1 from plant cells stimulated (1.4 to 3.9 fold higher) proliferation of human oral keratinocytes, gingival derived mesenchymal stromal cells, head and neck squamous carcinoma cells, and mouse osteoblast, in a dose dependent manner.

Conclusions

The phosphorylation of IGFR by plant derived CTB-Pro-IGF-1 and the maintenance Pro-IGF-1 in the circulatory system and in the muscle tissue after oral gavage confirms suitability of this system for low cost production and delivery of functional IGF1 bioencapsulated in plant cells. Lyophilized plant cells can be stored indefinitely at ambient temperature without decrease in efficacy of IGF-1.

Clinical Significance

Expression of Pro-IGF-1 with E peptide in chloroplasts provides an effective, efficient and affordable oral drug delivery concept for treatment of disorders caused by IGF-1 deficiency including muscle disorders. This approach offers a technological breakthrough to address the rising cost of healthcare in addition to increasing patient compliance for repetitive long-term drug delivery.

Example IV

Affordable Biopharmaceutical Made in Lettuce to Treat Dental Caries

Dental Caries is a prevalent biofilm-associated oral disease worldwide. Antimicrobials are minimally effective as they do not penetrate the exopolysaccharide (EPS) matrix. Therefore, in the present example, we express EPS degrading enzymes dextranase and mutanase fused with antimicrobial peptides (AMP). The recombinant enzyme production in plant chloroplasts is 1000-3,100-fold cheaper because it eliminates prohibitively expensive fermentation, purification, cold storage/transportation and invasive surgical delivery and facilitates storage at ambient temperature. The primary goal of this example is to develop chewing gums impregnated with lyophilized plant cells expressing AMP and enzymes. Hence, an initial study was performed to optimize the chewing rates and time for maximum drug release using chewing simulator with chewing gum made from lyophilized plant cells expressing reporter gene GFP.

Figure 18B:
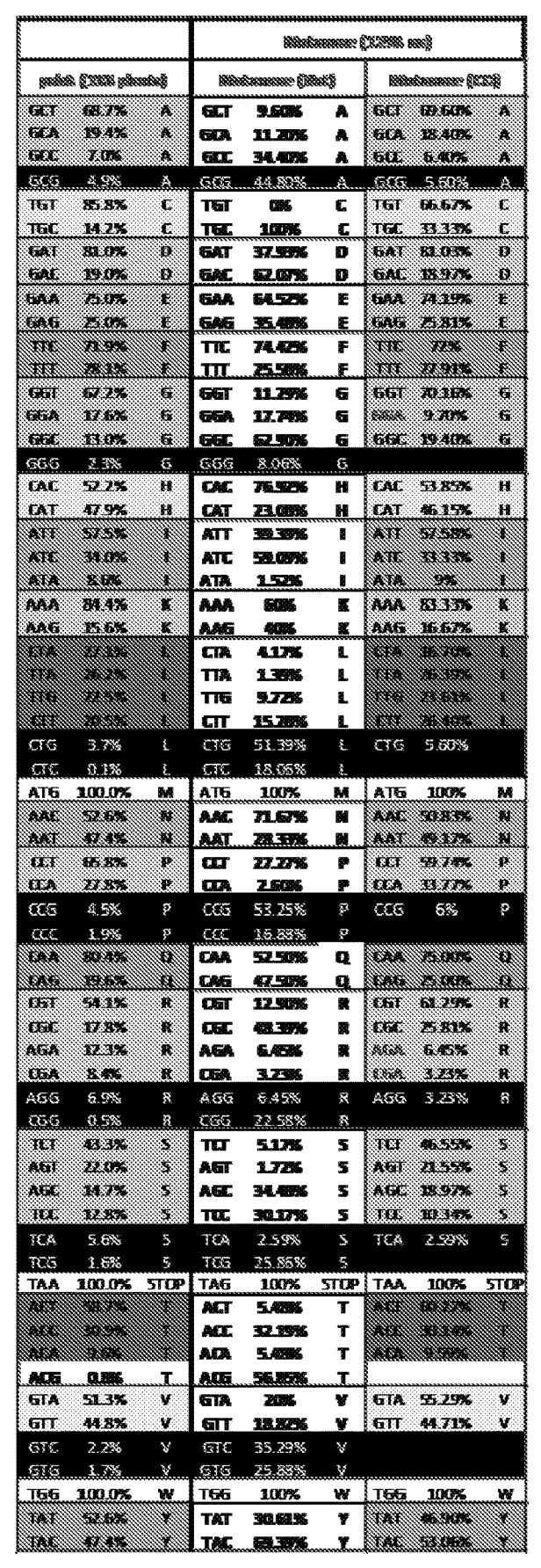
Figure 18C:
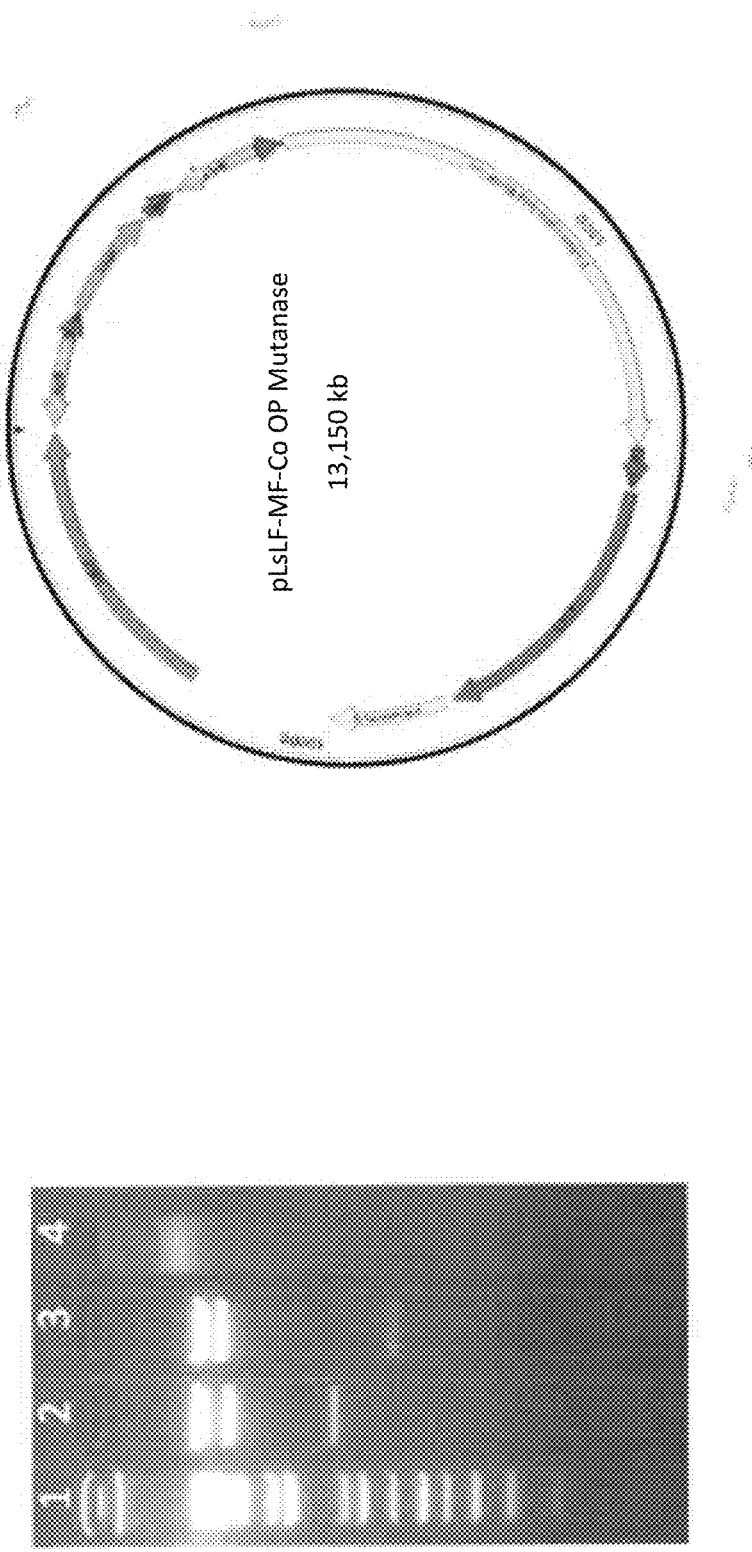
FIG. 18C. Confirmation of Mutanase gene in pLS-MF vector by restriction digestion. Lane 1: DNA Marker; Lane 2: pLS-MF Mutanase digested with Nde I and Bgl II; Lane 3: pLS-MF Mutanase digested with Sal I and PshA II; Lane 4: Undigested plasmid.
Figure 18D:
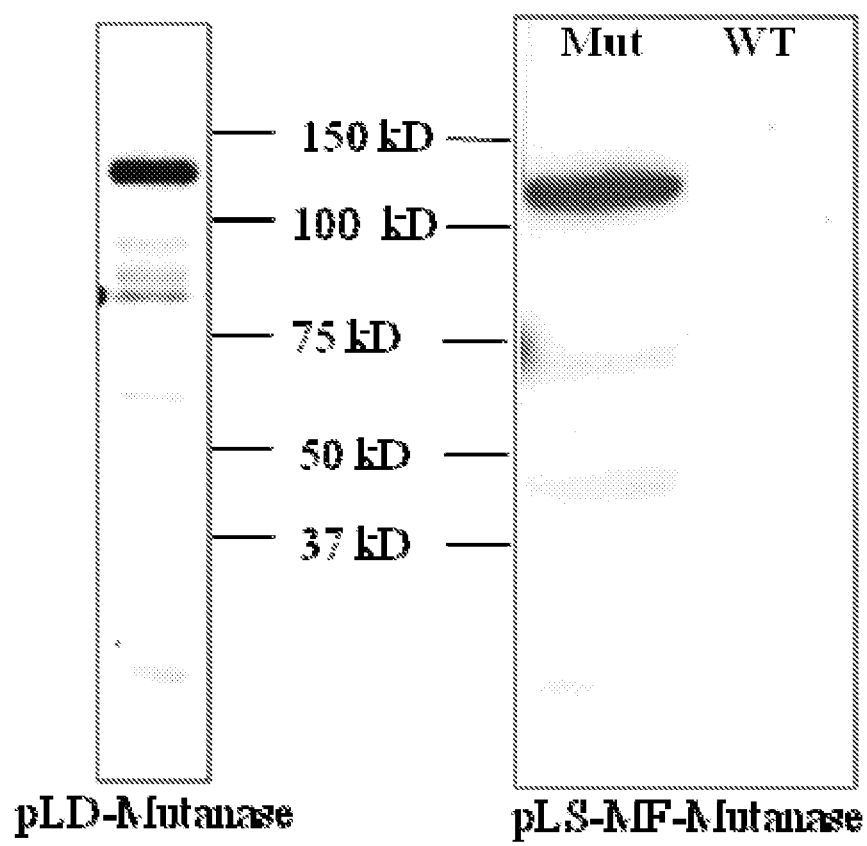
FIG. 18D. Western blot analysis to detect expression of recombinant proteins in *E. coli*: Western blot probed with Anti-His antibody. Mutanase gene was cloned into pLD and pLS-MF vector and expressed in *E. coli*. The protein was further purified and its expression was confirmed by Western Blot.
Figure 18F:
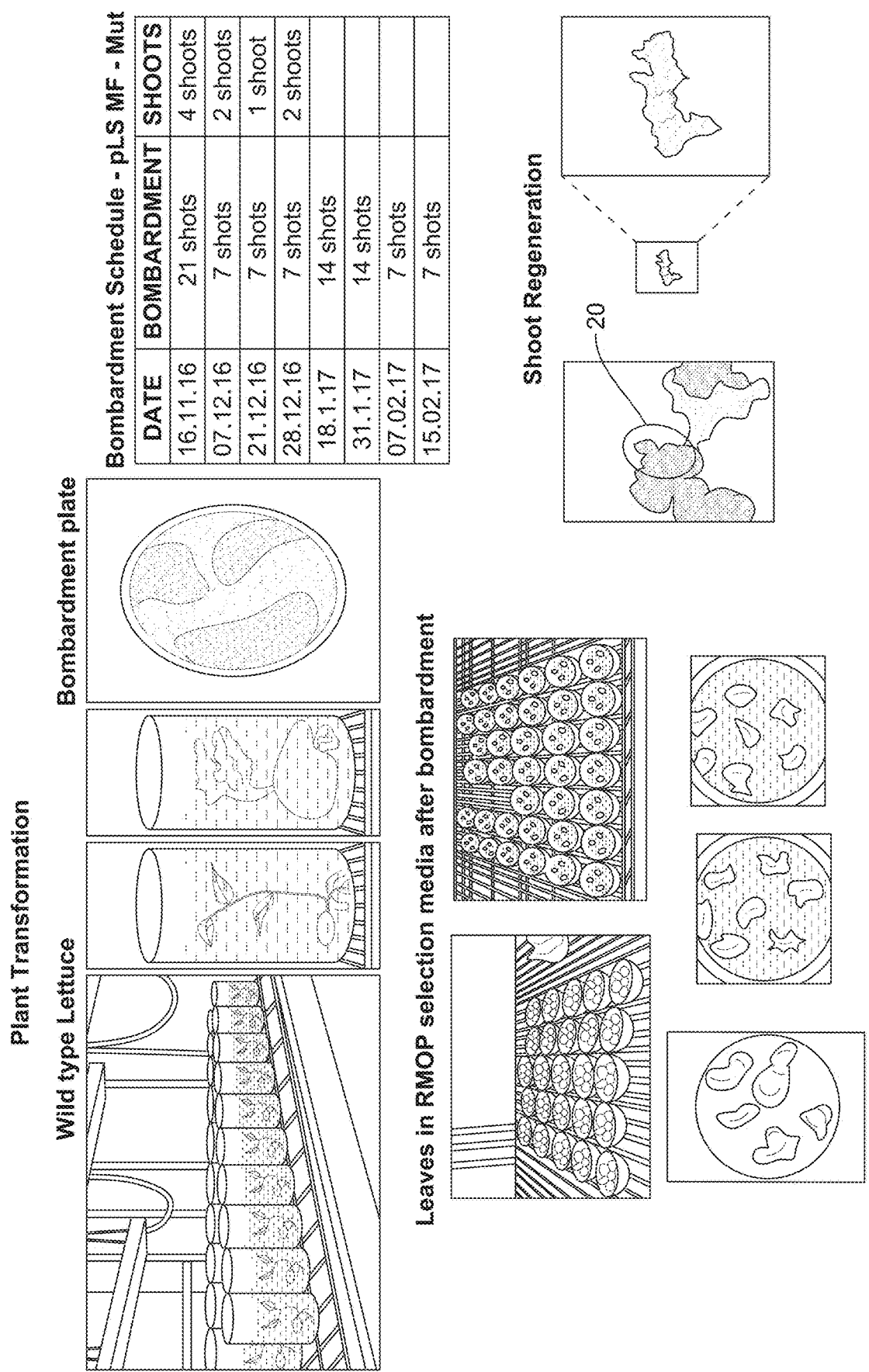
FIG. 18F. A schematic of the process of plant transformation for creation of transplastomic plants expressing mutanase.

Dextranase gene from *Streptococcus nutans* and mutanase gene from *Paenibacillus* was either fused with PG1 or without PG1 was cloned into chloroplast vectors and their functionality was evaluated first in *E. coli*. See FIG. 18A. The difference in codon usage between the naturally occurring enzyme and the optimized version is shown in FIG. 18B. The optimized gene was cloned into a lettuce expression vector as described above and shown in FIG. 18C. Western blotting confirmed robust protein expression. See FIG. 18D. Chewing simulator was used to study release kinetics of gum tablets by quantifying GFP in the artificial saliva. A new codon optimization algorithm replaced 586 (out of 1261) rare codons with preferred codons in the mutanase gene based on the psbA codon hierarchy. Codon optimized mutanase gene (with or without AMP fusion) was cloned into tobacco and lettuce chloroplast vectors and expressed in *E. coli* were fully functional, similar to commercial enzymes. See FIG. 18E. The native dextranase gene was cloned into the tobacco chloroplast vector and the dextranase activity in *E. coli* was tested. The recombinant dextranase produced by *E. coli* degrade blue dextran on the agar plate, confirming dextran hydrolysis. The process for the creation and characterization of transplastomic lines is shown in FIG. 18F.

GFP in gum tablets was not significantly degraded during gum preparation. The chewing rate, time required for maximum protein release is currently optimized using chewing simulator. Accordingly, production of EPS-degrading enzymes fused with AMP should provide a promising treatment for dental caries, preferably administered as gum tablets.

While certain of the preferred embodiments of the present invention have been described and specifically exemplified above, it is not intended that the invention by limited to such embodiments. Various modifications may be made thereto without departing from the scope and spirit of the present invention, as set forth in the following claims.

What is claimed is:

1. A method for increasing translation of a transgene encoding a protein of interest in a chloroplast, said method comprising
   a) replacing codons in a native sequence encoding a protein of interest with preferred codons preferentially used in psbA genes in chloroplasts in higher seed plants species;
   b) producing a synthetic, codon optimized sequence and cloning said sequence into a chloroplast transformation vector, said synthetic sequence being operably linked to 5' and 3' regulatory elements suitable for expression in said chloroplast;
   c) transforming a target plant with said vector, under conditions whereby said protein of interest is expressed, wherein replacing codons in said native sequence with preferred codons causes at least a two fold increase in protein expression relative to expression levels observed using the native sequence
wherein
   each codon for phenylalanine is replaced with a preferred TTT codon;
   each codon for leucine is replaced with a preferred TTA codon;
   each codon for isoleucine is replaced with a preferred ATT codon;
   each codon for valine is replaced with a preferred GTA codon;
   each codon for serine is replaced with a preferred TCT codon;
   each codon for proline is replaced with a preferred CCT codon;
   each codon for threonine is replaced with a preferred ACT codon;
   each codon for alanine is replaced with a preferred GCT codon;
   each codon for tyrosine is replaced with a preferred TAT codon;
   each codon for histidine is replaced with a preferred CAC codon;
   each codon for glutamine is replaced with a preferred CAA codon;
   each codon for asparagine is replaced with a preferred AAC codon;
   each codon for lysine is replaced with a preferred AAA codon;
   each codon for aspartic acid is replaced with a preferred GAT codon;
   each codon for glutamic acid is replaced with a preferred GAA codon;
   each codon for cysteine is replaced with a preferred TGT codon;
   each codon for tryptophan is replaced with a preferred TGG codon;
   each codon for arginine is replaced with a preferred CGT codon; and
   each codon for glycine is replaced with a preferred GGT codon.

2. The method of claim 1 further comprising isolating said protein of interest.

3. The method of claim 1 further comprising harvesting and lyophilizing leaves from said plant, said lyophilized leaves comprising the protein of interest.

4. A plastid transformation vector encoding a psbA codon optimized nucleic acid encoding the protein of claim 2.

5. A plant transformed with the vector of claim 4.

6. The plant of claim 5 which is edible.

7. A method for increasing translation of a transgene encoding a protein of interest in a chloroplast, said method comprising
   a) analyzing the native sequence of a nucleic acid encoding said protein of interest and replacing codons in said sequence with those preferentially used in psbA genes in chloroplasts in higher plants;
   b) producing a synthetic, codon optimized sequence and cloning said sequence into a chloroplast transformation vector, said synthetic sequence being operably linked to 5' and 3' regulatory elements suitable for expression in said chloroplast;
   c) transforming a target plant with said vector, under conditions whereby said protein of interest is expressed, wherein replacing said codons causes at least a two fold increase in protein expression relative to expression levels observed using the native sequence, wherein the vector encodes a synthetic mutanase encoded by SEQ ID NO: 25.

8. The method of claim 1, further comprising increasing AT content in said codon optimized sequence.

* * * * *